A mount assembly for use with a robotic system is provided and includes a housing for coupling to a robot arm; a coupling assembly supported by the housing and including first and second arms, the coupling assembly transitionable between open and closed configurations, wherein in the closed configuration the first and second arms are configured to secure a surgical accessory; a release assembly supported by the housing and engagable with the coupling assembly, the release assembly transitionable between a locked configuration and an unlocked configuration; and a communication assembly supported by the housing and configured for communication with the robotic system with respect to a

United States Patent
Traina

(10) Patent No.: US 11,432,890 B2
(45) Date of Patent: Sep. 6, 2022

(54) SYSTEMS AND ASSEMBLIES FOR MOUNTING A SURGICAL ACCESSORY TO ROBOTIC SURGICAL SYSTEMS, AND PROVIDING ACCESS THERETHROUGH

(71) Applicant: Covidien LP, Mansfield, MA (US)

(72) Inventor: Zachary Traina, Verona, NJ (US)

(73) Assignee: Covidien LP, Mansfield, MA (US)

( * ) Notice: Subject to any disclaimer, the term of this patent is extended or adjusted under 35 U.S.C. 154(b) by 0 days.

(21) Appl. No.: 16/771,756

(22) PCT Filed: Jan. 2, 2019

(86) PCT No.: PCT/US2019/012045
§ 371 (c)(1),
(2) Date: Jun. 11, 2020

(87) PCT Pub. No.: WO2019/136062
PCT Pub. Date: Jul. 11, 2019

(65) Prior Publication Data
US 2021/0137611 A1    May 13, 2021

Related U.S. Application Data
(60) Provisional application No. 62/613,601, filed on Jan. 4, 2018.

(51) Int. Cl.
*A61B 34/30*     (2016.01)
*A61B 90/57*     (2016.01)
(Continued)

(52) U.S. Cl.
CPC .......... *A61B 34/30* (2016.02); *A61B 17/3423* (2013.01); *A61B 90/57* (2016.02);
(Continued)

(58) Field of Classification Search
CPC ......... A61B 34/30; A61B 34/35; A61B 34/37; A61B 17/3423; A61B 17/3421;
(Continued)

(56) References Cited

U.S. PATENT DOCUMENTS

| 4,863,133 A | 9/1989 | Bonnell |
| 5,603,702 A | 2/1997 | Smith et al. |

(Continued)

FOREIGN PATENT DOCUMENTS

| EP | 0293760 B1 | 2/1995 |
| EP | 3130305 A1 | 2/2017 |

(Continued)

OTHER PUBLICATIONS

International Search Report dated Apr. 24, 2019 and Written Opinion completed Apr. 24, 2019 corresponding to counterpart Int'l Patent Application PCT/US19/12045.

(Continued)

*Primary Examiner* — Tan-Uyen T Ho
*Assistant Examiner* — Bridget E. Rabaglia
(74) *Attorney, Agent, or Firm* — Carter, DeLuca & Farrell LLP

(57) ABSTRACT

A mount assembly for use with a robotic system is provided and includes a housing for coupling to a robot arm; a coupling assembly supported by the housing and including first and second arms, the coupling assembly transitionable between open and closed configurations, wherein in the closed configuration the first and second arms are configured to secure a surgical accessory; a release assembly supported by the housing and engagable with the coupling assembly, the release assembly transitionable between a locked configuration and an unlocked configuration; and a communication assembly supported by the housing and configured for communication with the robotic system with respect to a (Continued)

status of the coupling assembly corresponding to the open and closed configuration thereof; and a status of the release assembly corresponding to the locked and unlocked configuration thereof.

20 Claims, 29 Drawing Sheets

(51) Int. Cl.
    *A61B 17/34*     (2006.01)
    *A61B 34/35*     (2016.01)
    *A61B 46/10*     (2016.01)
    *A61B 17/00*     (2006.01)

(52) U.S. Cl.
    CPC ............... *A61B 34/35* (2016.02); *A61B 46/10* (2016.02); *A61B 2017/00486* (2013.01)

(58) Field of Classification Search
    CPC ........... A61B 2017/00486; A61B 2017/00477; A61B 90/57; A61B 46/10; A61B 2017/3405; A61B 2034/301
    See application file for complete search history.

(56) References Cited

U.S. PATENT DOCUMENTS

| | | | |
|---|---|---|---|
| 5,807,338 A | 9/1998 | Smith et al. | |
| 6,132,368 A | 10/2000 | Cooper | |
| 6,206,903 B1 | 3/2001 | Ramans | |
| 6,228,061 B1 * | 5/2001 | Flatland ............. | A61B 17/3462 604/167.06 |
| 6,246,200 B1 | 6/2001 | Blumenkranz et al. | |
| 6,312,435 B1 | 11/2001 | Wallace et al. | |
| 6,331,181 B1 | 12/2001 | Tierney et al. | |
| 6,346,072 B1 | 2/2002 | Cooper | |
| 6,394,998 B1 | 5/2002 | Wallace et al. | |
| 6,424,885 B1 | 7/2002 | Niemeyer et al. | |
| 6,441,577 B2 | 8/2002 | Blumenkranz et al. | |
| 6,459,926 B1 | 10/2002 | Nowlin et al. | |
| 6,491,691 B1 | 12/2002 | Morley et al. | |
| 6,491,701 B2 | 12/2002 | Tierney et al. | |
| 6,493,608 B1 | 12/2002 | Niemeyer | |
| 6,565,554 B1 | 5/2003 | Niemeyer | |
| 6,645,196 B1 | 11/2003 | Nixon et al. | |
| 6,659,939 B2 | 12/2003 | Moll | |
| 6,671,581 B2 | 12/2003 | Niemeyer et al. | |
| 6,676,684 B1 | 1/2004 | Morley et al. | |
| 6,685,698 B2 | 2/2004 | Morley et al. | |
| 6,699,235 B2 | 3/2004 | Wallace et al. | |
| 6,714,839 B2 | 3/2004 | Salisbury, Jr. et al. | |
| 6,716,233 B1 | 4/2004 | Whitman | |
| 6,728,599 B2 | 4/2004 | Wang et al. | |
| 6,746,443 B1 | 6/2004 | Morley et al. | |
| 6,766,204 B2 | 7/2004 | Niemeyer et al. | |
| 6,770,081 B1 | 8/2004 | Cooper et al. | |
| 6,772,053 B2 | 8/2004 | Niemeyer | |
| 6,783,524 B2 | 8/2004 | Anderson et al. | |
| 6,793,652 B1 | 9/2004 | Whitman et al. | |
| 6,793,653 B2 | 9/2004 | Sanchez et al. | |
| 6,799,065 B1 | 9/2004 | Niemeyer | |
| 6,837,883 B2 | 1/2005 | Moll et al. | |
| 6,839,612 B2 | 1/2005 | Sanchez et al. | |
| 6,840,938 B1 | 1/2005 | Morley et al. | |
| 6,843,403 B2 | 1/2005 | Whitman | |
| 6,846,309 B2 | 1/2005 | Whitman et al. | |
| 6,866,671 B2 | 3/2005 | Tierney et al. | |
| 6,871,117 B2 | 3/2005 | Wang et al. | |
| 6,879,880 B2 | 4/2005 | Nowlin et al. | |
| 6,899,705 B2 | 5/2005 | Niemeyer | |
| 6,902,560 B1 | 6/2005 | Morley et al. | |
| 6,936,042 B2 | 8/2005 | Wallace et al. | |
| 6,951,535 B2 | 10/2005 | Ghodoussi et al. | |
| 6,974,449 B2 | 12/2005 | Niemeyer | |
| 6,991,627 B2 | 1/2006 | Madhani et al. | |
| 6,994,708 B2 | 2/2006 | Manzo | |
| 7,048,745 B2 | 5/2006 | Tierney et al. | |
| 7,066,926 B2 | 6/2006 | Wallace et al. | |
| 7,118,582 B1 | 10/2006 | Wang et al. | |
| 7,125,403 B2 | 10/2006 | Julian et al. | |
| 7,155,315 B2 | 12/2006 | Niemeyer et al. | |
| 7,239,940 B2 | 7/2007 | Wang et al. | |
| 7,306,597 B2 | 12/2007 | Manzo | |
| 7,357,774 B2 | 4/2008 | Cooper | |
| 7,373,219 B2 | 5/2008 | Nowlin et al. | |
| 7,379,790 B2 | 5/2008 | Toth et al. | |
| 7,386,365 B2 | 6/2008 | Nixon | |
| 7,391,173 B2 | 6/2008 | Schena | |
| 7,398,707 B2 | 7/2008 | Morley et al. | |
| 7,413,565 B2 | 8/2008 | Wang et al. | |
| 7,453,227 B2 | 11/2008 | Prisco et al. | |
| 7,524,320 B2 | 4/2009 | Tierney et al. | |
| 7,574,250 B2 | 8/2009 | Niemeyer | |
| 7,594,912 B2 | 9/2009 | Cooper et al. | |
| 7,607,440 B2 | 10/2009 | Coste-Maniere et al. | |
| 7,666,191 B2 | 2/2010 | Orban, III et al. | |
| 7,682,357 B2 | 3/2010 | Ghodoussi et al. | |
| 7,689,320 B2 | 3/2010 | Prisco et al. | |
| 7,695,481 B2 | 4/2010 | Wang et al. | |
| 7,695,485 B2 | 4/2010 | Whitman et al. | |
| 7,699,855 B2 | 4/2010 | Anderson et al. | |
| 7,713,263 B2 | 5/2010 | Niemeyer | |
| 7,725,214 B2 | 5/2010 | Diolaiti | |
| 7,727,244 B2 | 6/2010 | Orban, III et al. | |
| 7,741,802 B2 | 6/2010 | Prisco | |
| 7,756,036 B2 | 7/2010 | Druke et al. | |
| 7,757,028 B2 | 7/2010 | Druke et al. | |
| 7,762,825 B2 | 7/2010 | Burbank et al. | |
| 7,763,015 B2 | 7/2010 | Cooper et al. | |
| 7,778,733 B2 | 8/2010 | Nowlin et al. | |
| 7,803,151 B2 | 9/2010 | Whitman | |
| 7,806,891 B2 | 10/2010 | Nowlin et al. | |
| 7,819,859 B2 | 10/2010 | Prisco et al. | |
| 7,819,885 B2 | 10/2010 | Cooper | |
| 7,824,401 B2 | 11/2010 | Manzo et al. | |
| 7,835,823 B2 | 11/2010 | Sillman et al. | |
| 7,843,158 B2 | 11/2010 | Prisco | |
| 7,865,266 B2 | 1/2011 | Moll et al. | |
| 7,865,269 B2 | 1/2011 | Prisco et al. | |
| 7,886,743 B2 | 2/2011 | Cooper et al. | |
| 7,899,578 B2 | 3/2011 | Prisco et al. | |
| 7,907,166 B2 | 3/2011 | Lamprecht et al. | |
| 7,935,130 B2 | 5/2011 | Williams | |
| 7,963,913 B2 | 6/2011 | Devengenzo et al. | |
| 7,983,793 B2 | 7/2011 | Toth et al. | |
| 8,002,767 B2 | 8/2011 | Sanchez | |
| 8,004,229 B2 | 8/2011 | Nowlin et al. | |
| 8,012,170 B2 | 9/2011 | Whitman et al. | |
| 8,054,752 B2 | 11/2011 | Druke et al. | |
| 8,062,288 B2 | 11/2011 | Cooper et al. | |
| 8,075,536 B2 | 12/2011 | Gray et al. | |
| 8,079,950 B2 | 12/2011 | Stern et al. | |
| 8,100,133 B2 | 1/2012 | Mintz et al. | |
| 8,108,072 B2 | 1/2012 | Zhao et al. | |
| 8,120,301 B2 | 2/2012 | Goldberg et al. | |
| 8,142,447 B2 | 3/2012 | Cooper et al. | |
| 8,147,503 B2 | 4/2012 | Zhao et al. | |
| 8,151,661 B2 | 4/2012 | Schena et al. | |
| 8,155,479 B2 | 4/2012 | Hoffman et al. | |
| 8,182,469 B2 | 5/2012 | Anderson et al. | |
| 8,202,278 B2 | 6/2012 | Orban, III et al. | |
| 8,206,406 B2 | 6/2012 | Orban, III | |
| 8,210,413 B2 | 7/2012 | Whitman et al. | |
| 8,216,250 B2 | 7/2012 | Orban, III et al. | |
| 8,220,468 B2 | 7/2012 | Cooper et al. | |
| 8,256,319 B2 | 9/2012 | Cooper et al. | |
| 8,285,517 B2 | 10/2012 | Sillman et al. | |
| 8,315,720 B2 | 11/2012 | Mohr et al. | |
| 8,335,590 B2 | 12/2012 | Costa et al. | |
| 8,347,757 B2 | 1/2013 | Duval | |
| 8,353,493 B2 | 1/2013 | Golden et al. | |
| 8,374,723 B2 | 2/2013 | Zhao et al. | |
| 8,418,073 B2 | 4/2013 | Mohr et al. | |

(56) References Cited

U.S. PATENT DOCUMENTS

| | | |
|---|---|---|
| 8,419,717 B2 | 4/2013 | Diolaiti et al. |
| 8,423,182 B2 | 4/2013 | Robinson et al. |
| 8,452,447 B2 | 5/2013 | Nixon |
| 8,454,585 B2 | 6/2013 | Whitman |
| 8,499,992 B2 | 8/2013 | Whitman et al. |
| 8,508,173 B2 | 8/2013 | Goldberg et al. |
| 8,528,440 B2 | 9/2013 | Morley et al. |
| 8,529,582 B2 | 9/2013 | Devengenzo et al. |
| 8,540,748 B2 | 9/2013 | Murphy et al. |
| 8,551,116 B2 | 10/2013 | Julian et al. |
| 8,562,594 B2 | 10/2013 | Cooper et al. |
| 8,594,841 B2 | 11/2013 | Zhao et al. |
| 8,597,182 B2 | 12/2013 | Stein et al. |
| 8,597,280 B2 | 12/2013 | Cooper et al. |
| 8,600,551 B2 | 12/2013 | Itkowitz et al. |
| 8,608,773 B2 | 12/2013 | Tierney et al. |
| 8,620,473 B2 | 12/2013 | Diolaiti et al. |
| 8,624,537 B2 | 1/2014 | Nowlin et al. |
| 8,634,957 B2 | 1/2014 | Toth et al. |
| 8,638,056 B2 | 1/2014 | Goldberg et al. |
| 8,638,057 B2 | 1/2014 | Goldberg et al. |
| 8,644,988 B2 | 2/2014 | Prisco et al. |
| 8,666,544 B2 | 3/2014 | Moll et al. |
| 8,668,638 B2 | 3/2014 | Donhowe et al. |
| 8,746,252 B2 | 6/2014 | McGrogan et al. |
| 8,749,189 B2 | 6/2014 | Nowlin et al. |
| 8,749,190 B2 | 6/2014 | Nowlin et al. |
| 8,758,352 B2 | 6/2014 | Cooper et al. |
| 8,761,930 B2 | 6/2014 | Nixon |
| 8,768,516 B2 | 7/2014 | Diolaiti et al. |
| 8,786,241 B2 | 7/2014 | Nowlin et al. |
| 8,790,243 B2 | 7/2014 | Cooper et al. |
| 8,808,164 B2 | 8/2014 | Hoffman et al. |
| 8,816,628 B2 | 8/2014 | Nowlin et al. |
| 8,821,480 B2 | 9/2014 | Burbank |
| 8,823,308 B2 | 9/2014 | Nowlin et al. |
| 8,827,989 B2 | 9/2014 | Niemeyer |
| 8,828,023 B2 | 9/2014 | Neff et al. |
| 8,838,270 B2 | 9/2014 | Druke et al. |
| 8,852,174 B2 | 10/2014 | Burbank |
| 8,858,547 B2 | 10/2014 | Brogna |
| 8,862,268 B2 | 10/2014 | Robinson et al. |
| 8,864,751 B2 | 10/2014 | Prisco et al. |
| 8,864,752 B2 | 10/2014 | Diolaiti et al. |
| 8,903,546 B2 | 12/2014 | Diolaiti et al. |
| 8,903,549 B2 | 12/2014 | Itkowitz et al. |
| 8,911,428 B2 | 12/2014 | Cooper et al. |
| 8,912,746 B2 | 12/2014 | Reid et al. |
| 8,944,070 B2 | 2/2015 | Guthart |
| 8,989,903 B2 | 3/2015 | Weir et al. |
| 9,002,518 B2 | 4/2015 | Manzo |
| 9,014,856 B2 | 4/2015 | Manzo et al. |
| 9,016,540 B2 | 4/2015 | Whitman et al. |
| 9,019,345 B2 | 4/2015 | O'Grady et al. |
| 9,043,027 B2 | 5/2015 | Durant et al. |
| 9,050,120 B2 | 6/2015 | Swarup et al. |
| 9,055,961 B2 | 6/2015 | Manzo et al. |
| 9,068,628 B2 | 6/2015 | Solomon et al. |
| 9,078,684 B2 | 7/2015 | Williams |
| 9,084,623 B2 | 7/2015 | Gomez et al. |
| 9,095,362 B2 | 8/2015 | Dachs, II et al. |
| 9,096,033 B2 | 8/2015 | Holop et al. |
| 9,101,381 B2 | 8/2015 | Burbank et al. |
| 9,113,877 B1 | 8/2015 | Whitman et al. |
| 9,138,284 B2 | 9/2015 | Krom et al. |
| 9,144,456 B2 | 9/2015 | Rosa et al. |
| 9,198,730 B2 | 12/2015 | Prisco et al. |
| 9,204,923 B2 | 12/2015 | Manzo et al. |
| 9,226,648 B2 | 1/2016 | Saadat et al. |
| 9,226,750 B2 | 1/2016 | Weir et al. |
| 9,226,761 B2 | 1/2016 | Burbank |
| 9,232,984 B2 | 1/2016 | Guthart et al. |
| 9,241,766 B2 | 1/2016 | Duque et al. |
| 9,241,767 B2 | 1/2016 | Prisco et al. |
| 9,241,769 B2 | 1/2016 | Larkin et al. |
| 9,259,275 B2 | 2/2016 | Burbank |
| 9,259,277 B2 | 2/2016 | Rogers et al. |
| 9,259,281 B2 | 2/2016 | Griffiths et al. |
| 9,259,282 B2 | 2/2016 | Azizian et al. |
| 9,261,172 B2 | 2/2016 | Solomon et al. |
| 9,265,567 B2 | 2/2016 | Orban, III et al. |
| 9,265,584 B2 | 2/2016 | Itkowitz et al. |
| 9,283,049 B2 | 3/2016 | Diolaiti et al. |
| 9,295,524 B2 | 3/2016 | Schena et al. |
| 9,301,811 B2 | 4/2016 | Goldberg et al. |
| 9,314,307 B2 | 4/2016 | Richmond et al. |
| 9,317,651 B2 | 4/2016 | Nixon |
| 9,345,546 B2 | 5/2016 | Toth et al. |
| 9,393,017 B2 | 7/2016 | Flanagan et al. |
| 9,402,689 B2 | 8/2016 | Prisco et al. |
| 9,417,621 B2 | 8/2016 | Diolaiti |
| 9,424,303 B2 | 8/2016 | Hoffman et al. |
| 9,433,418 B2 | 9/2016 | Whitman et al. |
| 9,446,517 B2 | 9/2016 | Burns et al. |
| 9,452,020 B2 | 9/2016 | Griffiths et al. |
| 9,474,569 B2 | 10/2016 | Manzo et al. |
| 9,480,533 B2 | 11/2016 | Devengenzo et al. |
| 9,503,713 B2 | 11/2016 | Zhao et al. |
| 9,550,300 B2 | 1/2017 | Danitz et al. |
| 9,554,859 B2 | 1/2017 | Nowlin et al. |
| 9,566,124 B2 | 2/2017 | Prisco et al. |
| 9,579,164 B2 | 2/2017 | Itkowitz et al. |
| 9,585,641 B2 | 3/2017 | Cooper et al. |
| 9,615,883 B2 | 4/2017 | Schena et al. |
| 9,623,563 B2 | 4/2017 | Nixon |
| 9,623,902 B2 | 4/2017 | Griffiths et al. |
| 9,629,520 B2 | 4/2017 | Diolaiti |
| 9,662,177 B2 | 5/2017 | Weir et al. |
| 9,664,262 B2 | 5/2017 | Donlon et al. |
| 9,687,312 B2 | 6/2017 | Dachs, II et al. |
| 9,700,334 B2 | 7/2017 | Hinman et al. |
| 9,718,190 B2 | 8/2017 | Larkin et al. |
| 9,730,719 B2 | 8/2017 | Brisson et al. |
| 9,737,199 B2 | 8/2017 | Pistor et al. |
| 9,795,446 B2 | 10/2017 | DiMaio et al. |
| 9,797,484 B2 | 10/2017 | Solomon et al. |
| 9,801,690 B2 | 10/2017 | Larkin et al. |
| 9,814,530 B2 | 11/2017 | Weir et al. |
| 9,814,536 B2 | 11/2017 | Goldberg et al. |
| 9,814,537 B2 | 11/2017 | Itkowitz et al. |
| 9,820,823 B2 | 11/2017 | Richmond et al. |
| 9,827,059 B2 | 11/2017 | Robinson et al. |
| 9,830,371 B2 | 11/2017 | Hoffman et al. |
| 9,839,481 B2 | 12/2017 | Blumenkranz et al. |
| 9,839,487 B2 | 12/2017 | Dachs, II |
| 9,850,994 B2 | 12/2017 | Schena |
| 9,855,102 B2 | 1/2018 | Blumenkranz |
| 9,855,107 B2 | 1/2018 | Labonville et al. |
| 9,872,737 B2 | 1/2018 | Nixon |
| 9,877,718 B2 | 1/2018 | Weir et al. |
| 9,883,920 B2 | 2/2018 | Blumenkranz |
| 9,888,974 B2 | 2/2018 | Niemeyer |
| 9,895,813 B2 | 2/2018 | Blumenkranz et al. |
| 9,901,408 B2 | 2/2018 | Larkin |
| 9,918,800 B2 | 3/2018 | Itkowitz et al. |
| 9,943,375 B2 | 4/2018 | Blumenkranz et al. |
| 9,948,852 B2 | 4/2018 | Lilagan et al. |
| 9,949,798 B2 | 4/2018 | Weir |
| 9,949,802 B2 | 4/2018 | Cooper |
| 9,952,107 B2 | 4/2018 | Blumenkranz et al. |
| 9,956,044 B2 | 5/2018 | Gomez et al. |
| 9,980,778 B2 | 5/2018 | Ohline et al. |
| 10,008,017 B2 | 6/2018 | Itkowitz et al. |
| 10,028,793 B2 | 7/2018 | Griffiths et al. |
| 10,033,308 B2 | 7/2018 | Chaghajerdi et al. |
| 10,034,719 B2 | 7/2018 | Richmond et al. |
| 10,052,167 B2 | 8/2018 | Au et al. |
| 10,085,811 B2 | 10/2018 | Weir et al. |
| 10,092,344 B2 | 10/2018 | Mohr et al. |
| 10,123,844 B2 | 11/2018 | Nowlin |
| 10,188,471 B2 | 1/2019 | Brisson |
| 10,201,390 B2 | 2/2019 | Swarup et al. |
| 10,213,202 B2 | 2/2019 | Flanagan et al. |
| 10,258,416 B2 | 4/2019 | Mintz et al. |

(56) References Cited

U.S. PATENT DOCUMENTS

| | | |
|---|---|---|
| 10,278,782 B2 | 5/2019 | Jarc et al. |
| 10,278,783 B2 | 5/2019 | Itkowitz et al. |
| 10,282,881 B2 | 5/2019 | Itkowitz et al. |
| 10,335,242 B2 | 7/2019 | Devengenzo et al. |
| 10,405,934 B2 | 9/2019 | Prisco et al. |
| 10,433,922 B2 | 10/2019 | Itkowitz et al. |
| 10,464,219 B2 | 11/2019 | Robinson et al. |
| 10,485,621 B2 | 11/2019 | Morrissette et al. |
| 10,500,004 B2 | 12/2019 | Hanuschik et al. |
| 10,500,005 B2 | 12/2019 | Weir et al. |
| 10,500,007 B2 | 12/2019 | Richmond et al. |
| 10,507,066 B2 | 12/2019 | DiMaio et al. |
| 10,510,267 B2 | 12/2019 | Jarc et al. |
| 10,524,871 B2 | 1/2020 | Liao |
| 10,548,459 B2 | 2/2020 | Itkowitz et al. |
| 10,575,909 B2 | 3/2020 | Robinson et al. |
| 10,592,529 B2 | 3/2020 | Hoffman et al. |
| 10,595,946 B2 | 3/2020 | Nixon |
| 10,881,469 B2 | 1/2021 | Robinson |
| 10,881,473 B2 | 1/2021 | Itkowitz et al. |
| 10,898,188 B2 | 1/2021 | Burbank |
| 10,898,189 B2 | 1/2021 | McDonald, II |
| 10,905,506 B2 | 2/2021 | Itkowitz et al. |
| 10,912,544 B2 | 2/2021 | Brisson et al. |
| 10,912,619 B2 | 2/2021 | Jarc et al. |
| 10,918,387 B2 | 2/2021 | Duque et al. |
| 10,918,449 B2 | 2/2021 | Solomon et al. |
| 10,932,873 B2 | 3/2021 | Griffiths et al. |
| 10,932,877 B2 | 3/2021 | Devengenzo et al. |
| 10,939,969 B2 | 3/2021 | Swarup et al. |
| 10,939,973 B2 | 3/2021 | DiMaio et al. |
| 10,952,801 B2 | 3/2021 | Miller et al. |
| 10,965,933 B2 | 3/2021 | Jarc |
| 10,966,742 B2 | 4/2021 | Rosa et al. |
| 10,973,517 B2 | 4/2021 | Wixey |
| 10,973,519 B2 | 4/2021 | Weir et al. |
| 10,984,567 B2 | 4/2021 | Itkowitz et al. |
| 10,993,773 B2 | 5/2021 | Cooper et al. |
| 10,993,775 B2 | 5/2021 | Cooper et al. |
| 11,000,331 B2 | 5/2021 | Krom et al. |
| 11,013,567 B2 | 5/2021 | Wu et al. |
| 11,020,138 B2 | 6/2021 | Ragosta |
| 11,020,191 B2 | 6/2021 | Diolaiti et al. |
| 11,020,193 B2 | 6/2021 | Wixey et al. |
| 11,026,755 B2 | 6/2021 | Weir et al. |
| 11,026,759 B2 | 6/2021 | Donlon et al. |
| 11,040,189 B2 | 6/2021 | Vaders et al. |
| 11,045,077 B2 | 6/2021 | Stern et al. |
| 11,045,274 B2 | 6/2021 | Dachs, II et al. |
| 11,058,501 B2 | 7/2021 | Tokarchuk et al. |
| 11,076,925 B2 | 8/2021 | DiMaio et al. |
| 11,090,119 B2 | 8/2021 | Burbank |
| 11,096,687 B2 | 8/2021 | Flanagan et al. |
| 11,098,803 B2 | 8/2021 | Duque et al. |
| 11,109,925 B2 | 9/2021 | Cooper et al. |
| 11,116,578 B2 | 9/2021 | Hoffman et al. |
| 11,129,683 B2 | 9/2021 | Steger et al. |
| 11,135,029 B2 | 10/2021 | Suresh et al. |
| 11,147,552 B2 | 10/2021 | Burbank et al. |
| 11,147,640 B2 | 10/2021 | Jarc et al. |
| 11,154,373 B2 | 10/2021 | Abbott et al. |
| 11,154,374 B2 | 10/2021 | Hanuschik et al. |
| 11,160,622 B2 | 11/2021 | Goldberg et al. |
| 11,160,625 B2 | 11/2021 | Wixey et al. |
| 11,161,243 B2 | 11/2021 | Rabindran et al. |
| 11,166,758 B2 | 11/2021 | Mohr et al. |
| 11,166,770 B2 | 11/2021 | DiMaio et al. |
| 11,166,773 B2 | 11/2021 | Ragosta et al. |
| 11,173,597 B2 | 11/2021 | Rabindran et al. |
| 11,185,378 B2 | 11/2021 | Weir et al. |
| 11,191,596 B2 | 12/2021 | Thompson et al. |
| 11,197,729 B2 | 12/2021 | Thompson et al. |
| 11,213,360 B2 | 1/2022 | Hourtash et al. |
| 11,221,863 B2 | 1/2022 | Azizian et al. |
| 11,234,700 B2 | 2/2022 | Ragosta et al. |
| 11,241,274 B2 | 2/2022 | Vaders et al. |
| 11,241,290 B2 | 2/2022 | Waterbury et al. |
| 11,259,870 B2 | 3/2022 | DiMaio et al. |
| 11,259,884 B2 | 3/2022 | Burbank |
| 11,272,993 B2 | 3/2022 | Gomez et al. |
| 11,272,994 B2 | 3/2022 | Saraliev et al. |
| 11,291,442 B2 | 4/2022 | Wixey et al. |
| 11,291,513 B2 | 4/2022 | Manzo et al. |
| 2007/0088277 A1* | 4/2007 | McGinley .......... A61B 17/3423 604/167.01 |
| 2009/0248038 A1 | 10/2009 | Blumenkranz et al. |
| 2011/0071541 A1 | 3/2011 | Prisco et al. |
| 2016/0220320 A1* | 8/2016 | Crawford ............... A61B 90/98 |
| 2017/0086930 A1* | 3/2017 | Thompson ......... A61B 17/3476 |
| 2018/0168689 A1* | 6/2018 | Beckman ........... A61B 17/3421 |
| 2018/0177557 A1 | 6/2018 | Kapadia et al. |
| 2018/0235724 A1 | 8/2018 | Nowatschin et al. |
| 2018/0289445 A1 | 10/2018 | Krinninger et al. |

FOREIGN PATENT DOCUMENTS

| WO | 2008098124 A1 | 8/2008 | |
| WO | 2014127984 A1 | 8/2014 | |
| WO | 2015088647 A1 | 6/2015 | |
| WO | 2015142814 A1 | 9/2015 | |
| WO | 2016075241 A1 | 5/2016 | |
| WO | 2016100181 A1 | 6/2016 | |
| WO | 2016200722 A1 | 12/2016 | |
| WO | WO-2016200722 A1 * | 12/2016 | ............. A61B 17/00 |

OTHER PUBLICATIONS

U.S. Appl. No. 62/341,714, filed May 26, 2016, entitled "Robotic Surgical Assemblies,".

Australian Examination Report No. 1 dated Oct. 1, 2020 corresponding to counterpart Patent Application AU 2019205201.

Japanese Office Action dated Jun. 25, 2021 corresponding to counterpart Patent Application JP 2020-536980.

Extended European Search Report dated Sep. 15, 2021 corresponding to counterpart Patent Application EP 19736126.4.

Australian Examination Report No. 1 issued in corresponding application 2020260412 dated Nov. 24, 2021 (2 pages).

Japanese Office Action issued in corresponding application JP 2020-536980 dated Jan. 5, 2022, together with English language translation (6 pages).

* cited by examiner

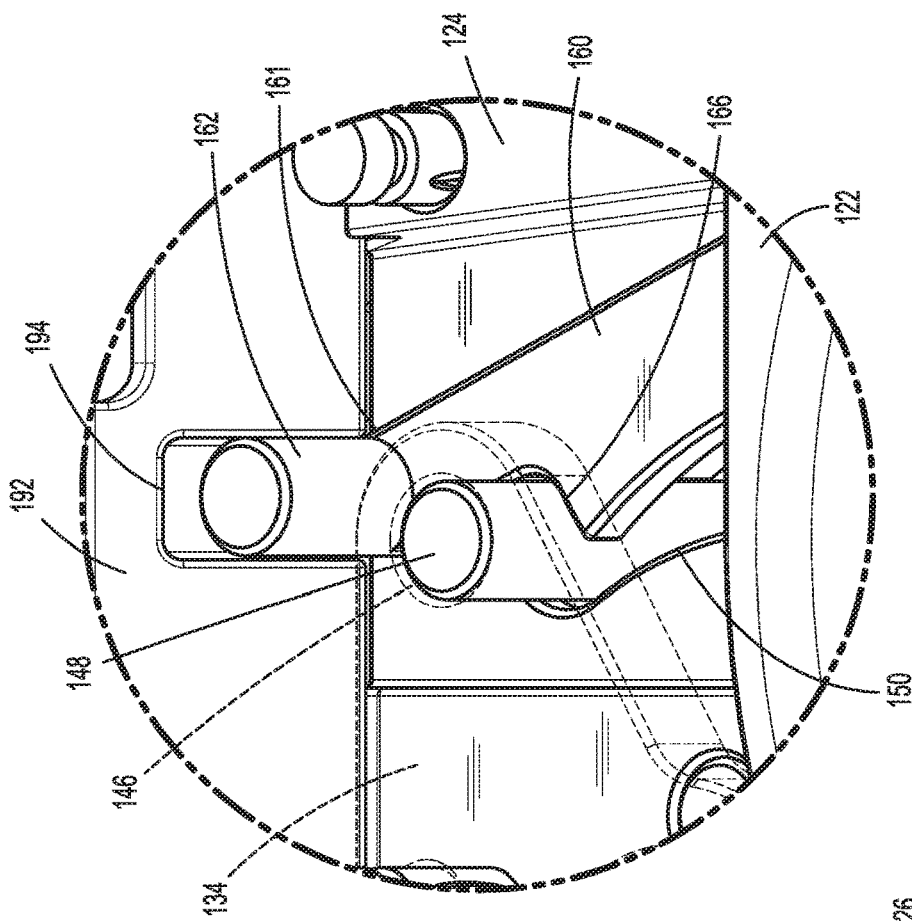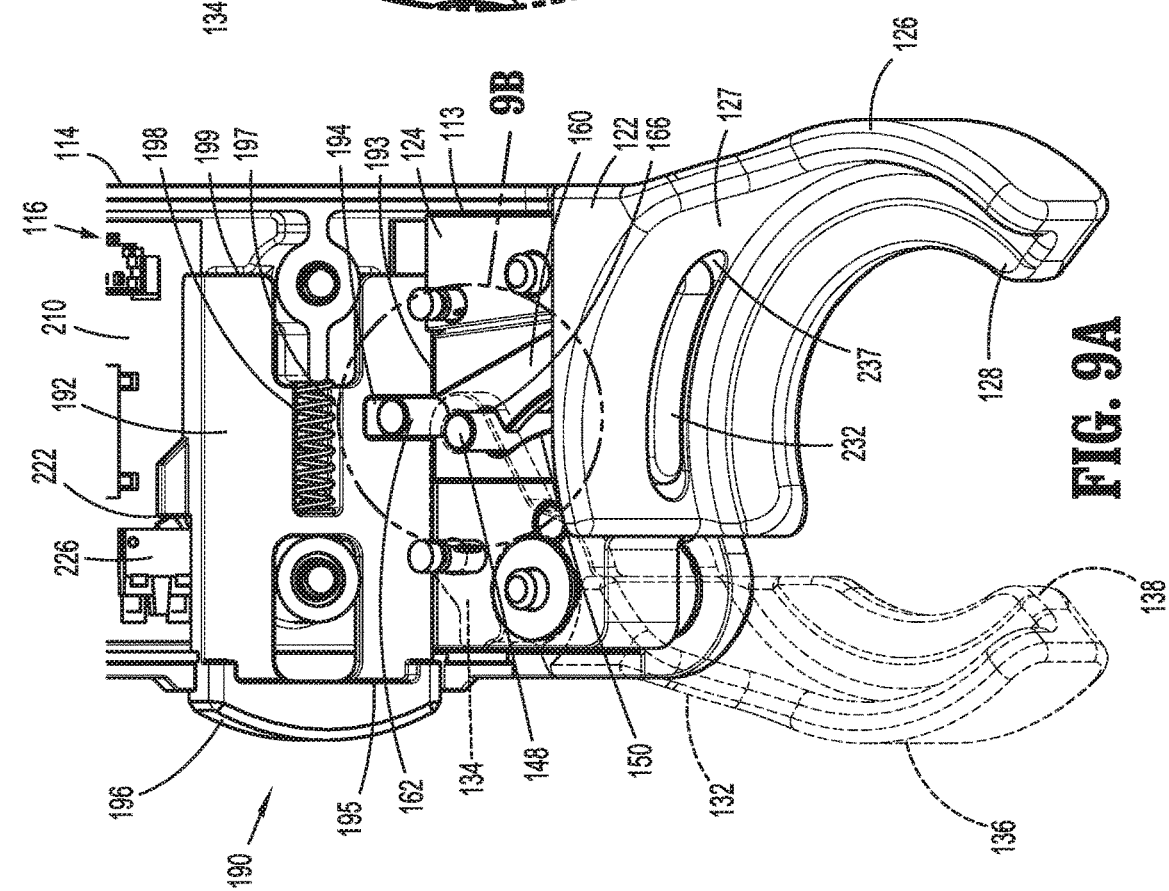

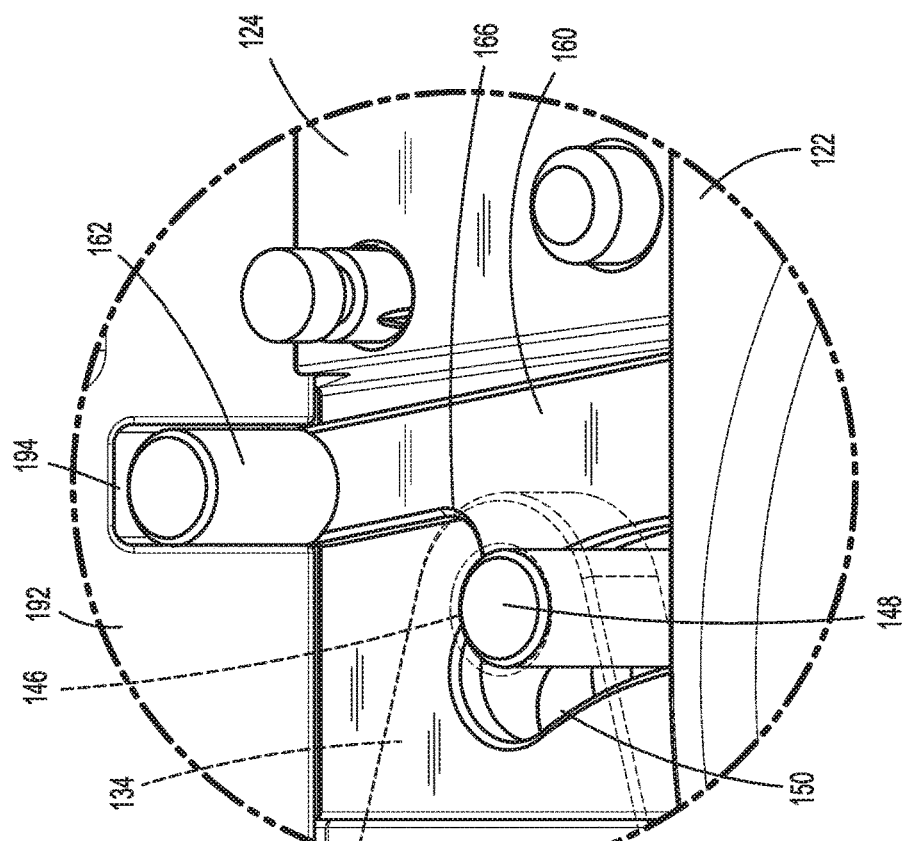
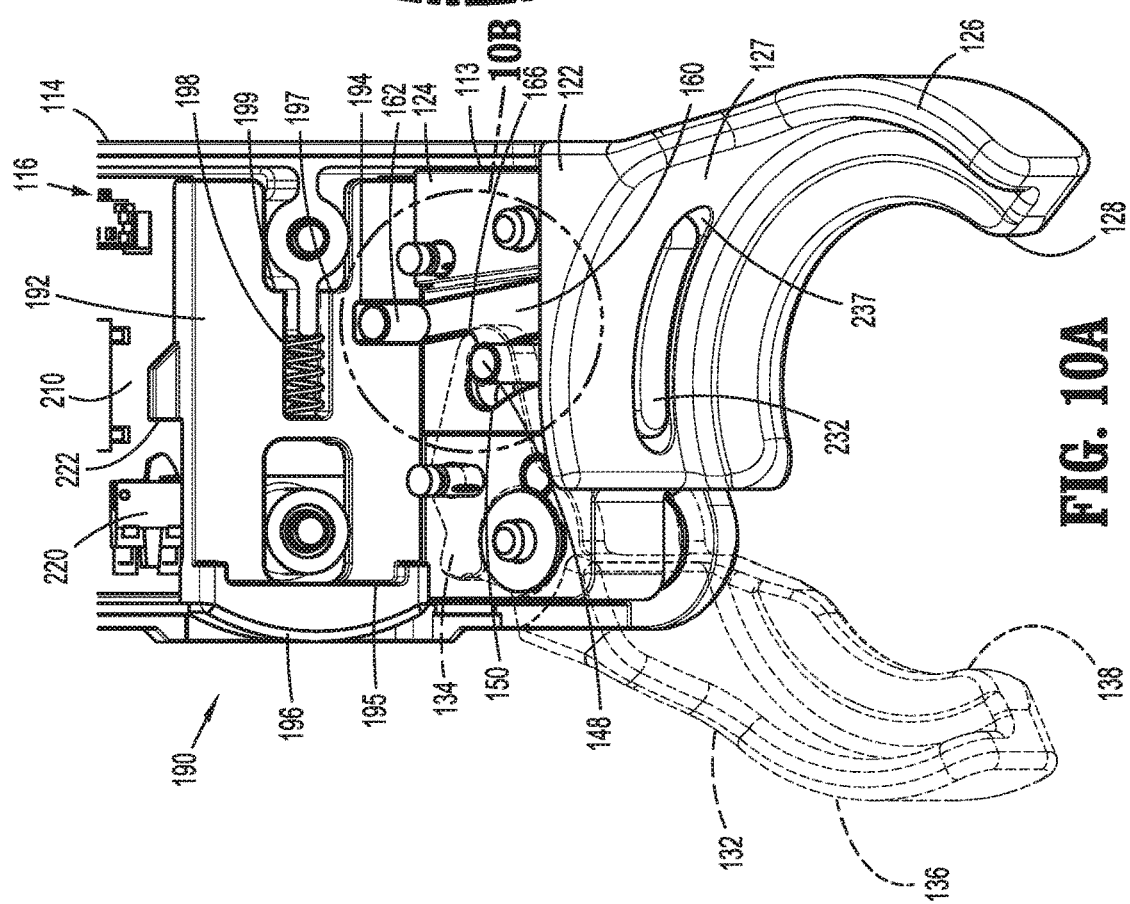
FIG. 10B
FIG. 10A

SYSTEMS AND ASSEMBLIES FOR MOUNTING A SURGICAL ACCESSORY TO ROBOTIC SURGICAL SYSTEMS, AND PROVIDING ACCESS THERETHROUGH

CROSS-REFERENCE TO RELATED APPLICATIONS

This application is a U.S. National Stage Application filed under 35 U.S.C. § 371(a) of International Patent Application Serial No. PCT/US2019/012045, filed Jan. 2, 2019, which claims the benefit of and priority to U.S. Provisional Patent Application Ser. No. 62/613,601, filed Jan. 4, 2018, the entire disclosure of which is incorporated by reference herein.

BACKGROUND

Robotic surgical systems have been used in minimally invasive medical procedures. Some robotic surgical systems include a robot arm having an instrument drive assembly coupled thereto for coupling surgical instruments to the robot arm, such as, for example, a pair of jaw members, electrosurgical forceps, cutting instruments, or any other endoscopic or open surgical devices, and a mount assembly coupled thereto for coupling surgical accessories to the robot arm, such as, for example, a trocar or surgical port (hereinafter "surgical port"), an optical device, or the like.

Prior to or during use of the robotic system, surgical instruments are selected and connected to the instrument drive assembly of each robot arm, where the instrument drive assembly can drive the actuation of an end effector of the surgical instrument. Under certain procedures, a surgical accessory, such as, for example, an optical device or a surgical port may be coupled to the robot arm via the mount assembly of the robot arm. During a procedure, the end effector and/or a portion of the surgical instrument may be inserted through the surgical port, and a small incision or a natural orifice of a patient, to bring the end effector proximate a working site within the body of the patient. Such surgical ports may provide additional stability, and act as a guide channel, for the surgical instrument during insertion and actuation of the end effector.

Accordingly, there is a need for a mount assembly which provides quick and easy connection between the robot arm and a variety of surgical accessories, such as a surgical port or optical device.

SUMMARY

The present disclosure relates to mount assemblies and access devices for surgical robotic systems.

According to an aspect of the present disclosure, a mount assembly for use with a robotic system is provided. The mount assembly includes a housing configured to couple to a robot arm of a robotic system; a coupling assembly supported by the housing and including a first arm and a second arm, the coupling assembly transitionable between open and closed configurations, wherein in the open configuration first and second arms pivot into a relatively more spaced apart relation with respect to one another, and in the closed configuration first and second arms pivot into a relatively more approximated relation with respect to one another. In the closed configuration the first and second arms are configured to secure a surgical port to the robot arm. A release assembly is supported by the housing and is engagable with the coupling assembly, the release assembly transitions between a locked configuration and an unlocked configuration with respect to the coupling assembly. In the locked configuration of the release assembly the first and second arms of the coupling assembly are fixed in the closed configuration. A communication assembly is supported by the housing and is configured for communication with the robotic system with respect to a status of the coupling assembly corresponding to the open and closed configuration thereof and to a status of the release assembly corresponding to the locked and unlocked configuration thereof.

The communication assembly may include a release assembly sensor switch configured for selective engagement with the release assembly. Thus, when the release assembly transitions to the locked configuration the release assembly sensor switch is engaged. The communication assembly may also include a button pivotably disposed within a cavity of the second arm of the coupling assembly, the button configured for engagement by a surgical port secured between first and second arms of the coupling assembly. The communication assembly may include a presence sensor switch configured for selective engagement with the button, wherein when the button is engaged by the surgical port the button pivots into engagement with the presence sensor switch.

The mount assembly may further include a latch plate coupled between the release assembly and the coupling assembly. In the locked configuration of the release assembly the latch plate may be positioned for engagement with a portion of the first arm of the coupling assembly. In the unlocked configuration of the release assembly the latch plate may be positioned for disengagement with the portion of the first arm of the coupling assembly.

The coupling assembly may include a biasing member coupled between the first and second arms, the biasing member configured to bias the coupling assembly into one of the open or closed configurations.

The first arm of the coupling assembly may be pivotably coupled to a portion of the second arm, and the second arm may be fixedly supported by the housing.

The first and second arms may be pivotably coupled to the housing.

The release assembly may include a biasing member configured to bias the release assembly into one of the locked or unlocked configurations.

The release assembly may include a first actuation lever coupled to the first arm of the coupling assembly and a second actuation lever coupled to the second arm of the coupling assembly. The first and second actuation levers may be configured to transition the first and second arms of the coupling assembly between the open and closed configurations, and the locked and unlocked configurations.

Each of the first and second arms may include an engagement region thereon configured to engage a surgical port while in the closed configuration of the coupling assembly. The engagement regions of the first and second arms may define a complementary shape with respect to an outer surface of a surgical port.

Each of the engagement regions may define an inner surface and may include a flange extending therefrom. The flange may be configured to engage a portion of a surgical port while in the closed configuration of the coupling assembly.

According to a further aspect of the present disclosure, a robotic system is provided and includes a surgical port configured to receive a surgical instrument therethrough. The surgical port includes a seal housing having an engagement region disposed about an external radial surface thereof; a seal cover having a plurality of lobes radially disposed along a distal portion thereof, each lobe of the plurality of lobes including a key feature thereon and a cannula assembly having a plurality of key features radially disposed along a proximal portion thereof. Each respective key feature of the cannula assembly corresponding to, and configured to engage with, a key feature of a respective lobe of the plurality of lobes of the seal cover. The surgical port further includes a central lumen defined by an inner surface of each of the seal housing, the seal cover, and the cannula assembly. A seal assembly is coupled between the seal housing and the seal cover and a cannula seal is coupled between the seal cover and the cannula assembly. The seal assembly and the cannula seal are configured to maintain a fluidic seal within the central lumen of the surgical port.

The robotic system further includes a mount assembly configured to couple to a robot arm of the robotic system. The mount assembly includes a coupling assembly including a first arm and a second arm, the coupling assembly transitionable between open and closed configurations. In the open configuration first and second arms pivot into relatively more spaced relation with respect to one another. In the closed configuration first and second arms pivot into a relatively more approximated relation with respect to one another. In the closed configuration the first and second arms selectively secure the engagement region of the seal housing of the surgical port therebetween. A release assembly is engaged with the coupling assembly and is transitionable between a locked configuration and an unlocked configuration with respect to the coupling assembly. In the locked configuration of the release assembly the first and second arms of the coupling assembly are pivotably fixed in the closed configuration.

The mount assembly may further include a communication assembly configured for communication with the robotic system with respect to a status of the coupling assembly corresponding to the open and closed configuration thereof; and a status of the release assembly corresponding to the locked and unlocked configuration thereof.

BRIEF DESCRIPTION OF THE DRAWINGS

Embodiments of the present disclosure are described herein with reference to the accompanying drawings, wherein:

FIG. 9A is a front perspective view of the coupling assembly of FIG. 6, in a closed configuration, with the movable arm of FIG. 7 shown in phantom;

FIG. 9B is a front perspective view of the area of detail of FIG. 9A, with a latch plate of the coupling assembly of FIG. 6 in an engaged position;

FIG. 10A is a front perspective view of the coupling assembly of FIG. 6, in an open configuration, with the movable arm of FIG. 7 shown in phantom;

FIG. 10B is a front perspective view of the area of detail of FIG. 10A, with the latch plate of the coupling assembly of FIG. 6 in a disengaged position;

DETAILED DESCRIPTION

Figure 1A:
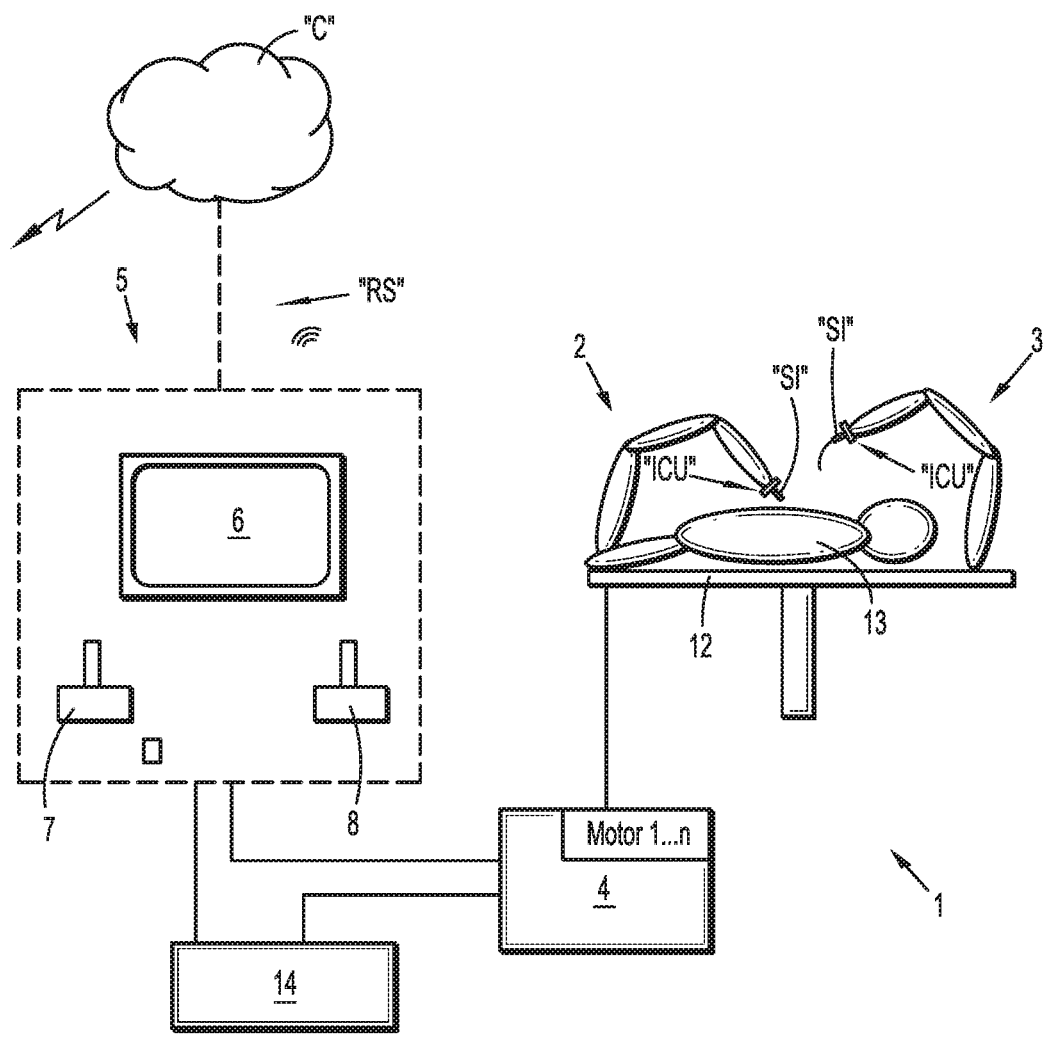
FIG. 1A is a schematic illustration of a medical work station and an operating console in accordance with the present disclosure.

Embodiments of the presently disclosed mount assembly and surgical port are described in detail with reference to the drawings, in which like reference numerals designate identical or corresponding elements in each of the several views. As is used in the art, the term "distal" refers to a position of an instrument, or portion thereof, which is farther from the user, and the term "proximal" refers to a position of an instrument, or portion thereof, which is closer to the user.

Figure 1B:
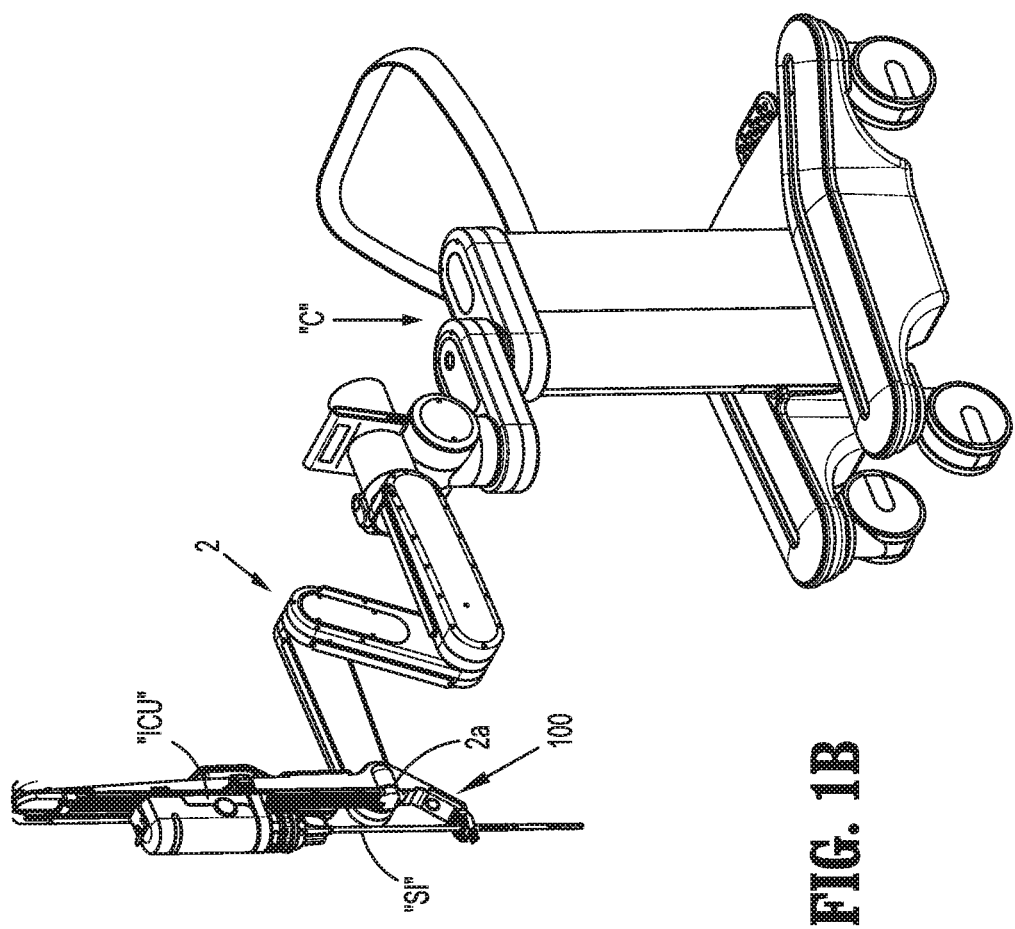
FIG. 1B is an exemplary illustration of a cart supporting a robot arm of the medical work station of FIG. 1A, the robot arm supporting a mount assembly and a surgical part at a distal end thereof.

Referring initially to FIGS. 1A and 1B, a medical work station is shown generally as work station 1 and generally includes a plurality of robot arms 2, 3; a control device 4; and an operating console 5 coupled with control device 4. Operating console 5 includes a display device 6, which is set up in particular to display three-dimensional images; and manual input devices 7, 8, by means of which a person (not shown), for example a surgeon, is able to telemanipulate robot arms 2, 3 in a first operating mode, as known in principle to a person skilled in the art.

Each of the robot arms 2, 3 may be supported by a respective cart "C", and may include a plurality of members, which are connected through joints, and an instrument control unit "ICU", to which may be attached, for example, an instrument drive assembly of a surgical instrument "SI", the surgical instrument "SI" supporting an end effector (not shown) including, for example, a pair of jaw members, electrosurgical forceps, cutting instruments, or any other endoscopic or open surgical devices. For a detailed discussion and illustrative examples of the construction and operation of an end effector for use with instrument control unit "ICU", reference may be made to commonly owned International Patent Application No. PCT/US14/61329, filed on Oct. 20, 2014, and entitled "Wrist and Jaw Assemblies for Robotic Surgical Systems," and U.S. Provisional Patent Application No. 62/341,714, filed on May 26, 2016, entitled "Robotic Surgical Assemblies," the entire content of each of which being incorporated herein by reference.

Robot arms 2, 3 may be driven by electric drives (not shown) that are connected to control device 4. Control device 4 (e.g., a computer) is set up to activate the drives, in particular by means of a computer program, in such a way that robot arms 2, 3, instrument control units "ICU", and thus the surgical instruments "SI" execute a desired movement or articulation according to a movement defined by means of manual input devices 7, 8. Control device 4 may also be set up in such a way that it regulates the movement of robot arms 2, 3 and/or of the drives.

Medical work station 1 is configured for use on a patient 13 lying on a patient table 12 to be treated in an open surgery, or a minimally invasive manner, by means of surgical instrument "SI". Medical work station 1 may also include more than two robot arms 2, 3, the additional robot arms likewise being connected to control device 4 and being telemanipulatable by means of operating console 5. An instrument control unit and a surgical instrument may also be attached to the additional robot arm. Medical work station 1 may include a database 14, in particular coupled to or with control device 4, in which pre-operative data from patient 13 and/or anatomical atlases, for example, may be stored.

For a detailed discussion of the construction and operation of medical work station 1 reference may be made to U.S. Pat. No. 8,828,023, filed on Nov. 3, 2011 and entitled "Medical Workstation," the entire content of which is incorporated herein by reference.

Control device 4 may control a plurality of motors (e.g., "M1"-"M6"). Motors "M" may be part of instrument control unit "ICU" and/or disposed externally of instrument control unit "ICU". In use, as motors "M" are driven, movement and/or articulation of the instrument drive assembly of surgical instrument "SI", and an end effector attached thereto, is controlled. It is further envisioned that at least one motor "M" receives signals wirelessly (e.g., from control device 4). It is contemplated that control device 4 coordinates the activation of the various motors (Motor 1 . . . n) to coordinate an operation, movement, and/or articulation of robot arms 2, 3 and/or surgical instrument "SI". It is envisioned that each motor may correspond to a separate degree of freedom of robot arms 2, 3, and/or surgical instrument "SI" engaged with instrument control unit "ICU". It is further envisioned that more than one motor, including every motor (Motor 1 . . . n), is used for each degree of freedom.

With continued reference to FIG. 1B, robot arm 2 may include a mount assembly coupled at a distal portion 2a of robot arm 2, whereby it should be appreciated that any of robot arms 2, 3 may alternatively or additionally include a respective mount assembly coupled thereto. As discussed herein, the mount assembly is configured to releasably couple a surgical accessory to robot arm 2. It should be appreciated that the mount assembly may be configured to releasably couple a variety of surgical accessories to robot arm 2, such as, for example a trocar, a surgical port, an optical device, or the like. For the sake of brevity, the mount assembly will be discussed herein with respect to a surgical port. It should be appreciated that if utilized with a surgical port, the mount assembly adds to the stability to a surgical instrument passed therethrough. During a surgical procedure, surgical instruments may undergo undesired reaction loading as a result of forces exerted upon the surgical instrument by a natural orifice or the surrounding tissue of an incision, such as, for example, an incision through an abdominal wall. By utilizing the mount assembly and a surgical port, the mount assembly will assist in inhibiting the transfer of such forces upon the surgical instrument minimizing instrument deflection.

With references to FIGS. 2-12B, an embodiment of a mount assembly will be described with reference to a mount assembly 100 which includes a housing 110, a coupling assembly 120, and a release assembly 190 (FIGS. 4-5 and 9A-10B). Housing 110 includes a first half 112 releasably coupled to a second half 114 such that, when coupled to one another, a cavity 116 is defined therebetween. A proximal portion 111 of first half 112 of housing 110 is releasably couplable to distal portion 2a of robot arm 2, such that mount assembly 100 is thereby releasably coupled to robot arm 2. Coupling assembly 120 is supported by a distal portion 113 of second half 114 of housing 110, disposed within cavity 116, and extends distally from a distal portion 115 of cavity 116. Release assembly 190 is supported by housing 110, is disposed within cavity 116, and extends therefrom through an opening 117 defined by first and second halves 112, 114 of housing 110.

With reference to FIGS. 4-8, coupling assembly 120 is configured to releasably engage a surgical port 1000 (FIGS. 16-21). Coupling assembly 120 is transitionable between a closed configuration (FIG. 9A), for engagement with the surgical port 1000, and an open configuration (FIG. 10A), for disengagement with surgical port 1000, such that the surgical port 1000 is releasably secured to robot arm 2. Coupling assembly 120 includes a fixed arm 122, a movable arm 132, and a latch plate 160. Fixed arm 122 includes a support portion 124 configured to reside within distal portion 113 of second half 114 of housing 110, and an engagement portion 126 extending distally therefrom. Movable arm 132 includes a support portion 134 configured to reside within distal portion 113 of second half 114 of housing 110, and an engagement portion 136 extending distally therefrom. It is envisioned that engagement portions 126, 136 of fixed and movable arms 122, 132 define a complementary shape with respect to an outer surface of surgical port 1000, as discussed herein, or any alternative surgical accessory which may be coupled to robot arm 2 via coupling assembly 120 of mount assembly 100. As an exemplary illustration, engagement portions 126, 136 may define generally arcuate inner surfaces 127, 137, respectively, such that a surgical port defining a generally circular outer profile may be received between fixed and movable arm 122, 132, in a clamping fashion, and come into abutment with engagement portions 126, 136. Engagement portions 126, 136 may further include a flange 128, 138 extending therefrom, respectively, which is configured to engage a portion of surgical port 1000 positioned between fixed and movable arms 122, 132, as discussed further below, such that linear translation of surgical port 1000, with respect to fixed and movable arms 122, 132, is thereby inhibited.

Figure 6:
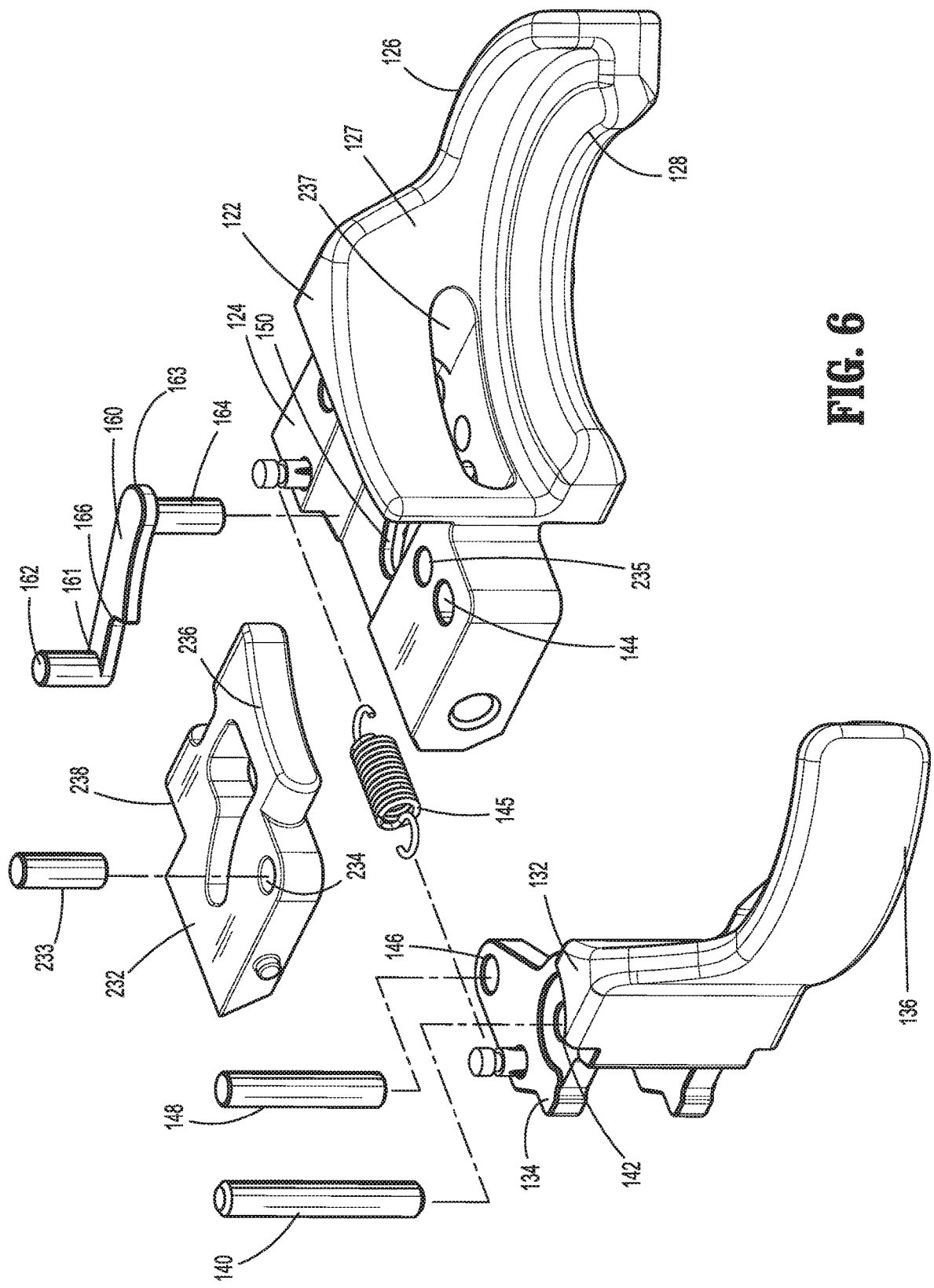
FIG. 6 is a perspective view of an embodiment of a coupling assembly in accordance with the present disclosure of the mount assembly of FIG. 2, with parts separated.
Figure 7:
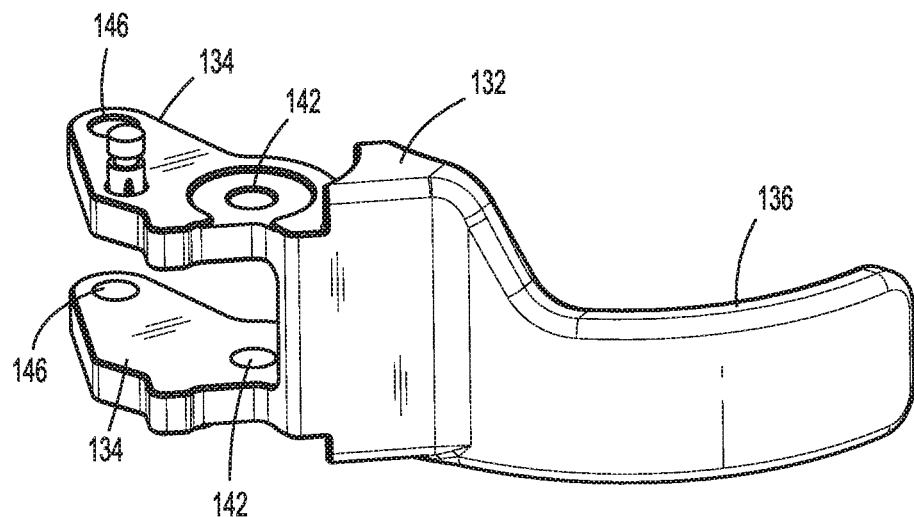
FIG. 7 is a side perspective view of a movable arm of the coupling assembly of FIG. 6.
Figure 8:
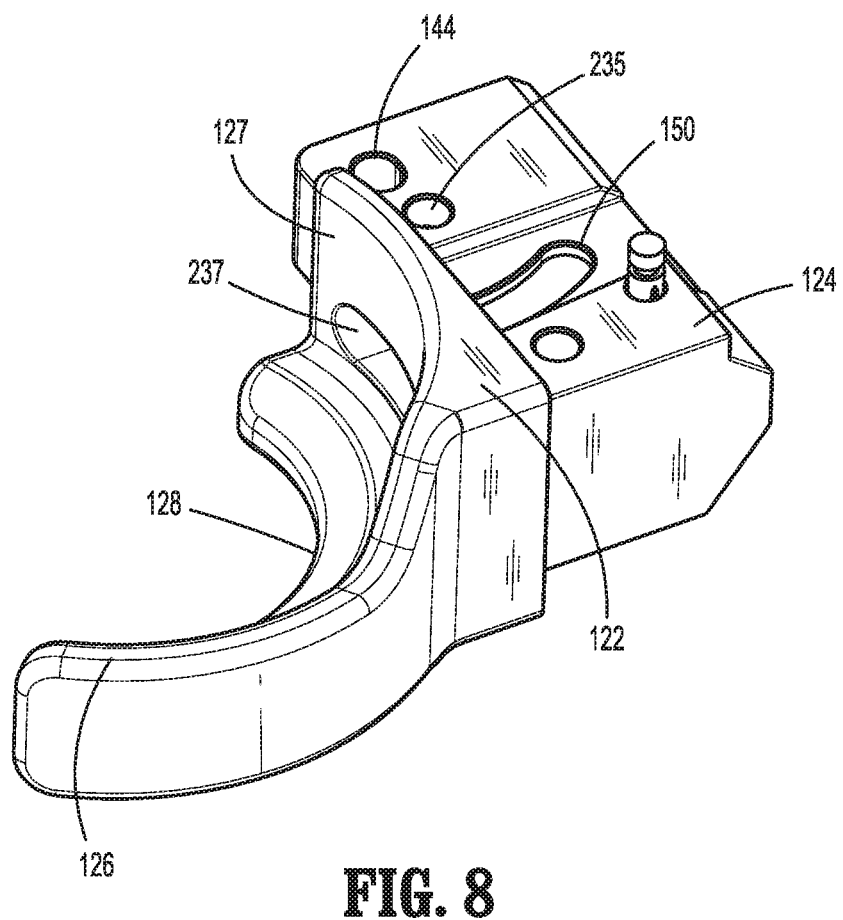
FIG. 8 is a side perspective view of a fixed arm of the coupling assembly of FIG. 6.

With continued reference to FIGS. 6-8, support portion 134 of movable arm 132 is pivotably coupled to support portion 124 of fixed arm 122. Movable arm 132 includes a pivot bore 142 defined through support portion 134 thereof. Fixed arm 122 includes a bore 144 defined through support portion 124 thereof. A pivot pin 140 is disposed within pivot bore 142 defined through support portion 134 of movable arm 132, and within bore 144 defined through support portion 124 of fixed arm 122, and thus pivotably couples movable arm 132 to fixed arm 122 about pivot pin 140, pivot bore 142, and bore 144. As movable arm 132 pivots about pivot pin 140 engagement portion 136 of movable arm 132 is caused to transition between a position proximate engagement portion 126 of fixed arm 122, which corresponds to the closed configuration of coupling assembly 120 (FIG. 9A), and a position spaced away from engagement portion 126 of fixed arm 122, which corresponds to the open configuration of coupling assembly 120 (FIG. 10A).

With reference to FIGS. 9A and 10A, the transition of coupling assembly 120 between the closed and open configurations will be further discussed. It should be appreciated that through pivoting of movable arm 132, coupling assembly 120 is caused to transition between the closed configuration (FIG. 9A) and the open configuration (FIG. 10A). In the closed configuration of coupling assembly 120, engagement portion 136 of movable arm 132 is proximate engagement portion 126 of fixed arm 122 to achieve fixation of surgical port 1000 to robot arm 2, via coupling assembly 120 of mount assembly 100. In the open configuration of coupling assembly 120, engagement portion 136 of movable arm 132 is spaced away from engagement portion 126 of fixed arm 122 to receive or release surgical port 1000 therefrom. Thus, in the closed configuration of coupling assembly 120, surgical port 1000 is secured to robot arm 2, and in the open configuration of clamping assembly 120, surgical port 1000 is unsecured from robot arm 2.

Coupling assembly 120 may further include a biasing member 145 (FIGS. 5 and 6) coupled between support portion 134 of movable arm 132 and support portion 124 of fixed arm 122, such that engagement portion 136 of movable arm 132 is biased into a position proximate to, or spaced away from, engagement portion 126 of fixed arm 122. Accordingly, biasing member 145 acts to bias coupling assembly 120 into one of the closed or open configurations.

With continued reference to FIGS. 6 and 9A-10B, movable arm 132 further includes a latch pin bore 146 defined through support portion 134 thereof, and fixed arm 122 further includes a cam slot 150 defined through support portion 124 thereof. A latch plate pin 148 is disposed within latch pin bore 146 of movable arm 132, and is slidably disposed within cam slot 150 of fixed arm 122. As movable arm 132 pivots about pivot pin 140, latch plate pin 148 is caused to slide within cam slot 150 of fixed arm 122.

Coupling assembly 120 includes a latch plate 160 having an engagement pin 162 extending from a first end portion 161 thereof, a pivot pin 164 extending from a second end portion 163 thereof, and a protrusion 166 disposed at a position between first and second end portions 161, 162. Engagement pin 162 is configured to engage a portion of release assembly 190, as discussed below, whereas pivot pin 164 is configured to pivotably couple latch plate 160 to support portion 124 of fixed arm 122.

Latch plate 160 is pivotably transitionable between an engaged position (FIG. 9B) and a disengaged position (FIG. 10B), whereby protrusion 166 of latch plate 160 engages latch plate pin 148 in the engaged position. Through actuation of release assembly 190, as discussed below, protrusion 166 transitions between positions for engagement with latch plate pin 148 and disengagement with latch plate pin 148. Accordingly, with protrusion 166 of latch plate 160 positioned for engagement with latch plate pin 148 (FIG. 9B), latch plate pin 148 is inhibited from sliding within cam slot 150 of fixed arm 122, and thus, movable arm 132 coupled to latch plate pin 148 is inhibited from pivoting. With protrusion 166 of latch plate 160 positioned for disengagement with latch plate pin 148 (FIG. 10B), latch plate pin 148 may freely slide within cam slot 150 of fixed arm 122, and thus, movable arm 132 coupled to latch plate pin 148 may freely pivot. As dictated by the position of latch plate 160, movable arm 132 is either inhibited from, or freely capable of, pivoting with respect to fixed arm 122. Thus, the position of latch plate 160 directs coupling assembly 120 into one of a locked or unlocked configuration, whereby in the locked configuration movable arm 132 is inhibited from pivoting and in the unlocked configuration movable arm 132 may freely pivot.

As discussed further below, through actuation of release assembly 190, release assembly 190 selectively transitions latch plate 160 between the engaged and disengaged positions, and thus, transitions coupling assembly 120 between the locked configuration and the unlocked configuration, via the engagement or disengagement of latch plate 160 and latch plate pin 148. With coupling assembly 120 in the locked configuration, coupling assembly 120 is inhibited from transitioning between the open and closed configurations, e.g., movable arm 132 is inhibited from pivoting with respect to fixed arm 122. With coupling assembly 120 in the unlocked configuration, coupling assembly 120 may freely transition between the open and closed configurations, e.g., movable arm 132 may freely pivot with respect to fixed arm 122.

With reference to FIGS. 4, 5, and 9A-10B, release assembly 190 includes a slide 192 disposed within cavity 116 of housing 110 and supported by second half 114 of housing 110. Slide 192 includes a latch plate recess 194 defined along a distal edge portion 193, an engagement portion 196 disposed on an external surface 195 thereof which is positioned externally of cavity 116 through port 117 of housing 110, and a bias member recess 197 extending from an internal surface 199 thereof. Latch plate recess 194 is configured to receive and engage engagement pin 162 of latch plate 160. Release assembly 190 further includes a biasing member 198 disposed within bias member recess 197 configured to engage a portion of housing 110.

Figure 3:
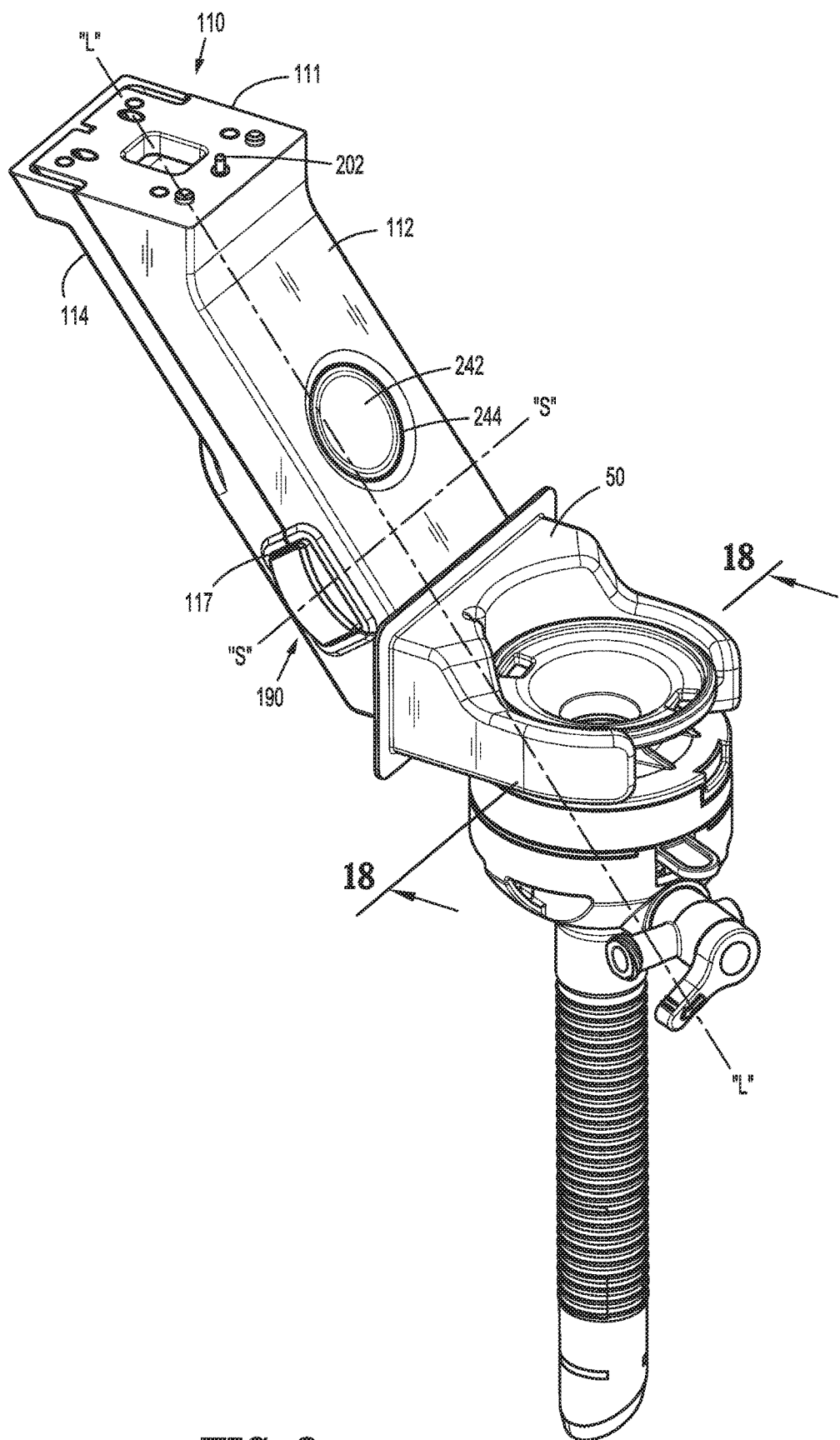
FIG. 3 is perspective view of the mount assembly of FIG. 2 with the sterile drape and the surgical part coupled therewith.

Slide 192 of release assembly 190 is configured to slide between first and second positions along an axis "S" being transverse to a longitudinal axis "L" of housing 110 (FIG. 3). In the first position of slide 192, engagement portion 196 is positioned externally of cavity 116 of housing 110 (FIG. 9A). In the second position of slide 192, engagement portion 196 partially resides within cavity 116 of housing 110 (FIG. 10A). As slide 192 translates along axis "S" between first and second positions, it should be appreciated that latch plate recess 194 of slide 192 translates or slides along an axis being parallel to axis "S". As latch plate recess 194 slides parallel to axis "S", engagement pin 162 of latch plate 160, being engaged with latch plate recess 194, is caused to translate along axis "S", thus causing latch plate 160 to pivot.

As discussed above, as latch plate 160 pivots, protrusion 166 of latch plate 160 transitions between the engaged and disengaged positions, with respect to latch plate pin 148. Accordingly, as slide 192 translates along axis "S", protrusion 166 of latch plate 160 is brought into or out of the engaged and disengaged positions to engage or disengage latch plate pin 148. More particularly, with slide 192 in the first position, protrusion 166 of latch plate 160 is in the engaged position such that protrusion 166 obstructs or otherwise inhibits latch plate pin 148 from sliding within cam slot 150, and thus, movable arm 132 is inhibited from pivoting with respect to fixed arm 122, and coupling assembly 120 is in the locked configuration. As slide 192 translates along axis "S" from the first position towards the second position, latch plate recess 194 engages and drives engagement pin 162 of latch plate 160 such that latch plate 160 is caused to pivot. As latch plate 160 pivots, protrusion 166 of latch plate 160 is caused to pivot into the disengaged position. With protrusion 166 of latch plate 160 in the disengaged position, latch plate pin 148 is free to slide within cam slot 150, and thus, movable arm 132 is free to pivot with respect to fixed arm 122, such that coupling assembly 120 is in the unlocked configuration. Accordingly, through translation of slide 192, coupling assembly 120 is transitioned between the locked configuration and the unlocked configuration.

Biasing member 198 of release assembly 190 is configured to bias slide 192 into one of the first or second positions. With slide 192 biased into one of the first or second positions, slide 192 biases latch plate 160 into one of the engaged or disengages positions, via coupling of latch plate recess 194 of slide 192 and engagement pin 162 of latch plate 160. Thus, protrusion 166 of latch plate 160 is biased into one of the engaged or disengaged positions, with respect to latch plate pin 148. As a result thereof, release assembly 190 thereby biases the coupling assembly 120 into one of the locked or unlocked configurations.

With reference to FIGS. 1-10B, the coupling and uncoupling of a surgical port with mount assembly 100 will be described. With coupling assembly 120 in the closed and locked configurations (FIGS. 9A and 9B), release assembly 190 is actuated to transition coupling assembly 120 into the unlocked configuration. Slide 192 of release assembly 190 is translated along axis "S" from the first position towards the second position (FIG. 10A), such that latch plate 160 is caused to pivot, thus transitioning protrusion 166 of latch plate 160 from the engaged position into the disengaged position, with respect to latch plate pin 148 (FIG. 10B). With protrusion 166 in the disengaged position, latch plate pin 148 may slide within cam slot 150 and movable arm 132 may be pivoted. As movable arm 132 pivots, coupling assembly 120 may assume the open configuration.

With coupling assembly 120 in the open configuration, a surgical port (e.g., surgical port 1000) may be positioned between engagement portions 126, 136 of fixed and movable arms 122, 132. Once positioned between engagement portions 126, 136, movable arm 132 may be pivoted towards fixed arm 122 such that coupling assembly 120 assumes the closed configuration. With coupling assembly 120 in the closed configuration, slide 192 is translated along axis "S" from the second position towards the first position, thus transitioning coupling assembly 120 into the locked configuration. With coupling assembly 120 in the closed and locked configurations, surgical port 1000 is thereby secured to mount assembly 100. The surgical port 1000 is uncoupled from coupling assembly 120 in a similar manner, and may thus be uncoupled from mount assembly 100.

With reference to FIGS. 2-4, 6, and 9A-12B, mount assembly 100 may further include a communication assembly 200 configured to communicate with work station 1. More particularly, communication assembly 200 provides information to work station 1 regarding the open, closed, locked, and unlocked configuration status of coupling assembly 120, and further, provides an indication if a surgical accessory, e.g., a surgical port, is positioned between, or absent from, coupling assembly 120.

Communication assembly 200 and work station 1 may be configured for wired or wireless communication. In an embodiment, communication assembly 200 includes a first pin 202 in electrical communication therewith which is disposed on the proximal portion 111 of first half 112 of housing 110. Distal portion 2a of robot arm 2 includes a corresponding second pin (not shown) in communication with work station 1, via robot arm 2. With mount assembly 100 and robot arm 2 coupled, communication assembly 200 and work station 1 are communicatively coupled via engagement of first pin 202 and the second pin (not shown). In an embodiment, communication assembly 200 is configured for wireless communications with work station 1, whereby communication assembly 200 and work station 1 are communicatively coupled by any wireless communication method as is known in the art, such as, for example, BlueTooth, ZigBee, near field communication (NFC), WiFi, or the like.

Figure 4:
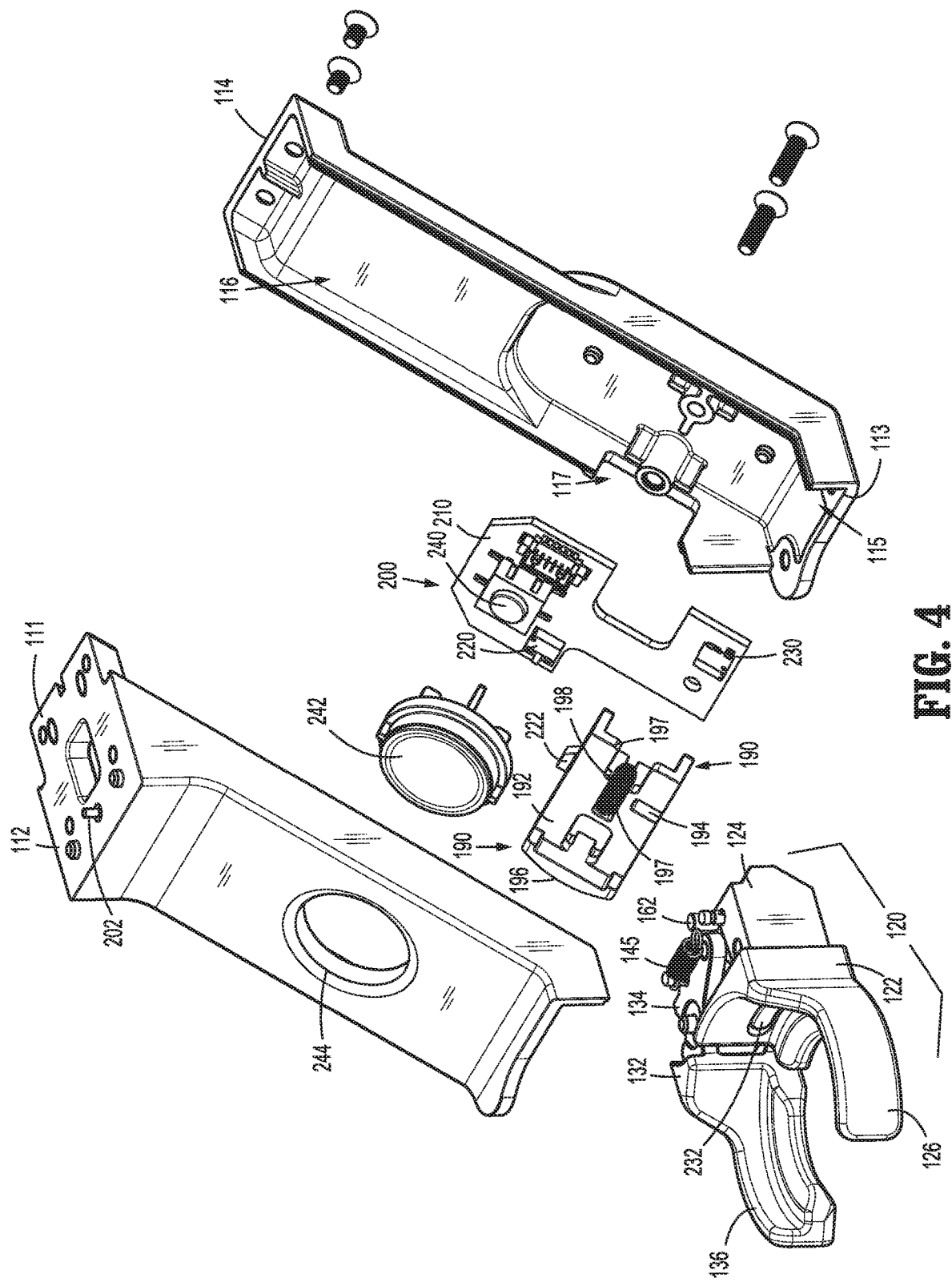
FIG. 4 is a perspective view of the mount assembly of FIG. 2, with parts separated.
Figure 5:
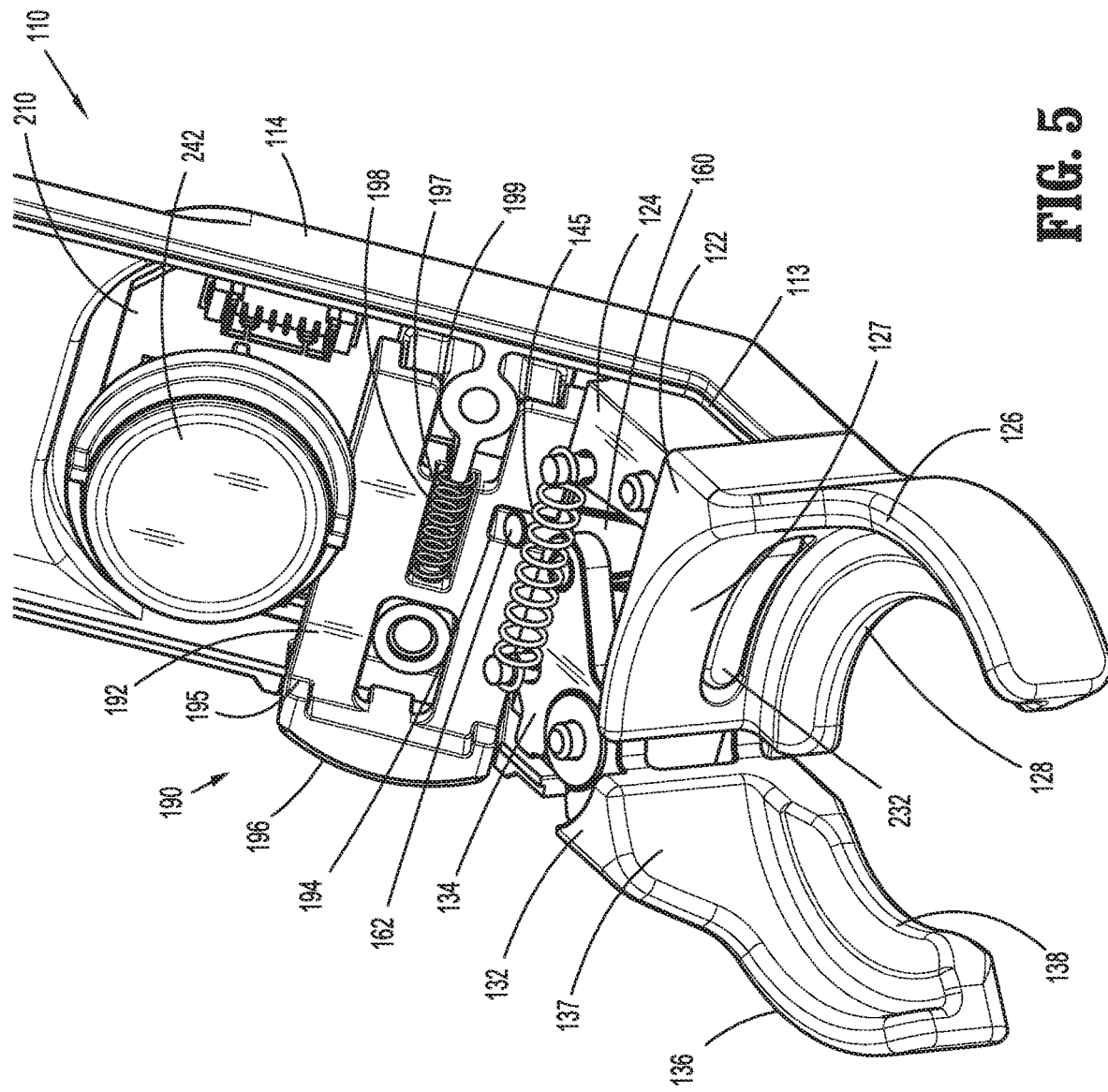
FIG. 5 is a perspective view of the mount assembly of FIG. 2, with various parts removed.

As illustrated in FIG. 4, communication assembly 200 includes a control board 210 disposed in cavity 116 of housing 110 and supported by second half 114 of housing 110. Control board 210 includes a release assembly sensor switch 220, a presence sensor switch 230, and a repositioning sensor switch 240. Communication assembly 200 further includes a button 232 configured to engage presence sensor switch 230, and a repositioning button 242 configured to engage repositioning sensor switch 240, as discussed below. Communication assembly 200 may further include any number of additional switches and/or sensors, with any number of corresponding buttons, with or without corresponding audio and/or visual user signals (e.g., LED's, buzzers, or the like), each of which may include or provide different or additional functionality.

With reference to FIGS. 9A and 10A, a switch protrusion 222 extending from slide 192 of release assembly 190 is configured to selectively engage release assembly sensor switch 220 of control board 210. As slide 192 translates along axis "S" between the first and second positions, corresponding to the locked and unlocked configurations of coupling assembly 120, as discussed above, switch protrusion 222 selectively engages, abuts, depresses, or otherwise closes release assembly sensor switch 220.

More particularly, with slide 192 in the first position, thus placing coupling assembly 120 in the locked configuration, switch protrusion 222 is in abutment to, and engaged with release assembly sensor switch 220, such that release assembly sensor switch 220 is depressed (FIG. 9A). With switch protrusion 222 engaged with release assembly sensor switch 220, communication assembly 200 provides an indication to work station 1 that coupling assembly 120 is in the locked configuration. Conversely, with slide 192 in the second position, thus placing coupling assembly 120 in the unlocked configuration, switch protrusion 222 is spaced away from, and disengaged with release assembly sensor switch 220, such that release assembly sensor switch 220 is no longer depressed (FIG. 10A). With switch protrusion 222 disengaged with release assembly sensor switch 220, communication assembly 200 provides an indication to work station 1 that coupling assembly 120 is in the unlocked configuration, and thus certain functionality of medical work station 1 may be activated or deactivated.

With reference to FIGS. 4, 6, 11A-12B, button 232 of communication assembly 200 is configured to selectively engage presence sensor switch 230 of control board 210. Button 232 includes a pivot bore 234, a contact surface 236, and a switch surface 238. Button 232 is supported by and pivotably coupled to fixed arm 122 of coupling assembly 120 via a pin 233 disposed within pivot bore 234 of button 232 and a bore 235 defined in support portion 124 of fixed arm 122. Contact surface 236 is received within a cavity 237 of support portion 124 of fixed arm 122, whereby cavity 237 extends through support portion 124 such that contact surface 236 is positionable proximate engagement portion 126 of fixed arm 122. When positioning a surgical port 1000 proximate to and in abutment with fixed arm 122 of coupling assembly 120, the surgical port 1000 is thereby brought into abutment with contact surface 236 of button 232 of communication assembly 200. Through abutment of surgical port 1000 with respect to inner surface 127 of engagement portion 126 of fixed arm 122 and contact surface 236 of button 232, button 232 is caused to pivot, with respect to fixed arm 122, through cavity 237 of support portion 124 of fixed arm 122.

Figure 11A:
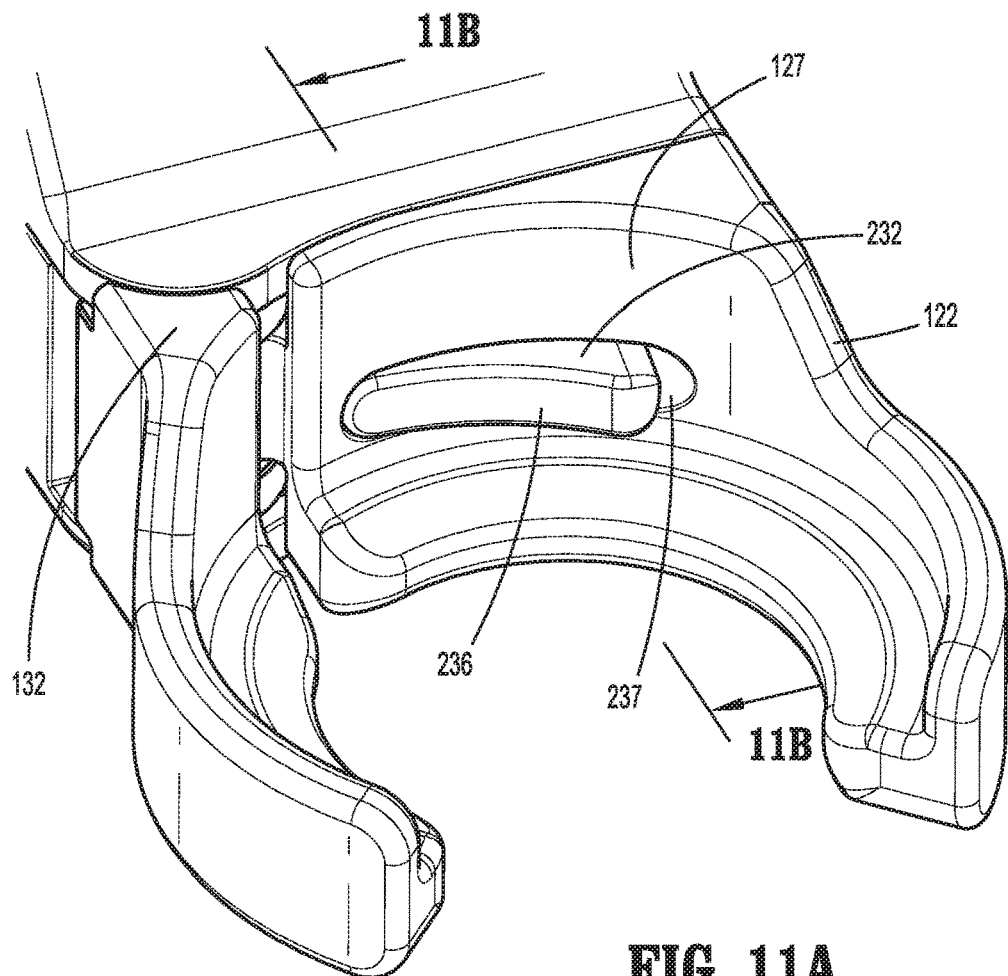
FIG. 11A is a front perspective view of a distal portion of the mount assembly of FIG. 2, with a button of a communication assembly of the mount assembly in a first position.
Figure 11B:
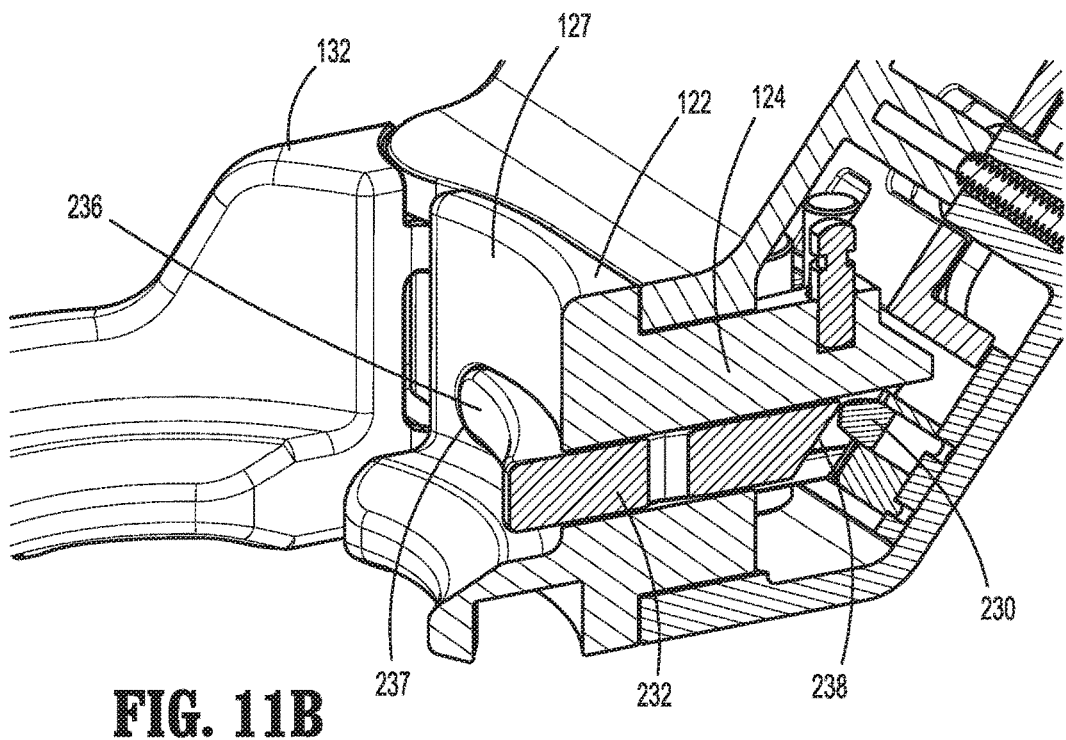
FIG. 11B is a cross-sectional view of the mount assembly of FIG. 11A taken along section line 11B-11B of FIG. 11A.
Figure 12A:
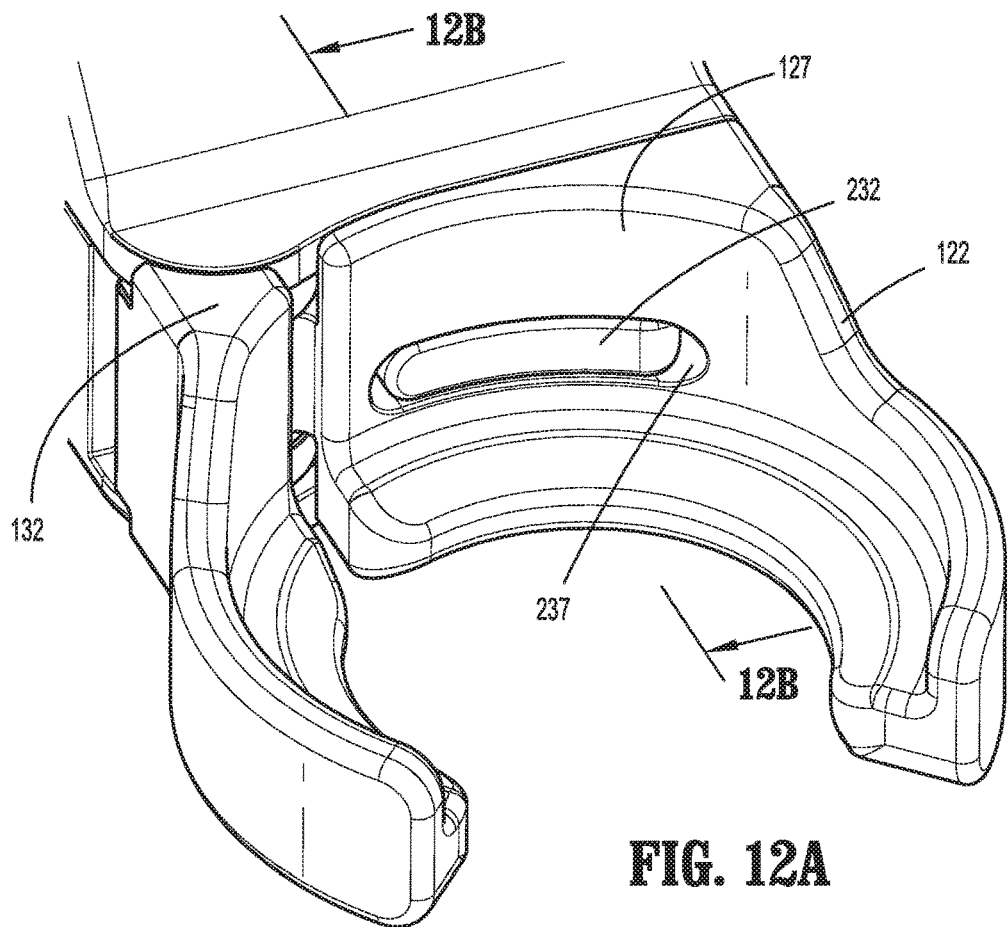
FIG. 12A is a front perspective view of the distal portion of the mount assembly of FIG. 2, with the button of the communication assembly in a second position.
Figure 12B:
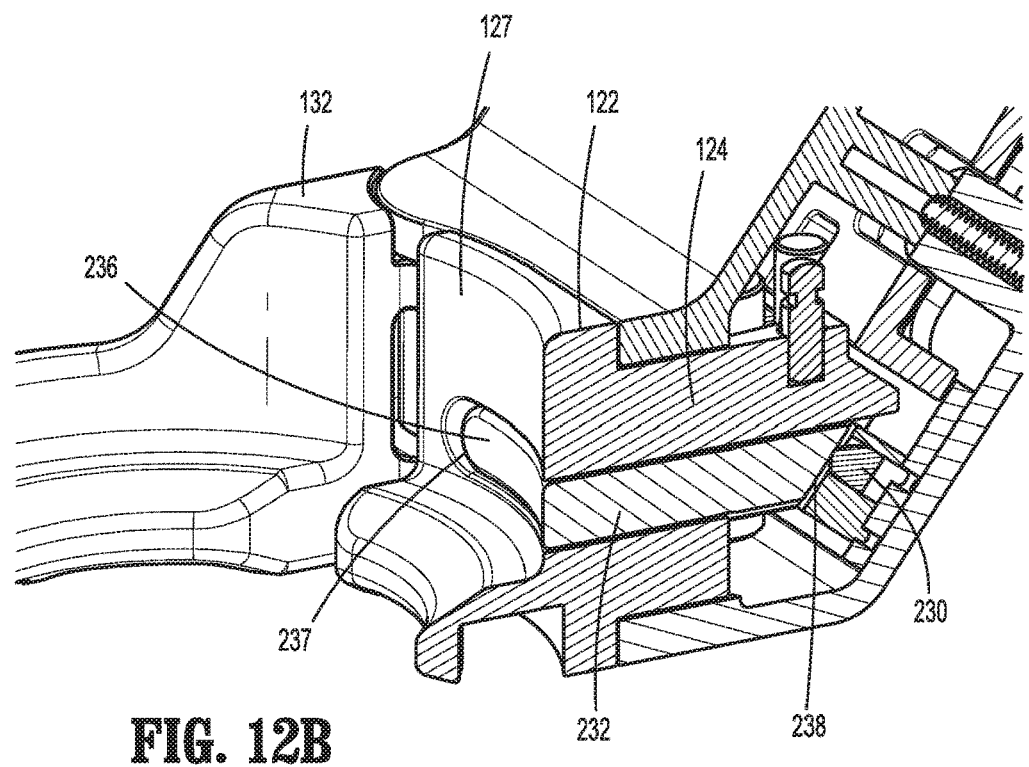
FIG. 12B is a cross-sectional view of the mount assembly of FIG. 12A taken along section line 12B-12B of FIG. 12A.

More particularly, button 232 is pivotable about pin 233 and bore 235 of fixed arm 122 between a first position (FIGS. 11A and 11B) and a second position (FIGS. 12A and 12B). In the first position of button 232, contact surface 236 of button 232 is positioned through cavity 237 of fixed arm 122 such that contact surface 236 extends through cavity 237 and past inner surface 127 of engagement portion 126 of fixed arm 122. As such, contact surface 236 protrudes from inner surface 127 of engagement portion 126 of fixed arm 122. In the second position of button 232, contact surface 236 of button 232 is positioned within cavity 237 of fixed arm 122, such that contact surface 236 is nearly flush with, or planar to inner surface 127 of engagement portion 126 of fixed arm 122. It should be appreciated that as a surgical port 1000 is brought into approximation with engagement portion 126 of fixed arm 122, and more particularly is brought into abutment with inner surface 127, the surgical port 1000 presses against contact surface 236 such that button 232 is caused to pivot about pin 233 and bore 235 from the first position (FIG. 11A) towards the second position (FIG. 12A).

With button 232 in the first position, switch surface 238 of button 232 is spaced away from, or disengaged from presence sensor switch 230, such that presence sensor switch 230 is not depressed (FIG. 11B). With button 232 in the first position, and presence sensor switch 230 not depressed, communication assembly 200 provides an indication to work station 1 that there is no surgical port positioned between fixed and movable arms 122, 132 of coupling assembly 120, and/or that a surgical port is incorrectly positioned therebetween. With button 232 in the second position, switch surface 238 of button 232 engages, abuts, depresses, or otherwise closes presence sensor switch 230 (FIG. 12B). With switch surface 238 of button 232 engaged with presence sensor switch 230, communication assembly 200 provides an indication to work station 1 that a surgical port is positioned proximate to and in abutment with coupling assembly 120.

By utilizing release assembly sensor switch 220 and presence sensor switch 230 of communication assembly 200, work station 1 may determine the operational status and state of mount assembly 100, and provide such information to a user. As noted above, release assembly sensor switch 220 provides work station 1 an indication regarding the locked and unlocked state of coupling assembly 120 of mount assembly 100. Presence sensor switch 230 provides work station 1 an indication regarding the presence, or absence of a surgical port, with respect to coupling assembly 120 of mount assembly 100, and may further provide an indication of incorrect, partial, or misaligned mounting between the surgical port and the fixed and movable arms 122, 132 of coupling assembly 120. Upon indication from communication assembly 200, work station 1 may determine if a safe operational condition is present and permit, for example, articulation of robot arm 2, actuation of surgical instrument "SI," and/or other actions performed during a surgical procedure. Conversely, work station 1 may determine if an unsafe operational condition is present and may, for example, inhibit movement of robot arm 2, inhibit continuation of a procedure, prevent actuation or articulation of surgical instrument "SI", and/or initiate a warning to a user, via audible or visual indicia utilizing operating console 5.

For example, upon indication from communication assembly 200 that a surgical port is not positioned between coupling assembly 120, via presence sensor switch 230, and coupling assembly 120 is in either the locked or unlocked configuration, via release assembly sensor switch 220, it may be determined that robot arm 2 is not in use and/or is safe to move. Upon indication from communication assembly 200 that a surgical port is positioned between coupling assembly 120, via presence sensor switch 230, and coupling assembly 120 is in the locked configuration, via release assembly sensor switch 220, it may be determined that robot arm 2 is in use, the surgical port is properly engaged with and secured to the coupling assembly 120, and thus, robot arm 2 is ready for the surgical procedure. Further, upon indication from communication assembly 200 that a surgical port is positioned between coupling assembly 120, via presence sensor switch 230, and coupling assembly 120 is in the unlocked configuration, via release assembly sensor switch 220, it may be determined that robot arm 2 is in use, the surgical port may be improperly engaged with the coupling assembly 120, coupling assembly 120 may not be in a fully closed or locked configuration, and thus, robot arm 2 is not ready for the surgical procedure and requires attention prior to proceeding. In such a situation, for example, a warning may be issued to the user, movement of robot arm 2 may be inhibited, or actuation of the surgical instrument "SI" may be forestalled.

Figure 2:
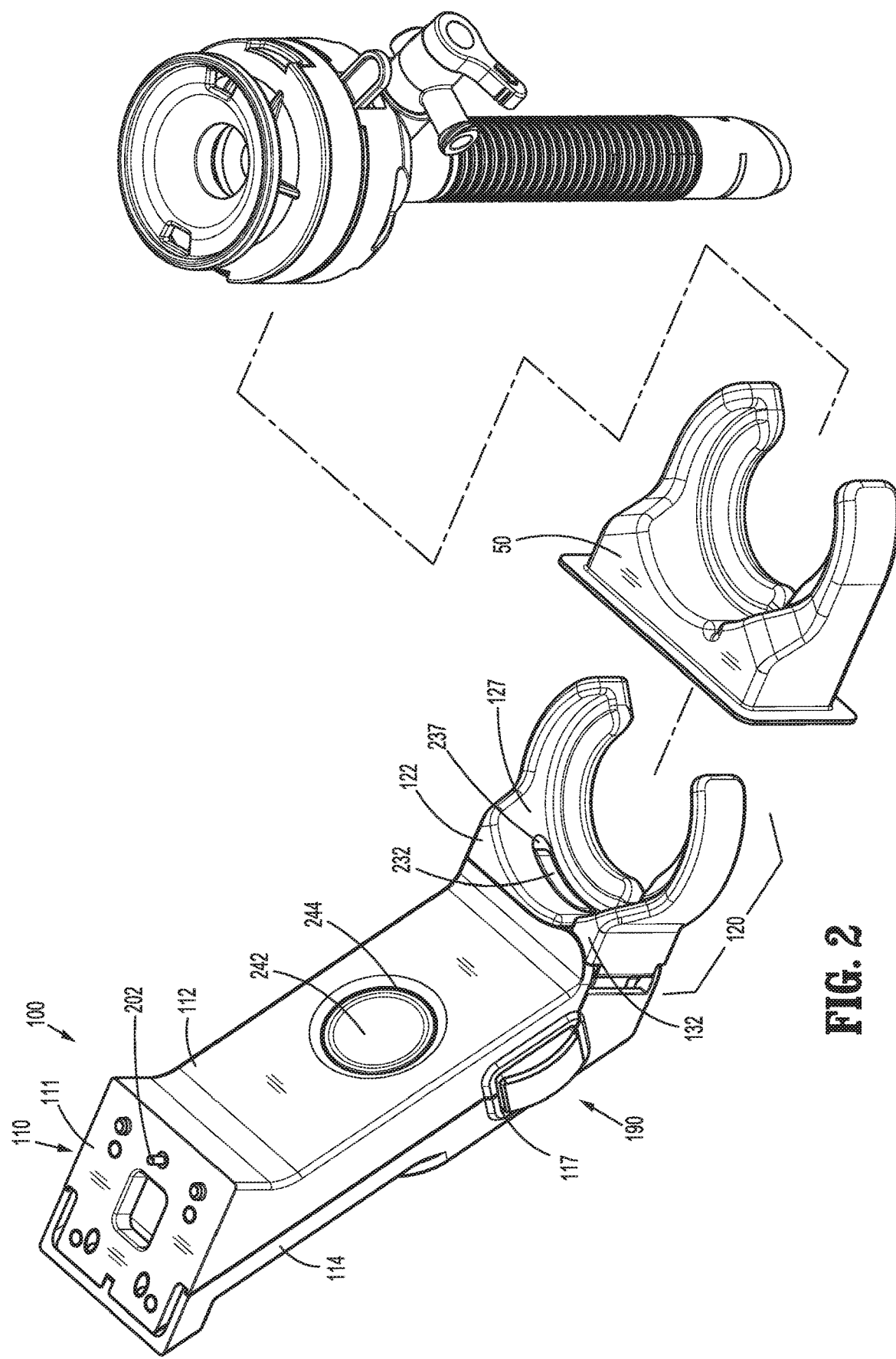
FIG. 2 is a perspective view of a mount assembly in accordance with an embodiment of the present disclosure with a sterile drape and a surgical part uncoupled therefrom.

With reference to FIGS. 2, 3, and 4, repositioning sensor switch 240 and repositioning button 242 will be discussed. Repositioning button 242 is disposed in cavity 116 of housing 110 and supported by second half 114 of housing 110. Repositioning button 242 is translatably disposed within a bore 244 defined through first half 112 of housing 110, such that repositioning button 242 may be engaged by a user. Repositioning button 242 translates between a first position, disengaged from reposition sensor switch 240, and a second position, engaged with reposition sensor switch 240. In the second position, reposition button 242 engages, abuts, depresses, or otherwise closes reposition sensor switch 240.

With reposition button 242 in the second position, and reposition sensor switch 240 depressed, robot arm 2 may be articulated, moved, or otherwise repositioned. More particularly, in the second position of reposition button 242, communication assembly 200 directs the motors and controllers associated with robot arm 2 to accept manual manipulation from a clinician, or automated instructions from work station 1. It is envisioned that as robot arm 2 undergoes manipulation, with reposition button 242 in the second position, robot arm 2 receives electro-mechanical assisted motion, such that repositioning of robot arm 2 may be facilitated. It should be appreciated that with reposition button 242 in the first position, motors and controllers associated with of robot arm 2 maintain a stop, hold, or break condition, such that manipulation of robot arm 2 is inhibited.

In an embodiment, communication assembly 200 may incorporate one or more non-contact sensors, rather than mechanical switches, such as, for example, a proximity sensor, an optical sensor, a hall-effect sensor, a magnetic sensor or magnetic registration, an induction sensor, a Radio-Frequency Identification ("RFID") sensor, combinations thereof, and the like. In such an embodiment, any one or more of: release assembly sensor switch 220 and switch protrusion 222 of slide 192; presence sensor switch 230 and switch surface 238 of button 232; or repositioning sensor switch 240 and button 242, may be configured for non-contact electrical communication therebetween. Accordingly, rather than engaging, depressing, abutting or otherwise closing a respective release assembly sensor switch 220, presence sensor switch 230, or repositioning sensor switch 240, the respective switch protrusion 222, switch surface 238, or button 242 is merely required to come into close proximity with the respective switch and/or communication assembly 200, whereby communication assembly 200 provides the associated signal to work station 1 and/or robot arm 2.

Figure 13B:
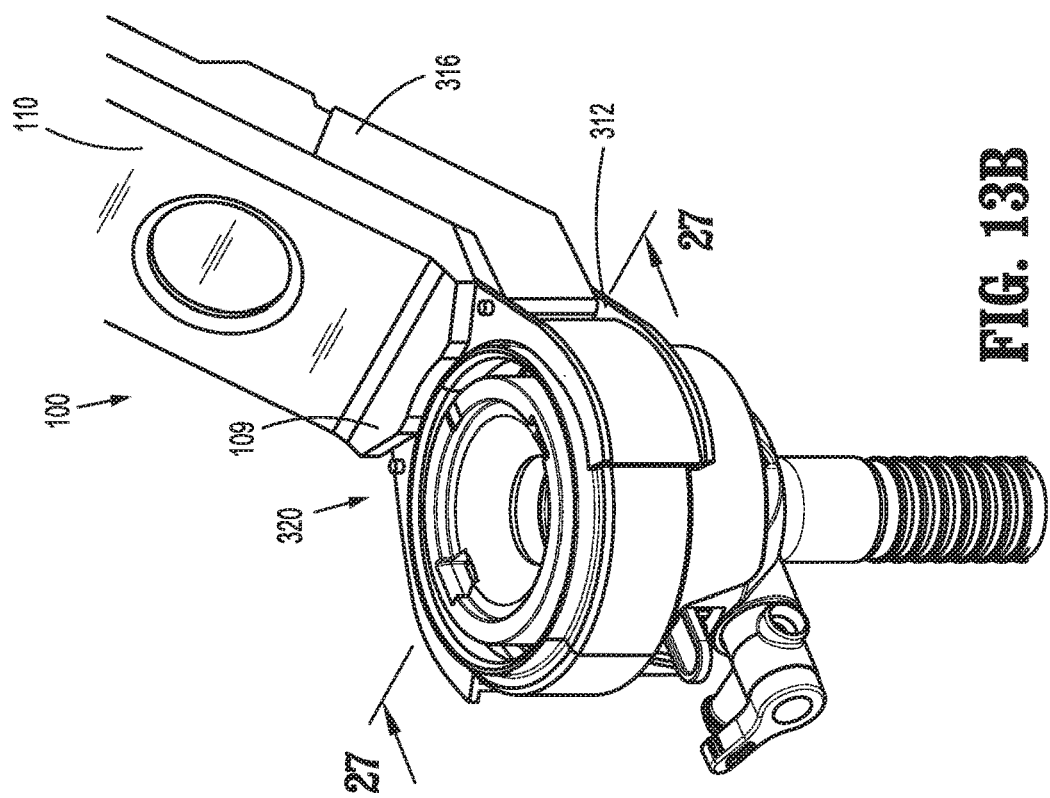
FIG. 13B is a perspective view of the mount assembly of FIG. 2, and the coupling assembly of FIG. 13B shown in a closed configuration.
Figure 13A:
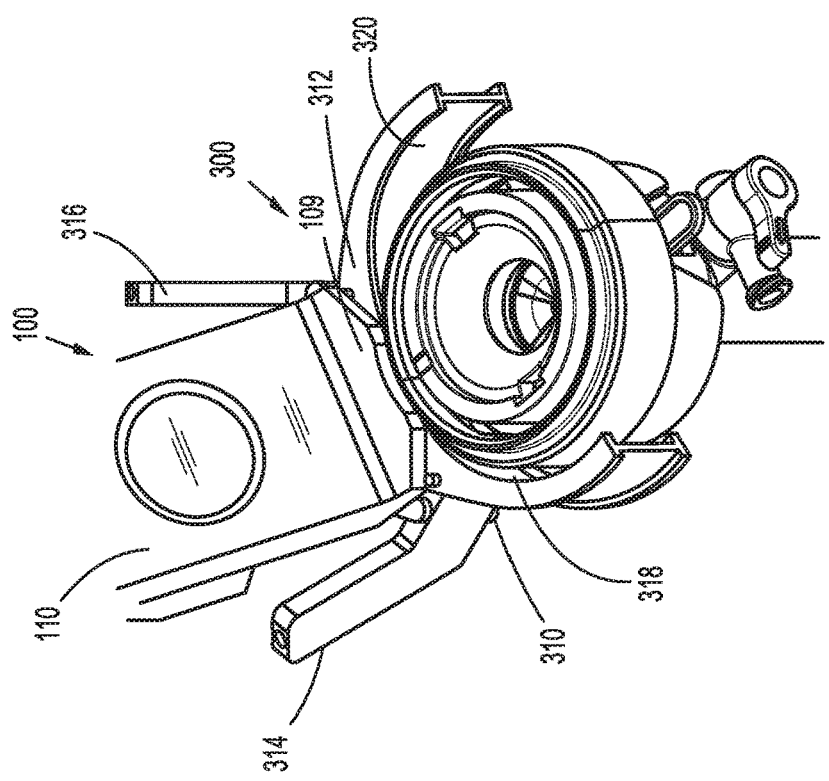
FIG. 13A is a perspective view of the mount assembly of FIG. 2, with an embodiment of a coupling assembly in accordance with the present disclosure, shown in an open configuration.

With reference to FIGS. 13A and 13B, in an embodiment, mount assembly 100 includes a coupling assembly 300 configured to receive and selectively affix a surgical port to mount assembly 100, and thus, robot arm 2. Coupling assembly 300 is supported at a distal portion 109 of housing 110 of mount assembly 100, and includes first and second arms 310, 312 and first and second actuation levers 314, 316. Each of the first and second arms 310, 312, and each of the first and second actuation levers 314, 316, are pivotably coupled to distal portion 109 of housing 110. First arm 310 is associated with first actuation lever 314, and second arm 312 is associated with second actuation lever 316. As discussed below, first and second actuation levers 314, 316 act as a release for a respective first and second arm 310, 312, such that coupling assembly 300 is transitionable between an open and a closed configuration. It is further envisioned that each of first and second arms 310, 312 defines an engagement portion 318, 320, respectively, configured to engage a portion of a surgical port. Engagement portions 318, 320 may be configured to correspond to an outer surface of a surgical port, such that secure fixation between the surgical port and the coupling assembly 300 may be achieved.

More particularly, first and second arms 310, 312 are pivotable between an approximated position (FIG. 13A) and a spaced apart position (FIG. 13B), with respect to each other. The spaced apart position of first and second arms 310, 312 corresponds to an open configuration of coupling assembly 300 (FIG. 13A), and the approximated position corresponds to a closed configuration of coupling assembly 300 (FIG. 13B). Further, first and second actuation levers 314, 316 are pivotable between a first position (FIG. 13A) and a second position (FIG. 13B). The first position of first and second actuation levers 314, 316 corresponds to the open configuration of coupling assembly 300, and the second position of first and second actuation levers 314, 316 corresponds to the closed configuration of coupling assembly 300.

During coupling and uncoupling of a surgical port to coupling assembly 300 of mount assembly 100, first and second actuation levers 314, 316 are pivoted into the first position, such that first and second arms 310, 312 may pivot into the spaced apart position, and thus, coupling assembly 300 is transitioned into the open configuration (FIG. 13A). In the open configuration of coupling assembly 300, a surgical port may be positioned between first and second arms 310, 312 and brought into abutment with engagement portions 318, 320, respectively. With the surgical port positioned between first and second arms 310, 312, and aligned with engagement portions 318, 320, first and second arms 310, 312 may be pivoted into the approximated position, thereby positioning and affixing the surgical port therebetween in a clamping fashion. With coupling assembly 300 in the closed configuration (FIG. 13B), first and second actuation levers 314, 316 inhibit first and second arms 310, 312 from pivoting into the spaced apart position, such that coupling assembly 300 is securely maintained in the closed configuration. Thus, in the closed configuration of coupling assembly 300, the surgical port is thereby affixed to mount assembly 100, and thus robot arm 2.

During uncoupling of a surgical port from coupling assembly 300, first and second actuation levers 314, 316 are pivoted from the second position (FIG. 13B) towards the first position (FIG. 13A), thereby permitting first and second arms 310, 312 to pivot towards the spaced apart position, bringing coupling assembly 300 into the open configuration. With coupling assembly 300 in the open configuration, the surgical port may be uncoupled from first and second arms 310, 312.

Figure 14A:
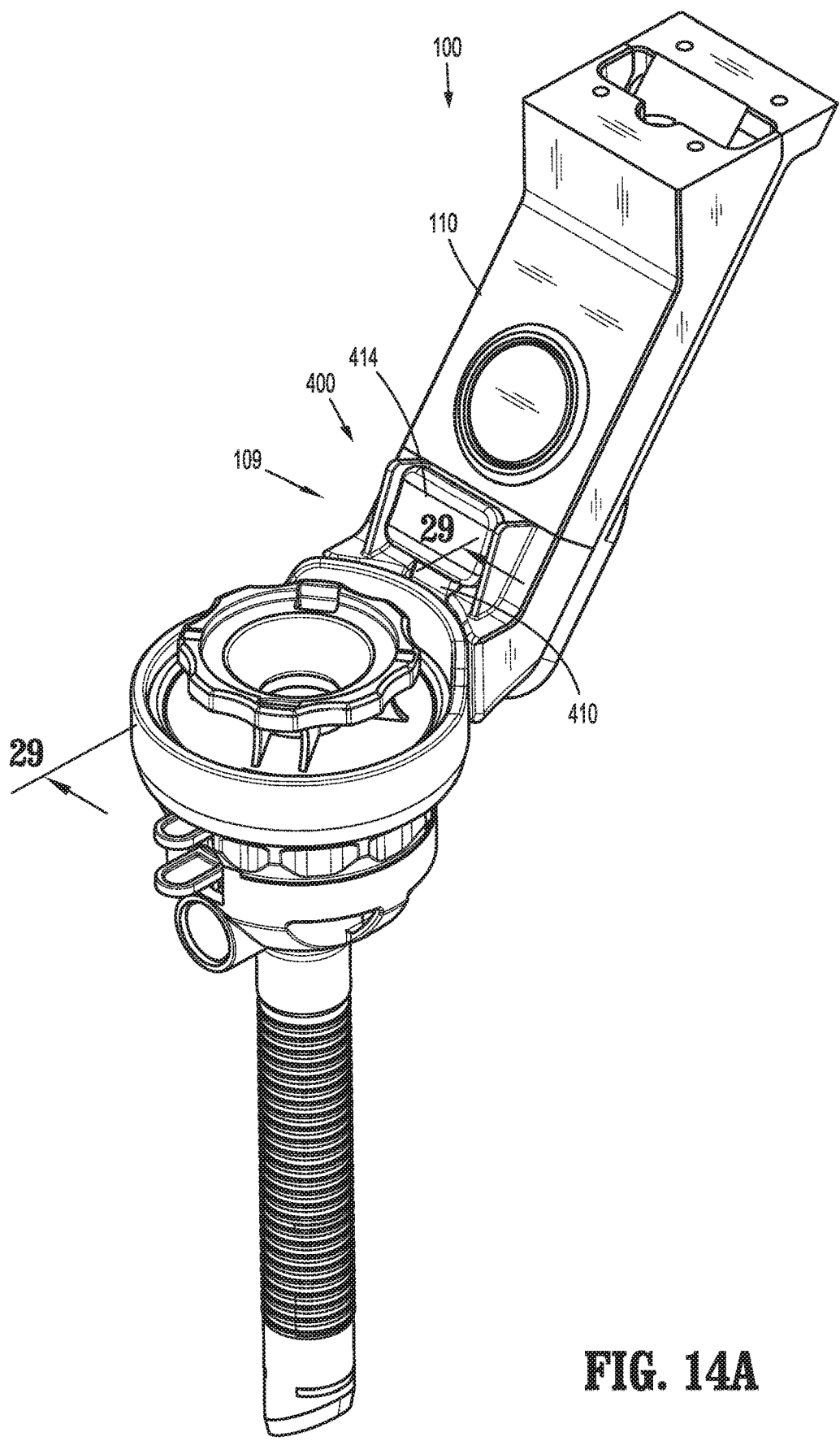
FIG. 14A is a perspective view of the mount assembly of FIG. 2, with another embodiment of a coupling assembly in accordance with the present disclosure, uncoupled from a surgical port.
Figure 14B:
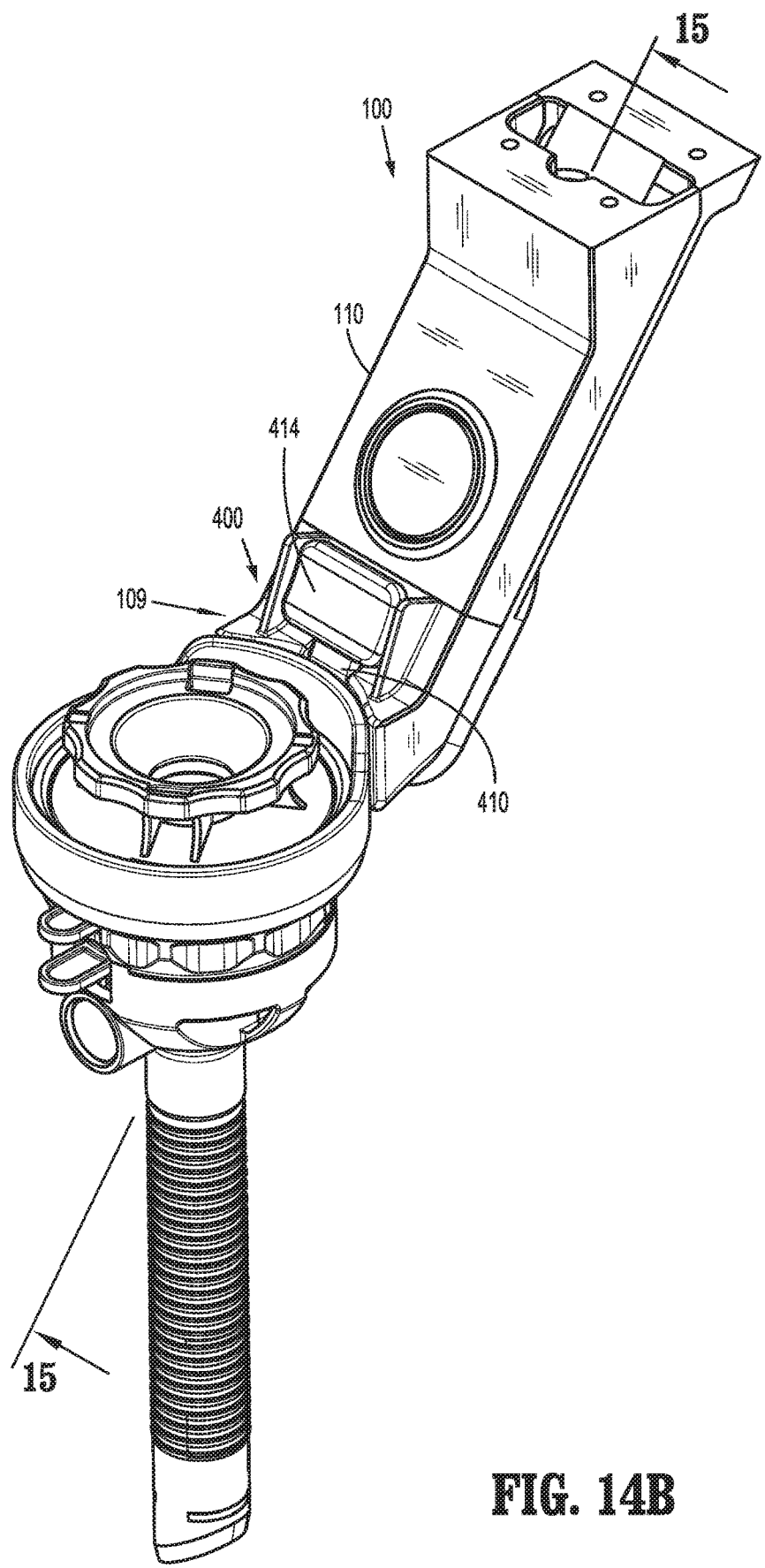
FIG. 14B is a perspective view of the mount assembly of FIG. 2 and the coupling assembly of FIG. 13B, coupled with a surgical port.
Figure 15:
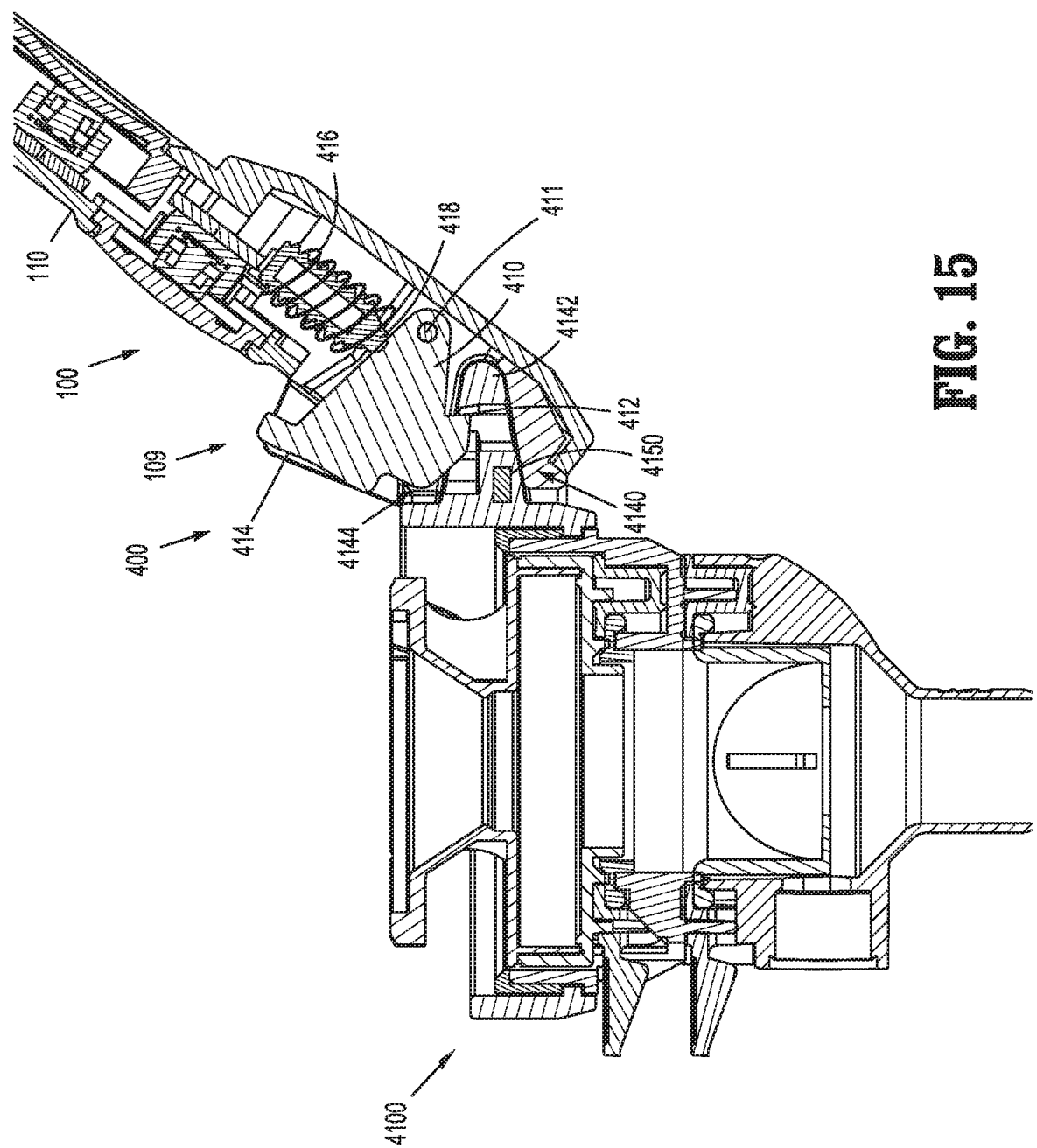
FIG. 15 is a cross-sectional view of the mount assembly of FIG. 2 and the surgical port of FIG. 14B taken along the section line 15-15 of FIG. 14B.

With reference to FIGS. 14A-15, in an embodiment, mount assembly 100 includes a coupling assembly 400 configured to engage and selectively affix a surgical port to mount assembly 100, and thus, robot arm 2. Coupling assembly 400 is supported at distal portion 109 of housing 110 of mount assembly 100, and includes a latch 410 pivotably coupled to housing 110. Latch 410 includes a hooked portion 412 configured to selectively engage or disengage with a portion of a surgical port, and an engagement portion 414 configured for user actuation such that latch 410 pivots. Upon actuation of engagement portion 414 by a user, latch 410 is caused to pivot about a pivot pin 411. More particularly, latch 410 pivots between a first and second position, whereby hooked portion 412 pivots into and out of an engagement with respect to a portion of a surgical port. Thus, coupling assembly 400 transitions between an engaged and disengaged configuration with respect to a surgical port, respectively.

Coupling assembly 400 may further include a biasing member 416 disposed between latch 410 and housing 110. Biasing member 416 is configured to bias latch 410 into one of the first or second positions, and more particularly, bias hooked portion 412 of latch 410 into or out of engagement with respect to a portion of a surgical port. Further, coupling assembly 400 may include a latch lock 418 disposed between latch 410 and housing 110. Latch lock 418 is configured to inhibit latch 410 from pivoting about pivot pin 411, such that latch 410 is maintained and secured in one of the first or second positions, which therefore maintains and secures hooked portion 412 into or out of engagement with respect to a surgical port.

During coupling and uncoupling of a surgical port with coupling assembly 400, a portion of the surgical port is brought into proximity with hooked portion 412 of latch 410. Latch 410 is pivoted into the first position, such that hooked portion 412 is brought into engagement with the portion of the surgical port, and the coupling assembly 400 is transitioned into the engaged configuration (FIGS. 14B and 15). Alternatively, a portion of the surgical port may be driven against the hooked portion 412 of latch 410, thus causing hooked portion 412 to pivot into engagement therewith, thus transitioning coupling assembly 400 into the engaged configuration. Latch lock 418 may be utilized to securely maintain latch 410 in the first position, hooked portion 412 in the engaged position, and coupling assembly 400 in the engaged configuration.

During uncoupling of a surgical port from coupling assembly 400, latch lock 418 may be disengaged from latch 410, thus permitting latch 410 to pivot about pivot pin 411. With latch 410 free to pivot, engagement portion 414 is actuated such that latch 410 pivots into the second position, hooked portion 412 pivots out of disengagement with respect to a portion of the surgical port, and coupling assembly 400 transitions into the disengaged configuration. Accordingly, the surgical port may be removed and uncoupled from coupling assembly 400 of mount assembly 100, and thus robot art 2 (FIG. 14A).

With reference to FIGS. 2 and 3, mount assembly 100 may be further configured for a sterile drape 50 to enshroud or enclose a portion thereof, such that a sterile barrier is positioned and maintained between mount assembly 100, coupling assemblies 120, 300, or 400 associated therewith, and the surgical accessory coupled thereto. Sterile drape 50 is configured to enshroud or enclose all of or a portion of housing 110 of mount assembly 100, and/or all of or a portion of fixed or movable arms 122, 132 of coupling assembly 120; first and second arms 310, 312 of coupling assembly 300; and hooked portion 412 of latch 410 of coupling assembly 400. Further, sterile drape 50 may be positioned about mount assembly 100 in either the closed or open configurations of coupling assemblies 120 and 300. It is envisioned that sterile drape 50 may define a flexible, deformable, or stretchable material, such that during actuation and operation of coupling assemblies 120, 300, and 400 the structural integrity of sterile drape 50 is maintained, and further, that the actuation and operation of coupling assemblies 120, 300, and 400 are uninhibited by sterile drape 50. Sterile drape 50 may include any biocompatible material as is known in the art such that a sterile barrier is maintained, and may include, for example, an elastomer, a silicone, a polyethylene, a polyvinylechloride, a polyurethane, a polylactide, combinations thereof, and the like.

Turning now to FIGS. 16-29, embodiments of surgical ports in accordance with the present disclosure will be discussed herein below. It should be appreciated that the following embodiments of surgical ports are compatible with mount assembly 100 and one or more of coupling assemblies 120, 300, or 400. The surgical ports disclosed herein are configured to receive a surgical instrument "SI" therethrough; provide access into a patient cavity through either a natural orifice or an incision in tissue; maintain a fluidic seal between the patient cavity and the external environment, with or without a surgical instrument "SI" disposed through the surgical port; redirect and transfer external forces exerted against or upon the surgical instrument "SI" to robot arm 2, via mount assembly 100 resulting from the natural orifice or the surrounding tissue of an incision; increase the load bearing capability upon the surgical port and/or surgical instrument "SI" without compromising the fluidic seal integrity; provide mechanical lead-in for automated insertion of un-supported surgical instruments "SI" therethrough; work collaboratively with surgical drape 50 and the like; provide a minimal footprint to minimize obstruction of the surgical field; and/or provide expeditious coupling and uncoupling to robot arm 2, via mount assembly 100, and the corresponding coupling assemblies 120, 300, and 400.

With reference to FIGS. 16-20, an embodiment of a surgical port 1000 includes a seal housing 1100, a seal assembly 1200, a seal cover 1300, a cannula seal 1400, and a cannula assembly 1500. An interior surface of each of seal housing 1100, seal cover 1300, and cannula assembly 1500 define a central lumen 1002 of surgical port 1000. Central lumen 1002 is configured to receive a portion of surgical instrument "SI" therethrough, such that a distal portion of surgical instrument "SI" may access an internal body cavity, as described herein. For a more detailed description of a similar surgical port, reference can be made to U.S. Pat. No. 5,807,338, the entire contents of which are incorporated by reference herein.

As discussed below, mount assembly 100 is configured to selectively engage with, and affix to a portion of seal housing 1100, such that surgical port 1000 is thereby affixed to mount assembly 100, and thus robot arm 2. Seal housing 1100 is couplable to seal cover 1300, whereby seal assembly 1200 is coupled therebetween. Seal cover 1300 is couplable to cannula assembly 1500, whereby cannula seal 1400 is coupled therebetween. For further discussion of the construction and operation of surgical port 1000, and surgical ports similar thereto, reference may be made to U.S. Pat. No. 5,603,702, filed on Aug. 8, 1994 and entitled "Valve System for Cannula Assembly," the entire content of which is incorporated herein by reference.

Figure 16:
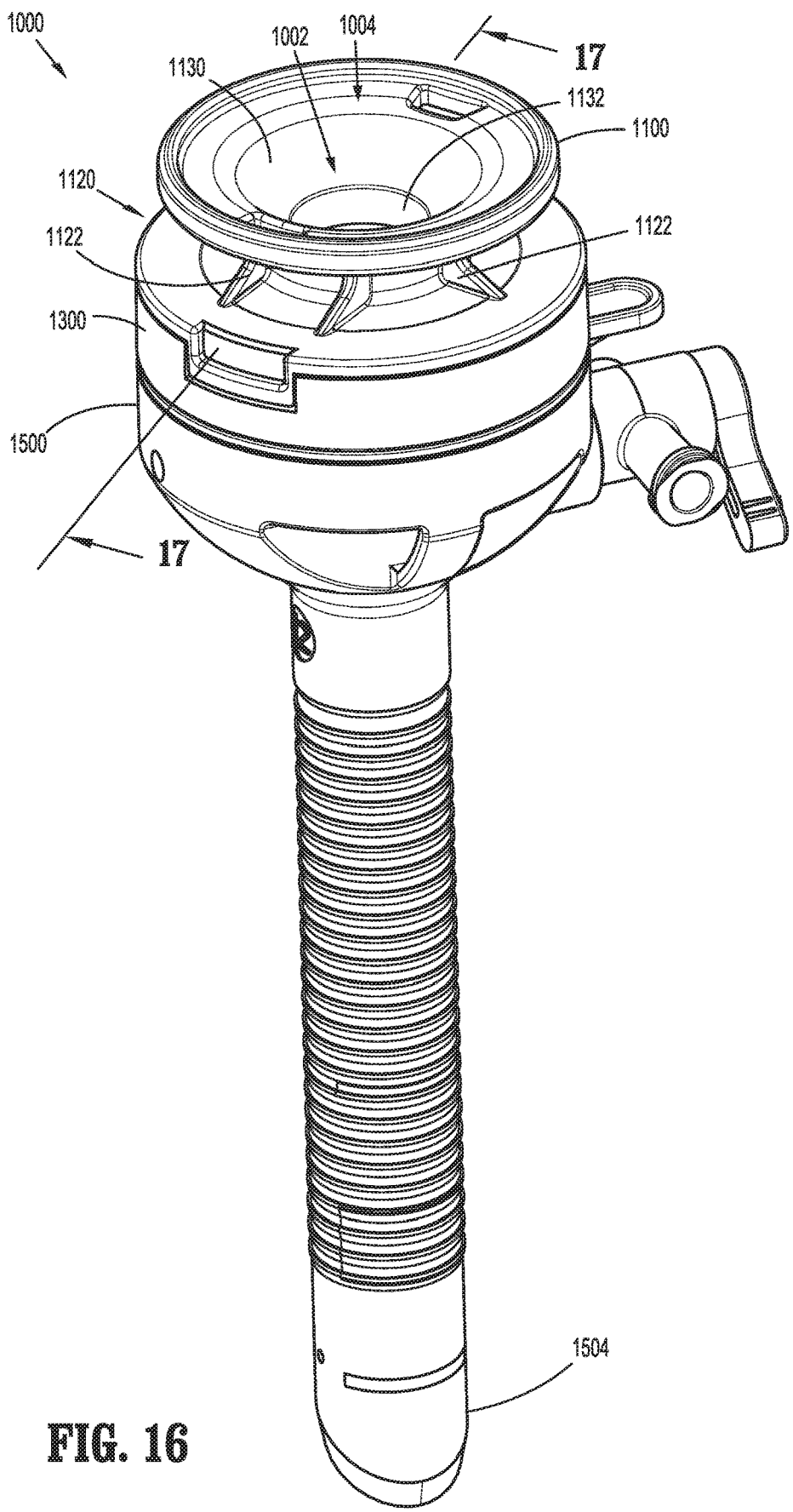
FIG. 16 is a perspective view of a surgical port in accordance with the present disclosure.
Figure 17:
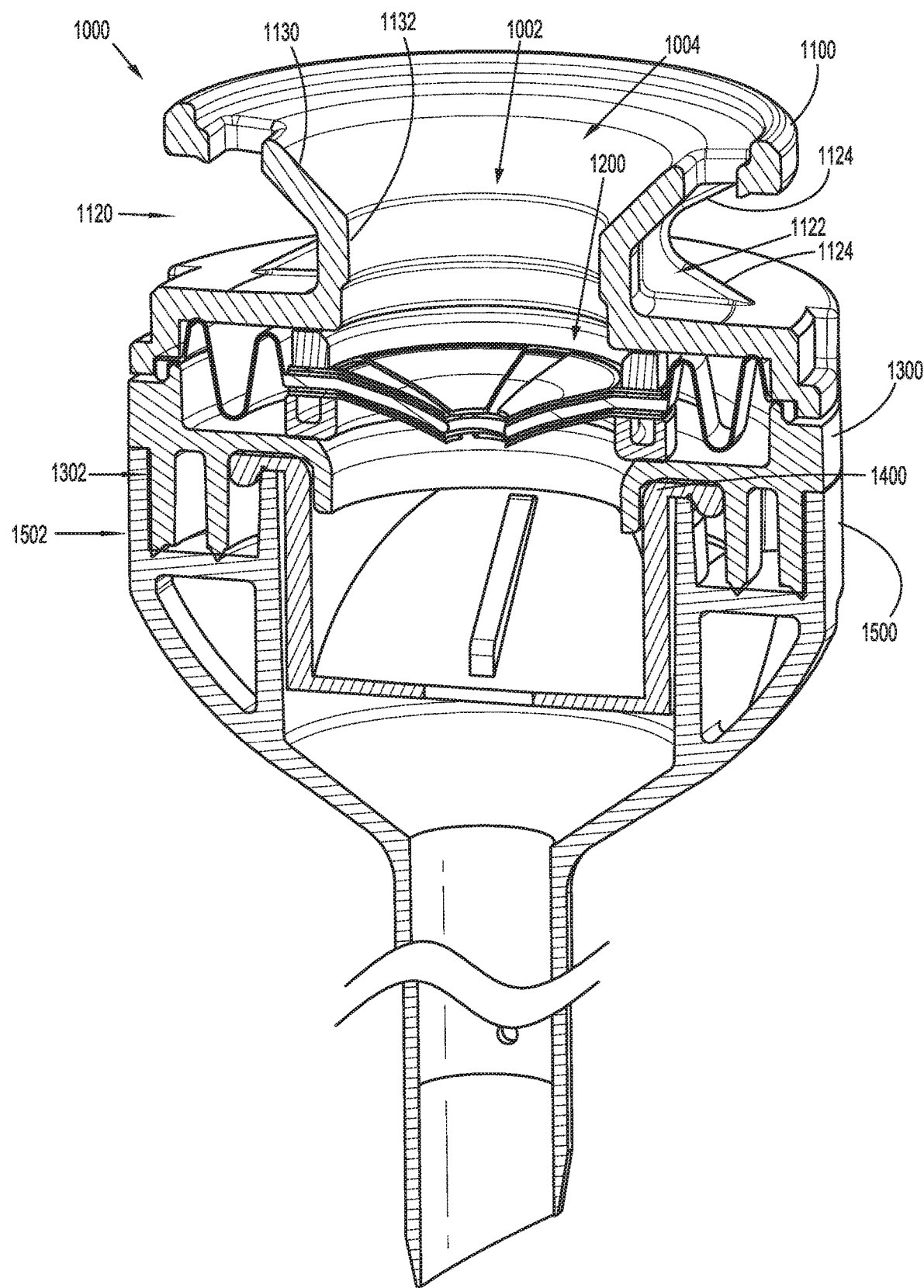
FIG. 17 is a cross-sectional view of the surgical port of FIG. 16 taken along the section line 17-17 of FIG. 16.
Figure 18:
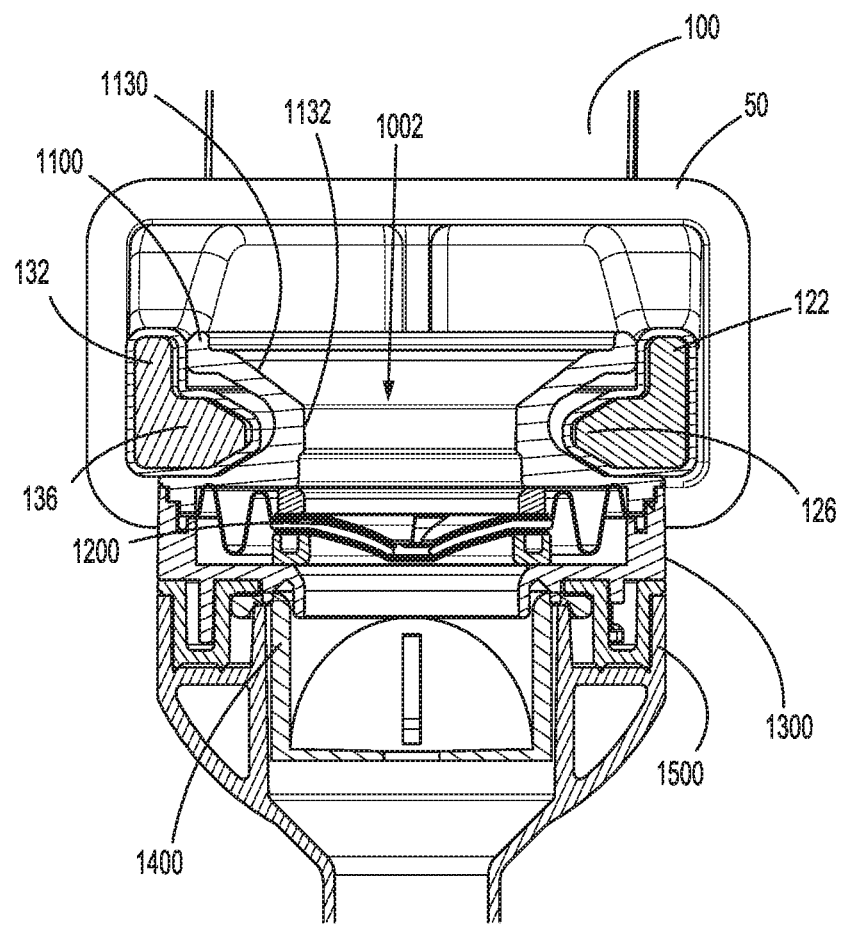
FIG. 18 is a cross-sectional view of the mount assembly of FIG. 3 and the surgical port of FIG. 16 taken along section line 18-18 of FIG. 3.

With reference to FIGS. 16-18, surgical port 1000 is configured for expeditious and secure fixation with mount assembly 100. More particularly, seal housing 1100 of surgical port 1000 is configured for secure fixation with coupling assemblies 120, 300 of mount assembly 100. In an embodiment, seal housing 1100 includes an engagement region 1120 disposed about an external radial surface thereof, where engagement region 1120 includes a plurality of ribs 1122 disposed thereon. Engagement region 1120 is configured to mate with engagement portions 126, 136 of fixed and movable arms 122, 132 of coupling assembly 120, or engagement portions 318, 320 of first and second arms 310, 312 of coupling assembly 300. More particularly, engagement region 1120, together with ribs 1122, are configured to correspond to an outer profile of engagement portions 126, 136 of fixed and movable arms 122, 132 of coupling assembly 120, and/or engagement portions 318, 320 of first and second arms 310, 312 of coupling assembly 300, such that abutment and fixation therebetween may be achieved. It should be appreciated that the generally circular cross-sectional profile of engagement region 1120, and the corresponding arcuate profile of fixed and movable arms 122, 132, and first and second arms 310, 312, provide surgical port 1000 with a rotational degree of freedom, about a longitudinal axis defined along central lumen 1002.

As coupling assemblies 120, 300 transition from the open configuration (FIG. 10A) to the closed configuration (FIGS. 3, 9A, and 18), engagement portions 126, 136 of coupling assembly 120 and engagement portions 318, 320 of coupling assembly 300 come into abutment with and clamp about engagement region 1120 of seal housing 1100. A ramped surface 1124 of each respective rib 1122 aids, guides, and directs engagement portions 126, 136 and engagement portions 318, 320 into secure fixation with engagement region 1120 of seal housing 1100. More specifically, ramped surface 1124 provides a lead-in geometry for orientation and alignment during fixation of seal housing 1100 and mount assembly 100. Accordingly, with coupling assemblies 120, 300 in the closed configuration, fixed and movable arms 122, 132 of coupling assembly 120, and first and second arms 310, 312 of coupling assembly 300, may be accurately aligned with, and securely affixed to, engagement region 1120 of seal housing 1100.

In further embodiments, seal housing 1100 of surgical port 1000 may include a chamfered surface 1130 disposed along an interior surface 1132 of seal housing 110, whereby interior surface 1132 delineates a proximal portion 1004 of central lumen 1002 of surgical port 1000 from a distal portion thereof. Chamfered surface 1130 is configured to facilitate insertion (e.g., manual and/or automated) of surgical instruments "SI" through central lumen 1002 of surgical port 1002. More particularly, during insertion of surgical instrument "SI" through central lumen 1002 of surgical port 1000, as a distal portion of surgical instrument "SI" approximates seal housing 1100, a distal end of surgical instrument "SI" may come into abutment with, and ride along, chamfered surface 1130. As surgical instrument "SI" rides along chamfered surface 1130, surgical instrument "SI" is directed into and through central lumen 1002, such that chamfered surface 1130 serves as a lead-in geometry to assist and facilitate alignment and orientation of surgical instrument "SI" through central lumen 1002 of surgical port 1000.

As should be appreciated, with a distal portion 1504 of cannula assembly 1500 positioned within a cavity of a patient, central lumen 1002 of surgical port 1000 creates a pathway for the passage of surgical instruments "SI" therethrough. During such a procedure, seal assembly 1200 and cannula seal 1400 act as a fluidic seal to maintain the internal pressures of the cavity of a patient. Further still, seal assembly 1200 and cannula seal 1400 are configured as one-way valves of central lumen 1002, such that internal pressure of the cavity is maintained whether a surgical instrument "SI" is positioned within central lumen 1002, or absent therefrom. More particularly, each of seal assembly 1200 and cannula seal 1400 are configured to deform as a surgical instrument "SI" is passed therethrough, and positioned within central lumen 1002, such that each of seal assembly 1200 and cannula seal 1400 create a fluid tight seal about a portion of the surgical instrument "SI". Seal assembly 1200 and/or cannula seal 1400 may be fabricated from a resilient material, e.g., rubber, where seal assembly 1200 may include one or more layers of resilient material and cannula seal 1400 may generally define a duck bill shape. As discussed further below, surgical port 1000 is configured to create and maintain a robust fluid tight seal within central lumen 1002, between seal assembly 1200 and cannula seal 1400, between seal cover 1300 and cannula assembly 1500, and between a surgical instrument "SI" inserted therein.

Figure 19:
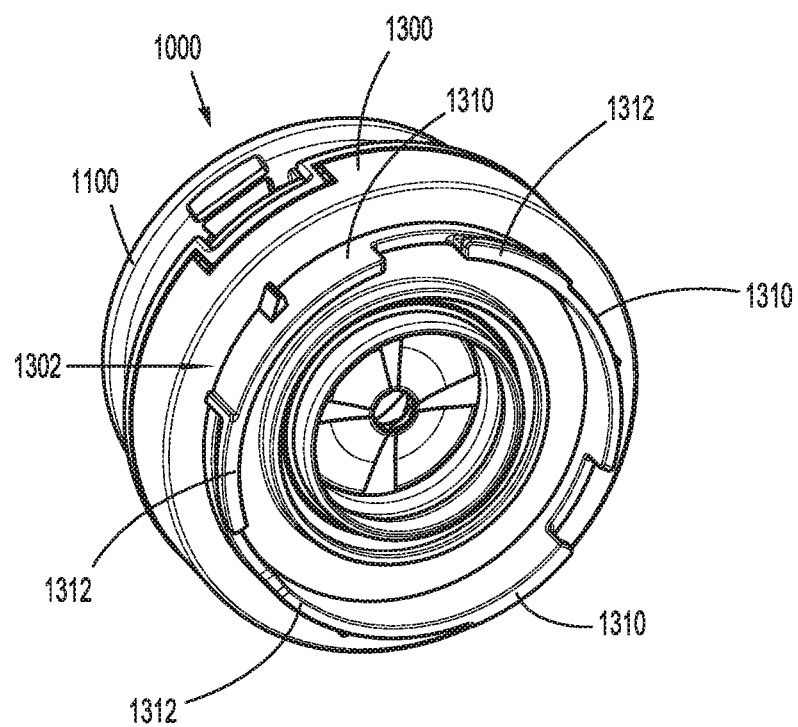
FIG. 19 is a bottom perspective view of an embodiment of a seal cover of the surgical port of FIG. 16 in accordance with the present disclosure.
Figure 20:
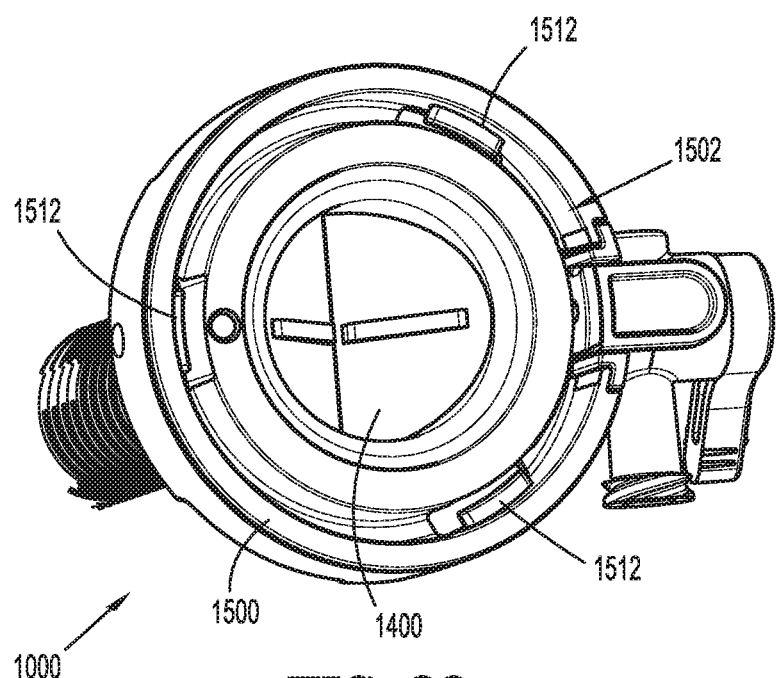
FIG. 20 is a top perspective view of an embodiment of a cannula assembly of the surgical port of FIG. 16 in accordance with the present disclosure.

With reference to FIGS. 19 and 20, with respect to the engagement and coupling of seal cover 1300 and cannula assembly 1500, a distal portion 1302 of seal cover 1300 is configured to couple with a proximal portion 1502 of cannula assembly 1500, such that a secure and fluid tight seal is maintained therebetween. In an embodiment, distal portion 1302 of seal cover 1300 includes a plurality of lobes 1310, where each respective lobe 1310 defines a key feature 1312 thereon. In an embodiment, and as illustrated in FIGS. 18 and 19, seal cover 1300 may include three lobes 1310 radially disposed about distal portion 1302 of seal cover 1300. It is envisioned that lobes 1310 may be equally radially disposed about the distal portion 1302 of seal cover 1300.

In such an embodiment, cannula assembly 1500 includes a plurality of key features 1512 radially disposed about, and extending from proximal portion 1502. Each respective key feature 1512 is configured to engage with and couple to a respective key feature 1312 of lobe 1310 of seal cover 1300. It is envisioned that key features 1512 may be equally radially disposed about the proximal portion 1502 of cannula assembly 1500 and/or configured to correspond to the position of key feature 1312 of seal cover 1300. As should be appreciated, with distal portion 1302 of seal cover 1300 in abutment with proximal portion 1502 of cannula assembly 1500, key feature 1312 of seal cover 1300 is brought into abutment with key feature 1512 of cannula assembly 1500. Rotation of seal cover 1300 or cannula assembly 1500, with respect to the other, engages respective key features 1312, 1512, such that seal cover 1300 and cannula assembly 1500 are thereby securely affixed. With seal cover 1300 and cannula assembly 1500 securely affixed, cannula seal 1400 is thereby securely disposed therebetween in a fluid tight arrangement.

Figure 21:
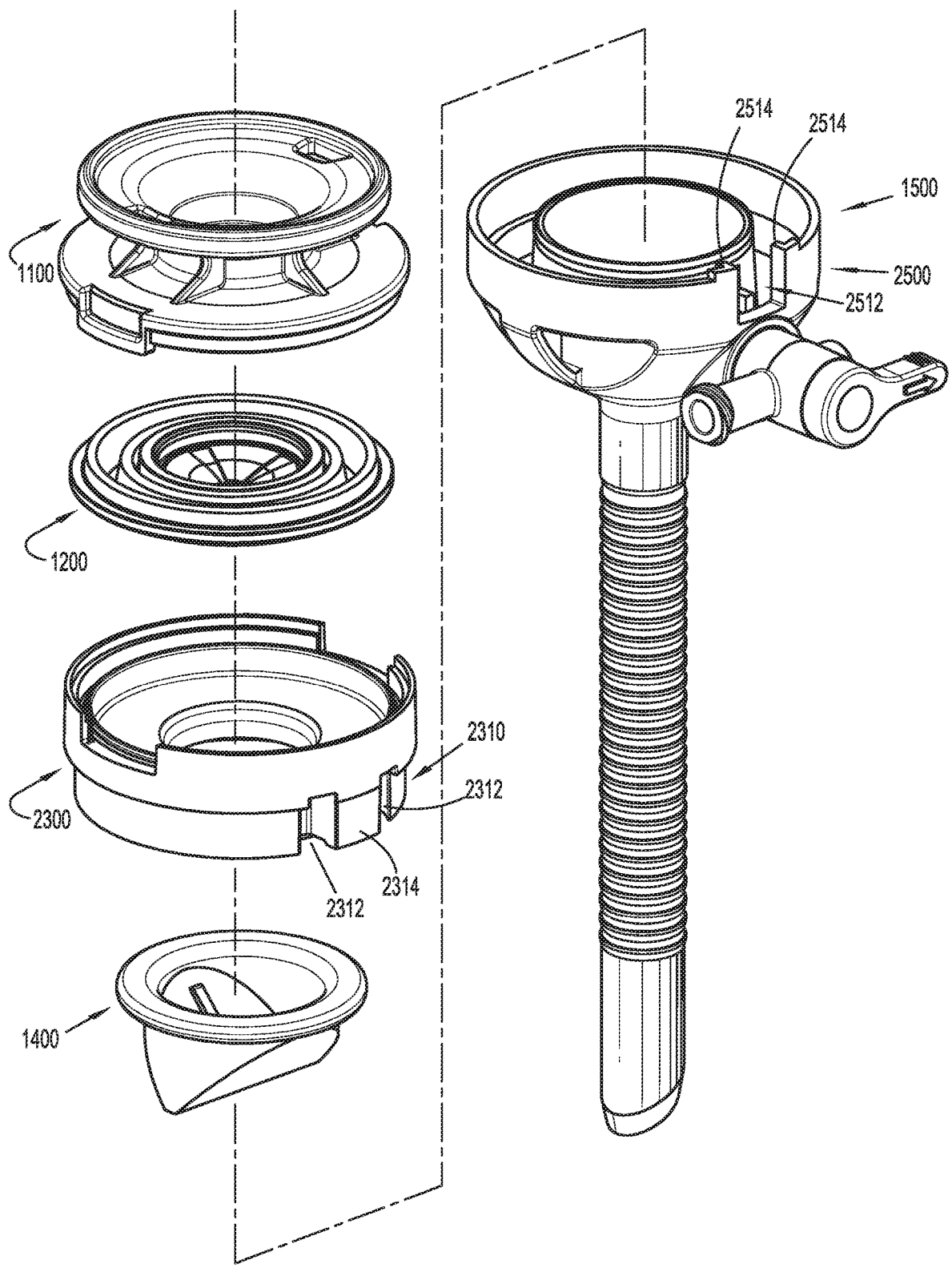
FIG. 21 is a perspective view, with parts separated, of the surgical port of FIG. 16, with an embodiment of a seal cover and a cannula assembly in accordance with the present disclosure.
Figure 22A:
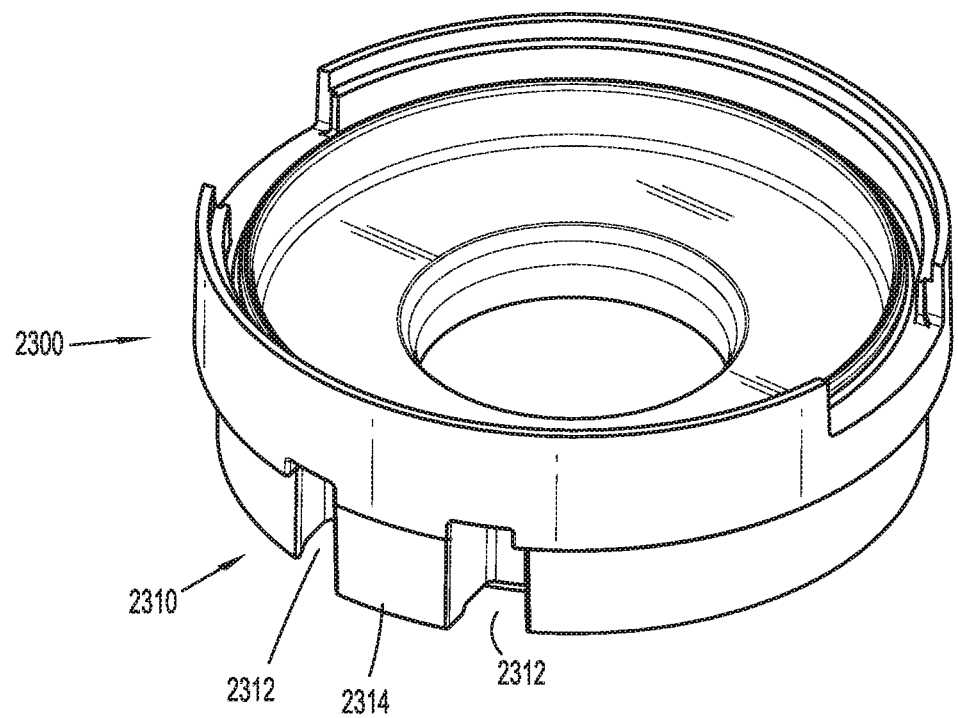
FIG. 22A is a top perspective view of the seal cover of FIG. 21.
Figure 22B:
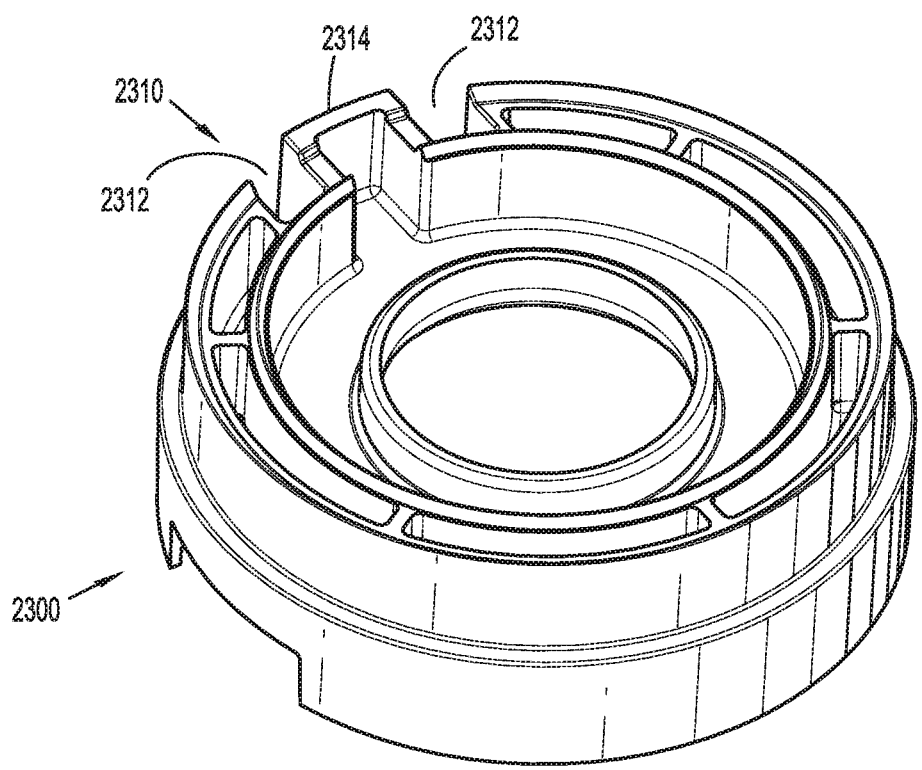
FIG. 22B is a bottom perspective view of the seal cover of FIG. 21.
Figure 23:
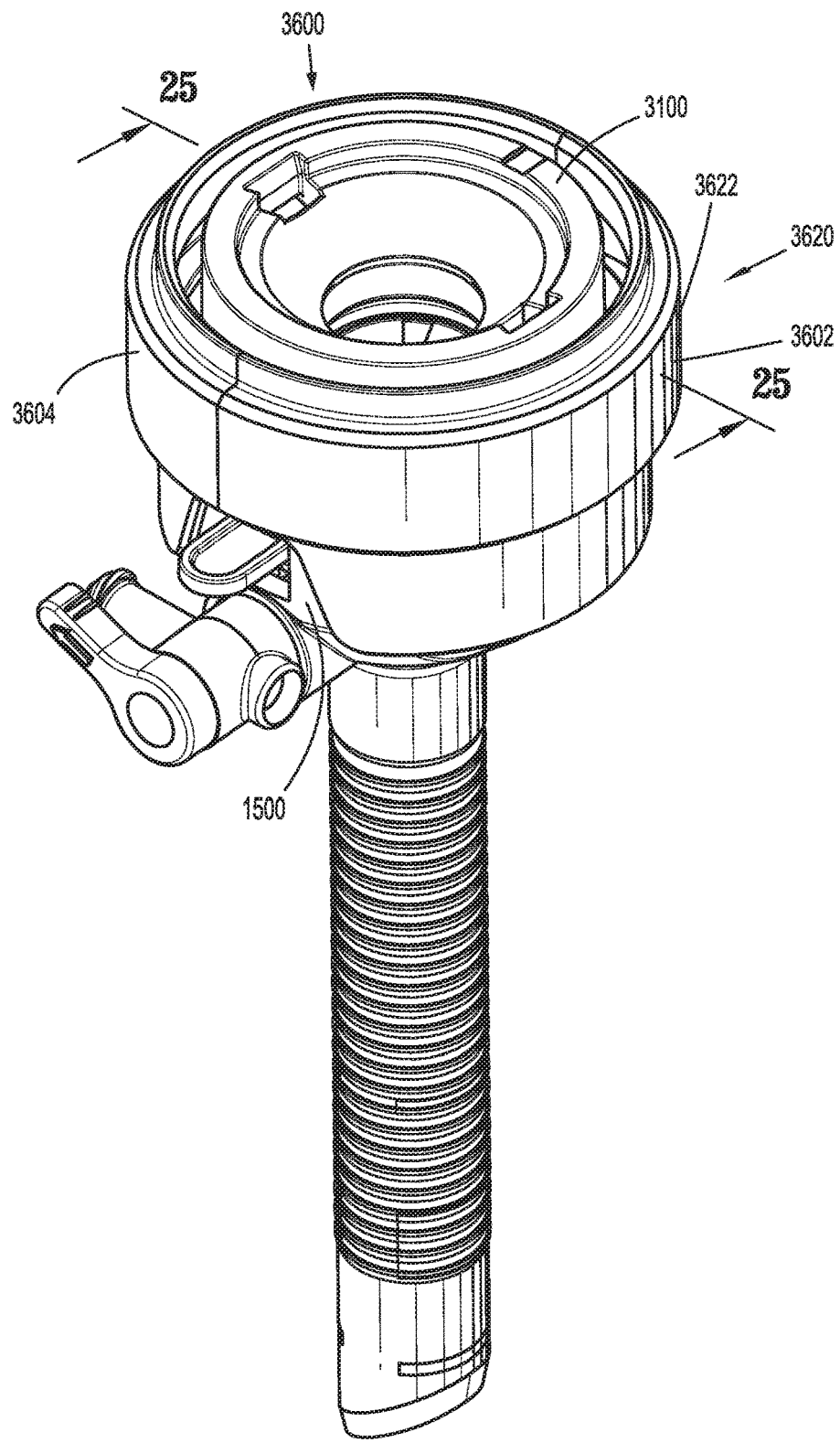
FIG. 23 is a perspective view of the surgical port of FIG. 16, with an embodiment of a seal housing and an adapter shell in accordance with the present disclosure.
Figure 24:
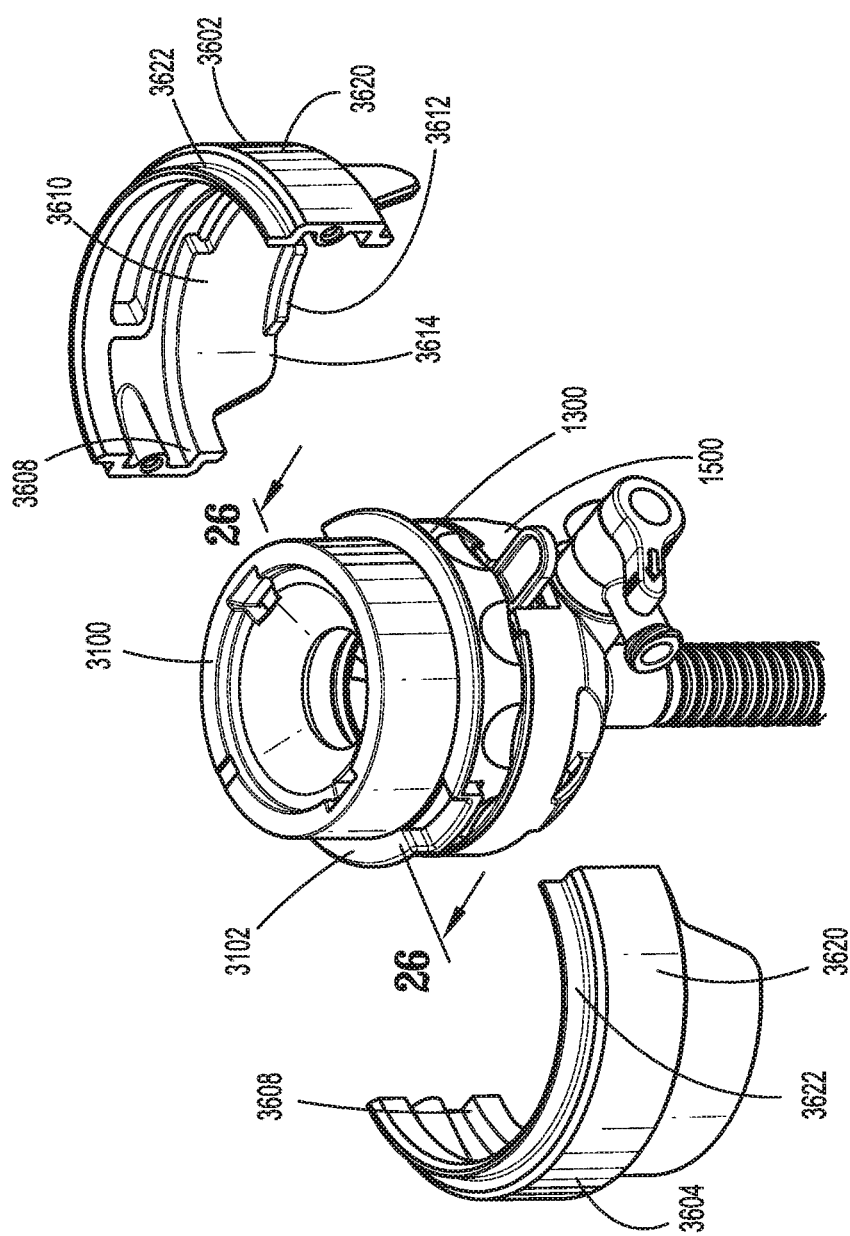
FIG. 24 is a perspective view of the surgical port of FIG. 23 with the adapter shell removed.

With reference to FIGS. 21-22B, in another embodiment of surgical port 1000, surgical port 1000 includes seal housing 1100, seal assembly 1200, a seal cover 2300, cannula seal 1400, and cannula assembly 2500. Seal cover 2300 and cannula assembly 2500 include similar features to that of seal cover 1300 and cannula assembly 1500, respectively, and therefore, for the sake of brevity and clarity only distinctions will be discussed herein below.

With respect to the engagement and coupling of seal cover 2300 and cannula assembly 2500, a distal portion 2302 of seal cover 2300 is configured to couple with a proximal portion 2502 of cannula assembly 2500, such that a secure and fluid tight seal is maintained therebetween. Distal portion 2302 of seal cover 2300 includes at least one engagement region 2310 disposed radially about distal portion 2302, and proximal portion 2502 of cannula assembly 2500 includes at least one engagement cavity 2512 disposed radially about proximal portion 2502. A respective engagement region 2310 of seal cover 2300 is configured to be received within, and engage by, a corresponding engagement cavity 2512 of cannula assembly 2500. With engagement region 2310 and engagement cavity 2512 securely coupled, seal cover 2300 and cannula assembly 2500 thereby fluidly seal cannula seal 1400 therebetween.

More particularly, and with reference to FIGS. 22A and 22B, engagement region 2310 of seal cover 2300 includes opposing channels 2312 extending proximally from distal portion 2302, and a base 2314 defined therebetween. Each channel 2312 is laterally offset from, and parallel to, one another, where channels 2312 are positioned on opposing sides of base 2314. Cannula assembly 2500 includes opposing flanges 2514 disposed at, and extending radially inward from, proximal portion 2502, where opposing flanges 2514 are disposed on either side of engagement cavity 2512.

During coupling of seal cover 2300 and cannula assembly 2500, engagement cavity 2512 of cannula assembly 2500 is configured to receive base 2314 of engagement region 2310 of seal cover 2300, whereas opposing flanges 2514 of cannula assembly 2500 are configured to be received within, and engaged by, opposing channels 2312 of engagement region 2310 of seal cover 2300. Accordingly, abutment between, and engagement of, engagement cavity 2512 and base 2314, and opposing flanges 2514 and opposing channels 2312, securely couple and affix seal cover 2300 and cannula assembly 2500.

With reference to FIGS. 23-27, in another embodiment of surgical port 1000, surgical port 1000 includes a seal housing 3100, seal assembly 1200, seal cover 1300 or seal cover 2300, cannula seal 1400, cannula assembly 1500 or cannula assembly 2500, and an adapter shell 3600. Seal housing 3100 includes similar features to that of seal housing 1100, and therefore, for the sake of brevity and clarity only distinctions will be discussed herein below. Further still, for the sake of brevity, seal housing 3100 will be discussed with reference to seal cover 1300.

Seal housing 3100 includes a flange 3102 extending radially outward from a distal portion 3104 thereof. With seal housing 3100 coupled to seal cover 1300, flange 3102 is configured to extend radially beyond an outer surface 1330 of seal cover 1300, such that flange 3102 of seal housing 3100 defines an outer diameter which is larger than an outer diameter of seal cover 1300.

Adapter shell 3600 includes a first half 3602 and a second half 3604 configured to selectively engage one another, such that first and second halves 3602, 3604 may be affixed to one another. Each of first and second halves 3602, 3604 includes an intermediate lip 3608 and a distal lip 3612. Intermediate lip 3608 is defined radially about, and extending inward from, an inner surface 3610 of each of first and second halves 3602, 3604. Distal lip 3612 is disposed at a distal portion 3614 of first and second halves 3602, 3604, and extends radially about at least a portion of inner surface 3610 and extends radially inward therefrom. When affixed, first and second halves 3602, 3604 define a cavity 3606 therebetween. Cavity 3606 is configured to receive a portion of surgical port 1000, and more specifically, is configured to enclose seal housing 3100 and seal cover 1300.

Figure 25:
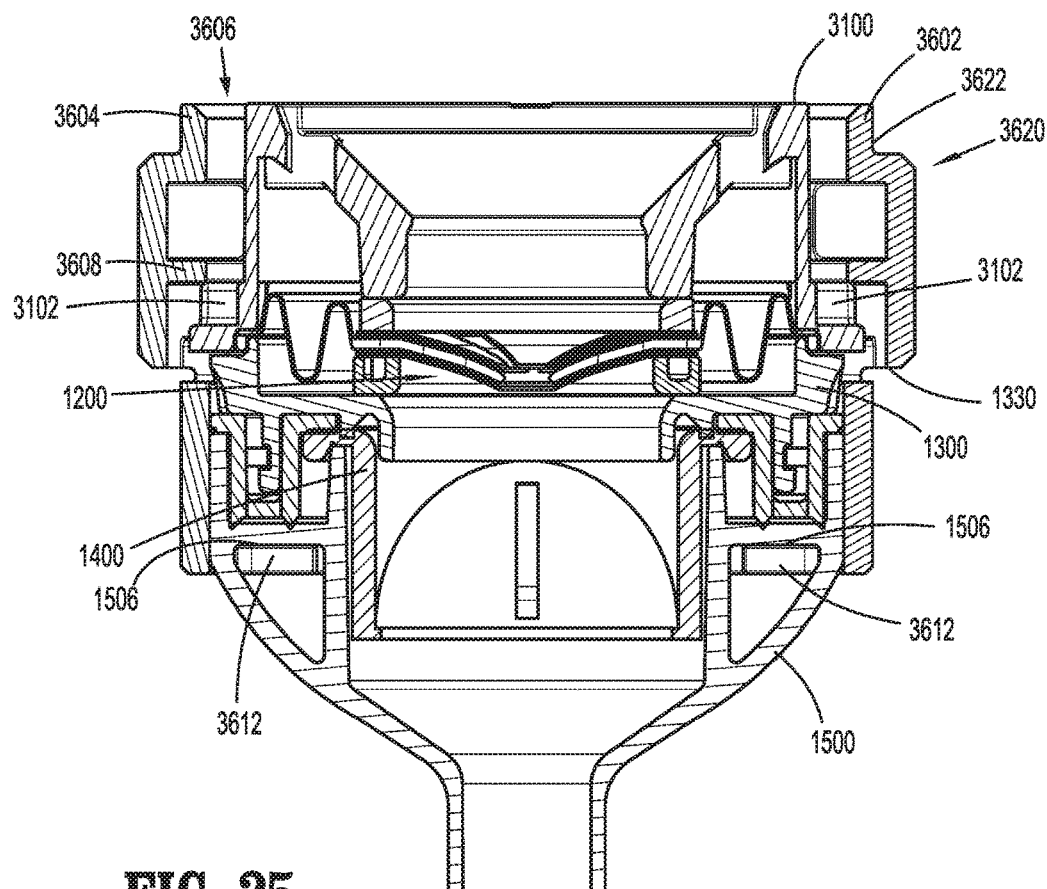
FIG. 25 is a cross-sectional view of the surgical port of FIG. 23 taken along section line 25-25 of FIG. 23.
Figure 26:
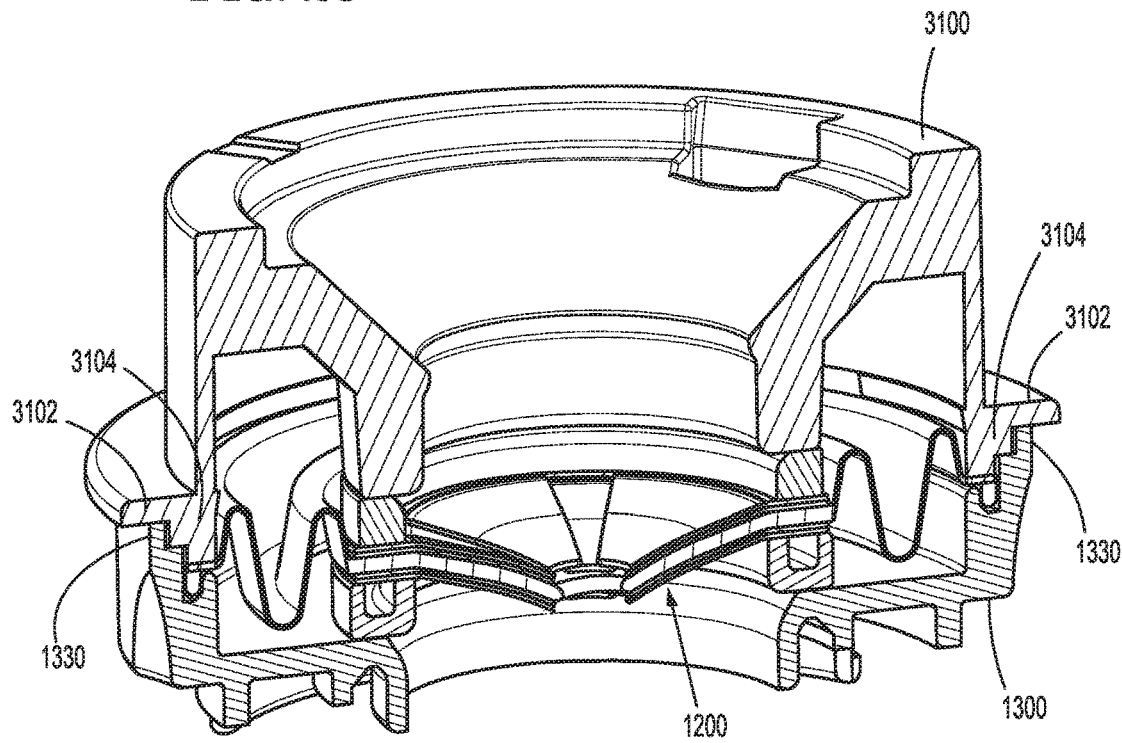
FIG. 26 is a cross-sectional view of the surgical port of FIG. 24 taken along section line 26-26 of FIG. 24.
Figure 27:
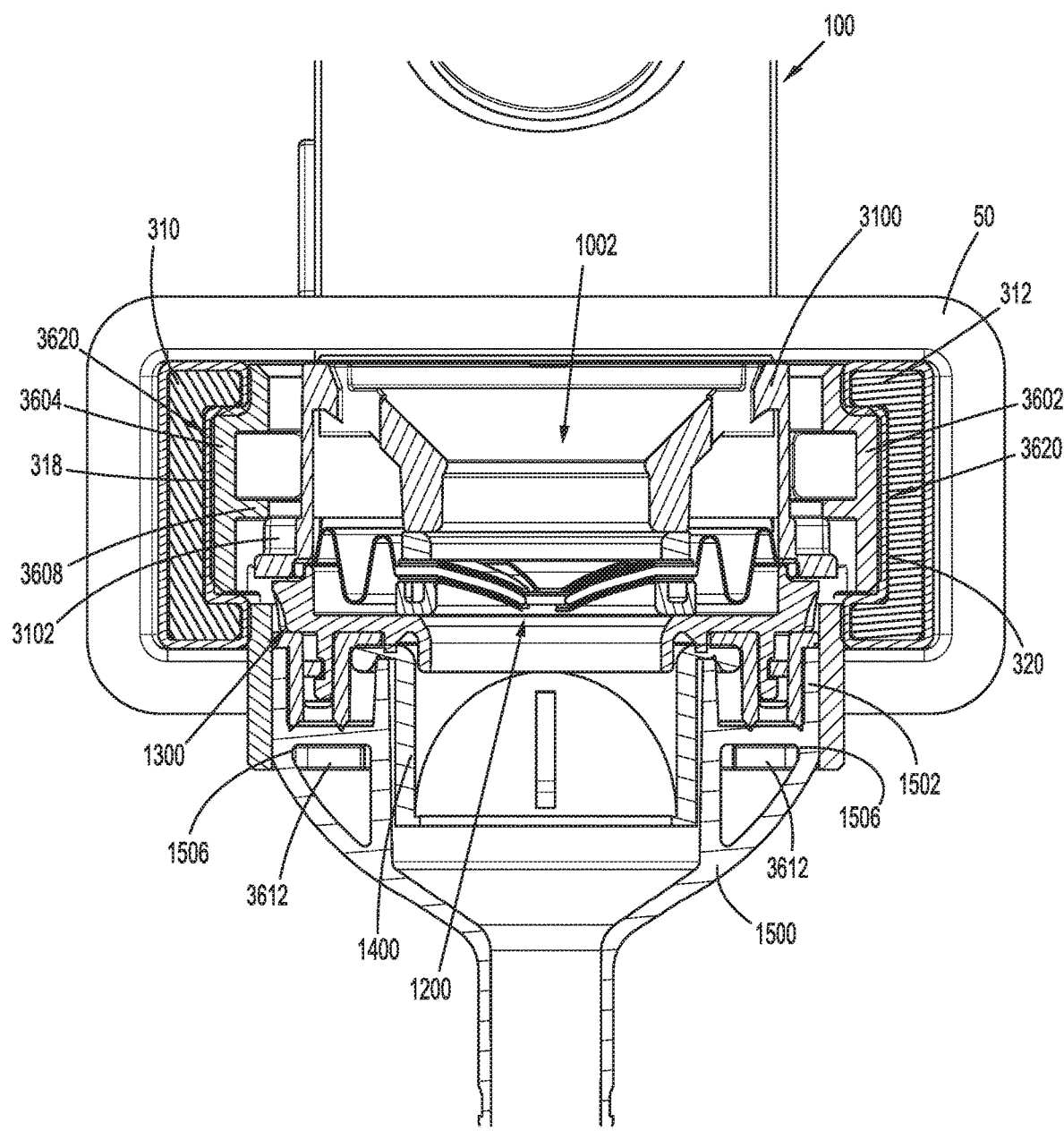
FIG. 27 is a cross-sectional view of the mount assembly of FIG. 13B and the surgical port of FIG. 23 taken along section line 27-27 of FIG. 13B.

With adapter shell 3600 positioned around seal housing 3100 and seal cover 1300, flange 3102 of seal housing 3100 provides a landing surface for each of first and second halves 3602, 3604 of adapter shell 3600. A portion of flange 3102 of seal housing 3100 comes into abutment with intermediate lip 3608 of first and second halves 3602, 3604. Further, distal lip 3612 comes into engagement with a lip recess 1506 defined on proximal portion 1502 of cannula assembly 1500 (FIG. 25). As a result of the abutment between flange 3102 of seal housing 3100 and intermediate lip 3608 of adapter shell 3600, and the engagement between distal lip 3612 of adapter shell 3600 and lip recess 1506 of cannula assembly 1500, linear movement and/or uncoupling of seal housing 3100 with respect to cannula assembly 1500 is thereby inhibited, and thus, seal housing 3100 and seal cover 1300 may be securely coupled. Further still, by reducing a distance or gap between intermediate lip 3608 and distal lip 3612, once adapter shell 3600 is disposed about and coupled to seal housing 3100 and cannula assembly 1500, intermediate and distal lips 3608, 3612 of adapter shell 3600 may provide linear compression between seal housing 3100 and cannula assembly 1500, such that coupling therebetween is thereby enhanced.

With reference to FIGS. 13A, 13B, 23, and 27, first and second halves 3602, 3604 of adapter shell 3600 further include an engagement region 3620 disposed about an external surface 3622 thereof. Engagement region 3620 is configured to mate with engagement portions 126, 136 of fixed and movable arms 122, 132 of coupling assembly 120, or engagement portions 318, 320 of first and second arms 310, 312 of coupling assembly 300. More particularly, engagement region 3620 and engagement portions 126, 136 of fixed and movable arms 122, 132 of coupling assembly 120, and/or engagement portions 318, 320 of first and second arms 310, 312 of coupling assembly 300, are configured to define corresponding profiles such that abutment and fixation therebetween may be achieved. It should be appreciated that the generally circular cross-sectional profile of engagement region 3620, and the corresponding arcuate profile of fixed and movable arms 122, 132, and first and second arms 310, 312, provide surgical port 1000 with a rotational degree of freedom, about a longitudinal axis defined along central lumen 1002.

As coupling assemblies 120, 300 transition from the open configuration (FIGS. 10A and 13A) to the closed configuration (FIGS. 9A, 13B, and 27), engagement portions 126, 136 of coupling assembly 120, and engagement portions 318, 320 of coupling assembly 300, come into abutment with and clamp about engagement region 3620 of adapter shell 3600. Accordingly, with coupling assemblies 120, 300 in the closed configuration, fixed and movable arms 122, 132 of coupling assembly 120, and first and second arms 310, 312 of coupling assembly 300, are aligned with, and securely affixed to, engagement region 3620 of adapter shell 3600, and thus, surgical port 1000 may be affixed to mount assembly 100 and robot arm 2.

Figure 28:
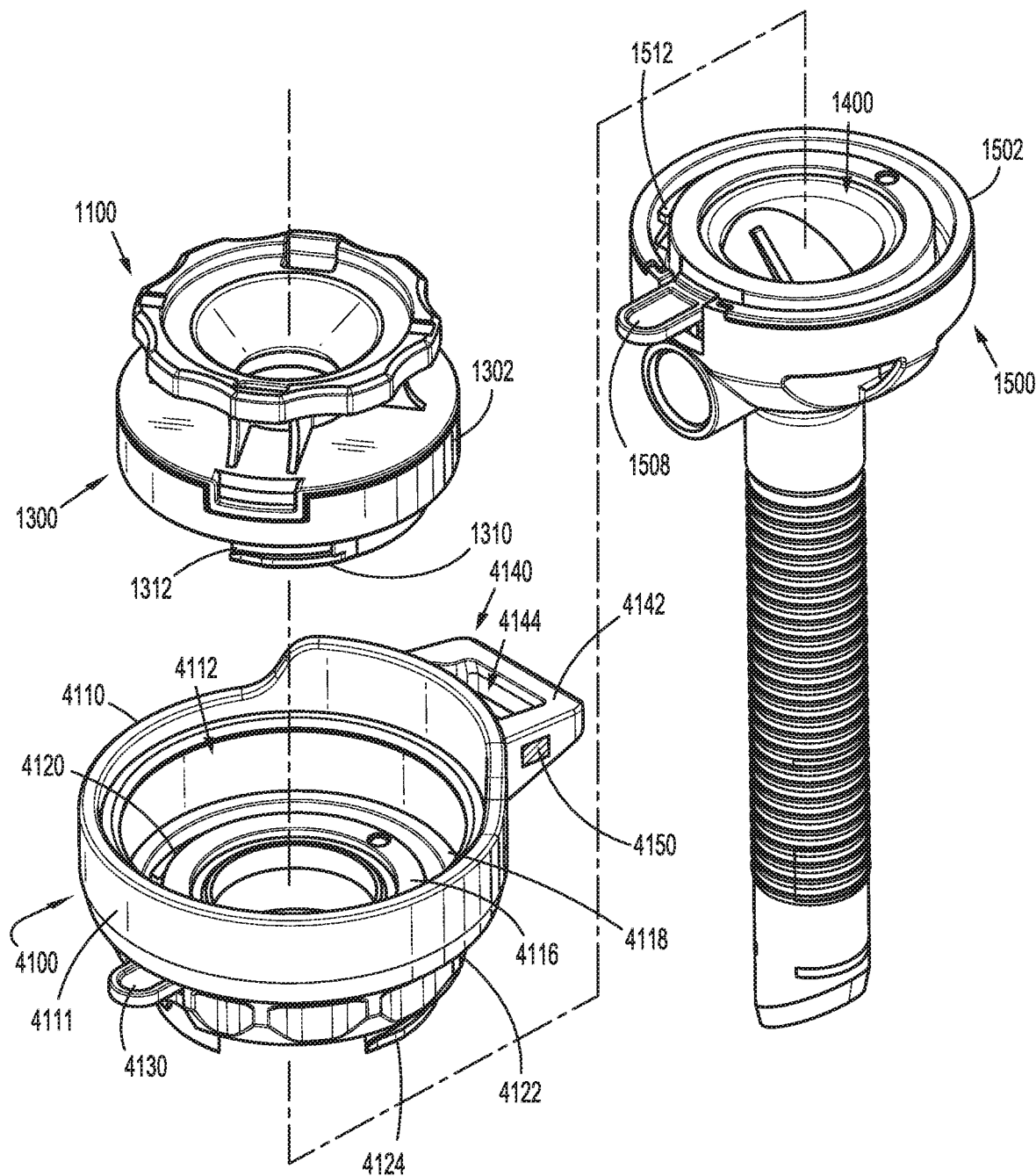
FIG. 28 is a perspective view, with some parts separated, of the surgical port of FIG. 16, with an embodiment of a mount adapter in accordance with the present disclosure.
Figure 29:
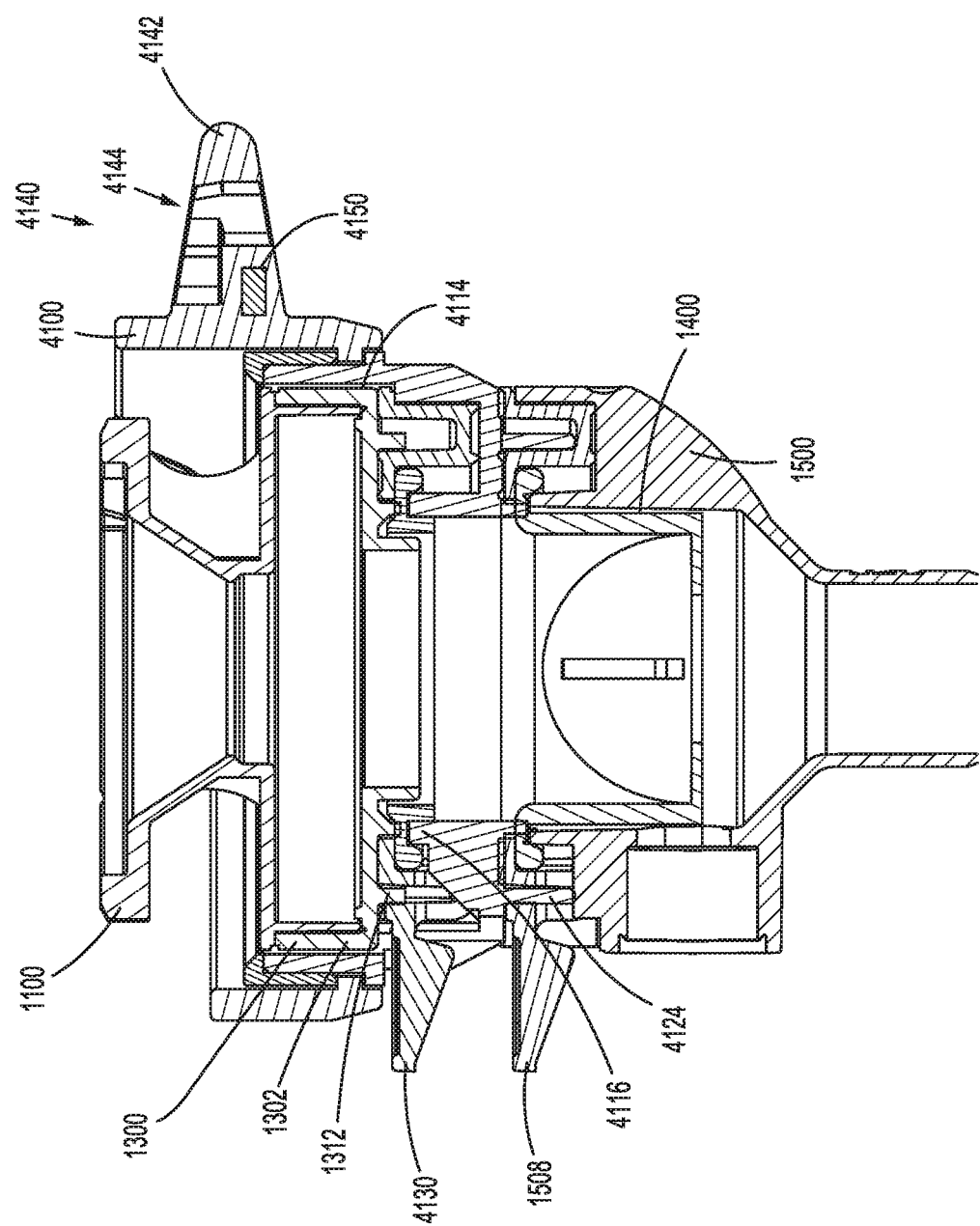
FIG. 29 is a cross-sectional view of the mount assembly of FIG. 14A and the surgical port of FIG. 28 taken along section line 29-29 of FIG. 14A.

With reference to FIGS. 28 and 29, in another embodiment of surgical port 1000, surgical port 1000 includes seal housing 1100 or seal housing 3100, seal assembly 1200, seal cover 1300 or seal cover 2300, cannula seal 1400, cannula assembly 1500 or cannula assembly 2500, and a mount adapter 4100. For the sake of brevity and clarity, mount adapter 4100 will be discussed herein with reference to seal housing 1100, seal assembly 1200, seal cover 1300, cannula seal 1400, and cannula assembly 1500.

Mount adapter 4100 is configured to couple between seal cover 1300 and cannula assembly 1500, and provides an alternative method of selectively coupling surgical port 1000 to mount assembly 100, as discussed further below. Mount adapter 4100 includes a body 4110 defining a through-hole 4112, a release tab 4130 extending from a perimeter 4111 of body 4110, and an engagement region 4140 extending from perimeter 4111 of body 4110. It is envisioned that mount adapter 4100 may further include a mount adapter seal assembly (not shown) disposed within through-hole 4112 and configured to receive a surgical instrument "SI" therethrough. In such an embodiment, the mount adapter seal assembly may include, for example, a captive seal, configured to maintain internal fluidic pressures of the patient's body cavity with, or without surgical instrument "SI" present.

Body 4110 of mount adapter 4100 includes an inner surface 4114 defining through-hole 4112, a flange 4116 disposed about a distal portion 4118 of inner surface 4114 and extending radially inward therefrom, and a coupling feature 4120 disposed along flange 4116. During coupling, seal housing 1100 and seal cover 1300 are positioned within through-hole 4112 of body 4110 of mount adapter 4100, proximal of flange 4116, such that distal portion 1302 of seal cover 1300 is brought into abutment with flange 4116 of body 4110. Distal portion 1302 of seal cover 1300 is configured to engage and couple with coupling feature 4120. In an embodiment, seal cover 1300 may be coupled to coupling feature 4120 of flange 4116 in a similar manner as when coupling seal cover 1300 and cannula assembly 1500 (e.g., key feature 1312 of lobe 1310 of seal cover 1300 is brought into abutment to, and coupled with, key feature 1512 of cannula assembly 1500, as discussed above, whereas coupling feature 4120 of adapter mount 4100 defines a similar coupling feature to that of key feature 1512 of cannula assembly 1500).

With seal housing 1100 and seal cover 1300 coupled to mount adapter 4100, a distal portion 4122 of body 4110 of mount adapter 4100 may be coupled to proximal portion 1502 of cannula assembly 1500. More particularly, a distal coupling feature 4124 radially disposed about distal portion 4122 of body 4110 is configured to engage and couple with proximal portion 1502 of cannula assembly 1500. It should be appreciated that distal coupling feature 4124 of mount adapter 4100 may engage and couple with cannula assembly 1500 in a similar manner as seal cover 1300 and cannula assembly 1500, as discussed above.

During uncoupling of seal cover 1300 from mount adapter 4100, release tab 4130 may be actuated such that distal portion 1302 of seal cover 1300 and coupling feature 4120 of mount adapter 4100 are thereby disengaged. With seal cover 1300 and mount adapter 4100 disengaged, seal cover 1300 may be withdrawn from through-hole 4112 of mount adapter 4100. In a similar manner, mount adapter 4100 may be uncoupled from cannula assembly 1500. More particularly, a release tab 1508 disposed about the proximal portion 1502 of cannula assembly 1500 (FIGS. 28 and 29) may be articulated, thereby disengaging the distal coupling feature 4124 from the proximal portion 1502 of cannula assembly 1500.

With reference to FIGS. 14A-15, 28, and 29, engagement region 4140 of mount adapter 4100 includes a frame 4142 and a cavity 4144 defined therethrough. Cavity 4144 is configured to receive, while frame 4142 is configured to engage, hooked portion 412 of latch 410 of coupling assembly 400 of mount assembly 100. More particularly, and as discussed above in more detail with respect to coupling assembly 400 of mount assembly 100, during coupling of mount adapter 4100 and coupling assembly 400, hooked portion 412 of latch 410 pivots into cavity 4144 of engagement region 4140 and into engagement with frame 4142 (FIGS. 14B and 15). With frame 4142 pivotally coupled to seal and cannula assemblies 1200, 1500 disposed therethrough such that engagement region 4140 may be coupled to robot arm 2, port 1000 can rotate around the insertion axis (e.g., single degree of freedom). During uncoupling of mount adapter 4100 and coupling assembly 400, hook portion 412 of latch 410 pivots out of engagement with frame 4142 and out of cavity 4144 (FIG. 14A).

Mount adapter 4100 may further include a contact sensor 4150 disposed on body 4110. In an exemplary embodiment, contact sensor 4150 is disposed on or within frame 4142 of engagement region 4140. Contact sensor 4150 is configured for communication with communication assembly 200 of mount assembly 100, as discussed in further detail above, and may mechanically engage presence sensor switch 230 and/or wirelessly communicate with presence sensor switch 230 or communication assembly 200. Contact sensor 4150, together with communication assembly 200, provides work station 1 with an indication regarding the presence, or absence of mount adapter 4100 of surgical port 1000, with respect to coupling assembly 400 of mount assembly 100, and may further provide an indication of incorrect, partial, or misaligned mounting therebetween.

In an embodiment configured for mechanical communication, as latch 410 pivots and hooked portion 412 engages engagement region 4140, latch 410 may be configured to depress or otherwise close or contact presence sensor switch 230, indicating the presence of mount adapter 4100 therewith. In an embodiment configured for non-contact or wireless communication, contact sensor 4150 of mount adapter 4100 may be configured for wireless communication with communication assembly 200 by any wireless communication method as is known in the art, such as, for example, magnetic registration, BlueTooth, ZigBee, near field communication (NFC), WiFi, or the like. In such an embodiment, once mount adapter 4100 is coupled with coupling assembly 400 of mount assembly 100, contact sensor 4150 is thereby brought into close proximity to communication assembly 200 of mount assembly 100. With contact sensor 4150 in close proximity to communication assembly 200, contact sensor 4150 may be wirelessly registered by communication assembly 200, and thus, the presence of mount adapter 4100 may be determined and communicated to work station 1.

Mount adapter 4100 may be constructed from any biocompatible material as is known in the art, and may be configured to be a disposable-single use device, or capable of withstanding sterilization for reuse. Further still, mount adapter 4100, and more particularly engagement region 4140 of mount adapter 4100, may be further configured to cooperatively act with sterile drape 50. In such an embodiment, sterile drape 50 may be positioned between engagement region 4140 and coupling assembly 400 prior to coupling, whereby hooked portion 412 of latch 410 of coupling assembly 400 deforms sterile drape 50, or is otherwise uninhibited from engaging frame 4142 of engagement region 4140. It should be appreciated that during coupling, engagement region 4140, hooked portion 412 of latch 410, and sterile drape 50 are configured to inhibit a breach, tear, or compromise of the integrity of sterile drape 50, such that the sterile barrier therebetween may be maintained.

With reference to FIGS. 1-29, a kit in accordance with the present disclosure may include one or more mount assemblies 100 having any of coupling assemblies 120, 300, or 400. In an embodiment, the kit further includes at least one surgical accessory, such as, for example, surgical port 1000, a trocar, or an illumination device. Further, the kit may additionally or alternatively include at least one mount adapter 4100. Further still, in an embodiment, the kit includes at least one surgical instrument, such as, for example, an obturator, a pair of jaw members, electrosurgical forceps, cutting instruments, or any other endoscopic or open surgical devices. The kit may additionally include Instructions for Use ("IFU"), which provides a clinician with instructions regarding the coupling and uncoupling of mount assembly 100, and/or assembly or disassembly of surgical port 1000.

Figure 30:
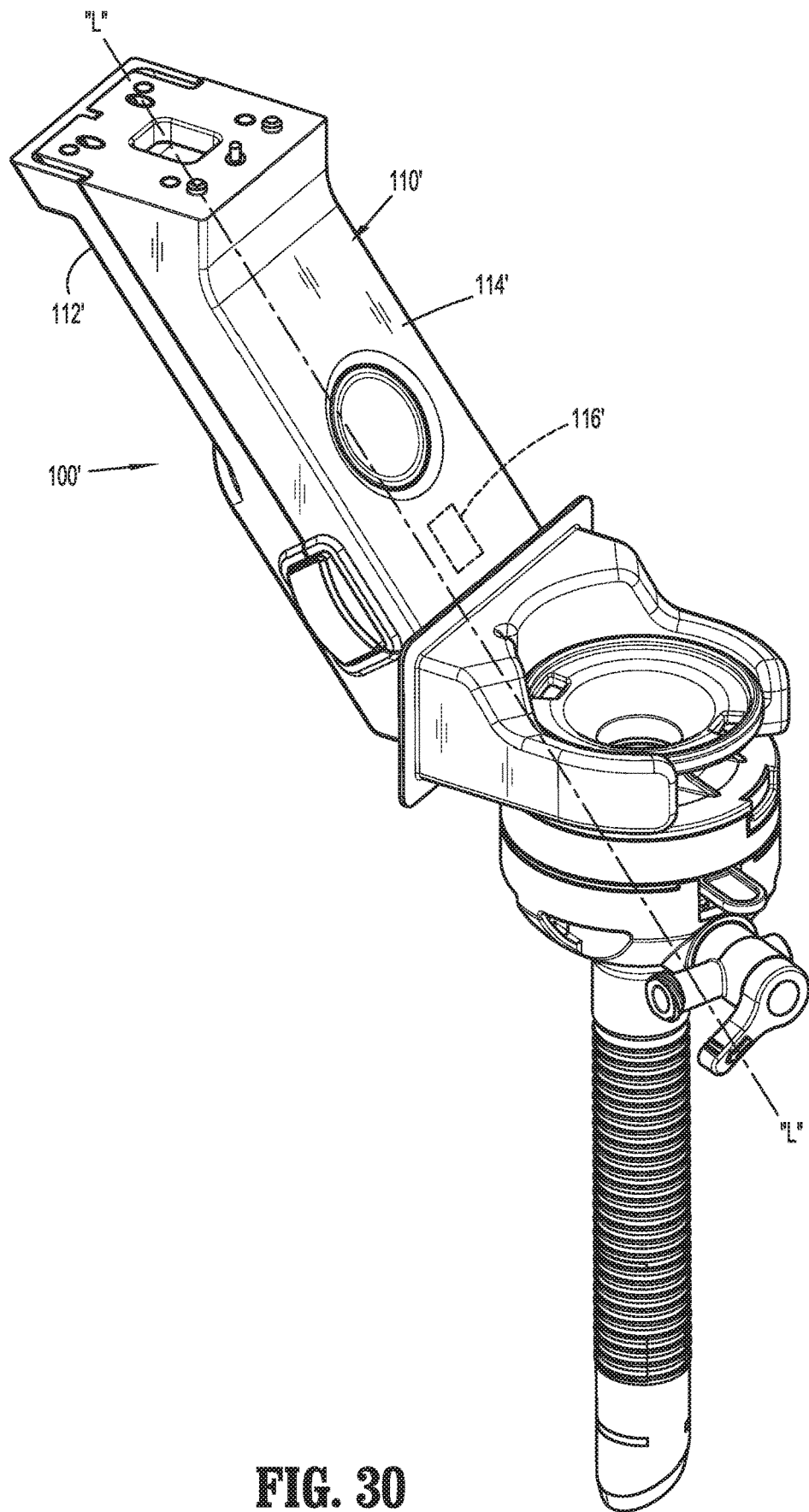
FIG. 30 is a perspective view of another embodiment of a mount assembly shown coupled to and supporting a surgical port.

Turning now to FIG. 30, another embodiment of a mount assembly, generally referred to as 100' is similar to mount assembly 100, but includes a housing 110' having a proximal portion 112' and distal portion 114'. Housing 110' may be wholly or partially formed of any suitable insulative or dielectric material such a polymeric material to electrically isolate a patient from at least portions of a medical work station (e.g., instrument drive unit, robotic arms, etc.). For example, proximal portion 112' may include a conductive material such as any suitable metallic material and distal portion 114' may include a polymeric material such as rubber or the like. Advantageously, if distal portion 114' of housing 110' contacts a patient during use (e.g., if the patient has a return pad or other device that acts as an electrode), the insulative material of distal portion 114' prevents electrical communication between the patient and the insulative material. Mount assembly 100' includes an isolation chip 116' that can similarly function to electrically isolate one or more electrical components of the medical work station. For example, isolation chip 116' may be electrically coupled to a communication assembly supported within housing 110' (and which may be similar to communication assembly 200) (see, e.g., FIG. 4).

It will be understood that various modifications may be made to the embodiments disclosed herein. Therefore, the above description should not be construed as limiting, but merely as exemplifications of various embodiments. Those skilled in the art will envision other modifications within the scope and spirit of the claims appended thereto.

What is claimed is:

1. A mount assembly for use with a robotic system, the mount assembly comprising:
   a housing configured to couple to a robot arm of a robotic system;
   a coupling assembly supported by the housing and including a first arm and a second arm, the coupling assembly transitionable between open and closed configurations, wherein in the open configuration first and second arms pivot into a relatively more spaced apart relation with respect to one another, and in the closed configuration first and second arms pivot into a relatively more approximated relation with respect to one another, wherein in the closed configuration the first and second arms are configured to secure a surgical port to the robot arm;
   a release assembly supported by the housing and engagable with the coupling assembly, the release assembly transitionable between a locked configuration and an unlocked configuration with respect to the coupling assembly, wherein in the locked configuration of the release assembly the first and second arms of the coupling assembly are fixed in the closed configuration;
   a latch plate including a pivot pin and an engagement pin, the pivot pin pivotably coupling the latch plate to the first arm, and the engagement pin operably coupled to the release assembly such that movement of the release assembly between the locked configuration and the unlocked configuration causes the latch plate to pivot relative to the first arm about the pivot pin; and
   a communication assembly supported by the housing and configured for communication with the robotic system with respect to:
      a status of the coupling assembly corresponding to the open and closed configuration thereof; and
      a status of the release assembly corresponding to the locked and unlocked configuration thereof.

2. The mount assembly of claim 1, wherein the communication assembly includes:
   a release assembly sensor switch configured for selective engagement with the release assembly, wherein when the release assembly transitions to the locked configuration the release assembly sensor switch is engaged;
   a button pivotably disposed within a cavity of the second arm of the coupling assembly, the button configured for engagement by a surgical port secured between first and second arms of the coupling assembly; and
   a presence sensor switch configured for selective engagement with the button, wherein when the button is engaged by the surgical port the button pivots into engagement with the presence sensor switch.

3. The mount assembly of claim 1,
   wherein, in the locked configuration of the release assembly, a protrusion of the latch plate is engaged with a portion of the first arm of the coupling assembly; and
   wherein, in the unlocked configuration of the release assembly, the protrusion of the latch plate is disengaged from the portion of the first arm of the coupling assembly.

4. The mount assembly of claim 1, wherein the coupling assembly includes a biasing member coupled between the first and second arms, the biasing member configured to bias the coupling assembly into one of the open or closed configurations.

5. The mount assembly of claim 1, wherein the first arm of the coupling assembly is pivotably coupled to a portion of the second arm, and the second arm is fixedly supported by the housing.

6. The mount assembly of claim 1, wherein the first and second arms are pivotably coupled to the housing.

7. The mount assembly of claim 1, wherein the release assembly includes a biasing member configured to bias the release assembly into one of the locked or unlocked configurations.

8. The mount assembly of claim 1, wherein the release assembly includes a first actuation lever coupled to the first arm of the coupling assembly and a second actuation lever coupled to the second arm of the coupling assembly, the first and second actuation levers configured to transition the first and second arms of the coupling assembly between the open and closed configurations, and the locked and unlocked configurations.

9. The mount assembly of claim 1, wherein each of the first and second arms includes an engagement region thereon configured to engage a surgical port while in the closed configuration of the coupling assembly, the engagement regions of the first and second arms defining a complementary shape with respect to an outer surface of a surgical port.

10. The mount assembly of claim 9, wherein each of the engagement regions defines an inner surface and includes a flange extending therefrom, the flange being configured to engage a portion of a surgical port while in the closed configuration of the coupling assembly.

11. A robotic system comprising:
a surgical port configured to receive a surgical instrument therethrough, the surgical port including:
a seal housing having an engagement region disposed about an external radial surface thereof;
a seal cover having a plurality of lobes radially disposed along a distal portion thereof, each lobe of the plurality of lobes including a key feature thereon;
a cannula assembly having a plurality of key features radially disposed along a proximal portion thereof, each respective key feature of the cannula assembly corresponding to, and configured to engage with, a key feature of a respective lobe of the plurality of lobes of the seal cover, wherein the surgical port includes a central lumen defined by an inner surface of each of the seal housing, the seal cover, and the cannula assembly;
a seal assembly coupled between the seal housing and the seal cover; and
a cannula seal coupled between the seal cover and the cannula assembly, the seal assembly and the cannula seal configured to maintain a fluidic seal within the central lumen of the surgical port; and
a mount assembly configured to couple to a robot arm of the robotic system, the mount assembly including:
a coupling assembly including a first arm and a second arm, the coupling assembly transitionable between open and closed configurations, wherein in the open configuration first and second arms pivot into relatively more spaced relation with respect to one another, and in the closed configuration first and second arms pivot into a relatively more approximated relation with respect to one another, wherein in the closed configuration the first and second arms selectively secure the engagement region of the seal housing of the surgical port therebetween;
a release assembly engaged with the coupling assembly and transitionable between a locked configuration and an unlocked configuration with respect to the coupling assembly, wherein in the locked configuration of the release assembly the first and second arms of the coupling assembly are pivotably fixed in the closed configuration; and
a latch plate including a pivot pin and an engagement pin, the pivot pin pivotably coupling the latch plate to the first arm, and the engagement pin operably coupled to the release assembly such that movement of the release assembly between the locked configuration and the unlocked configuration causes the latch plate to pivot relative to the first arm about the pivot pin.

12. The robotic system of claim 11, wherein the mount assembly further includes a communication assembly configured for communication with the robotic system with respect to:
a status of the coupling assembly corresponding to the open and closed configuration thereof; and
a status of the release assembly corresponding to the locked and unlocked configuration thereof.

13. The robotic system of claim 12, wherein the communication assembly includes:
a release assembly sensor switch configured for selective engagement with the release assembly, wherein when the release assembly transitions to the locked configuration the release assembly sensor switch is engaged;
a button pivotably disposed within a cavity of the second arm of the coupling assembly, the button configured for engagement by a surgical port secured between first and second arms of the coupling assembly; and
a presence sensor switch configured for selective engagement with the button, wherein when the button is engaged by the surgical port the button pivots into engagement with the presence sensor switch.

14. The robotic system of claim 11, wherein the first arm of the coupling assembly is pivotably coupled to a portion of the second arm, and the second arm is fixedly supported by the housing.

15. The robotic system of claim 11, wherein the first and second arms are pivotably coupled to the housing.

16. A mount assembly for use with a robotic system, the mount assembly comprising:
a housing configured to couple to a robot arm of a robotic system;
a coupling assembly supported by the housing and including a first arm and a second arm, the coupling assembly transitionable between open and closed configurations, wherein in the open configuration first and second arms pivot into a relatively more spaced apart relation with respect to one another, and in the closed configuration first and second arms pivot into a relatively more approximated relation with respect to one another, wherein in the closed configuration the first and second arms are configured to secure a surgical port to the robot arm;
a release assembly supported by the housing and engagable with the coupling assembly, the release assembly transitionable between a locked configuration and an unlocked configuration with respect to the coupling assembly, wherein in the locked configuration of the release assembly the first and second arms of the coupling assembly are fixed in the closed configuration; and
a latch plate including a pivot pin and an engagement pin, the pivot pin pivotably coupling the latch plate to the first arm, and the engagement pin operably coupled to the release assembly such that movement of the release assembly between the locked configuration and the unlocked configuration causes the latch plate to pivot relative to the first arm about the pivot pin.

17. The mount assembly of claim 16, further comprising a communication assembly configured to communicate a status of at least one of the coupling assembly or the release assembly to the robotic system.

18. The mount assembly of claim 17, wherein the communication assembly includes at least one of:
a release assembly sensor switch configured for selective engagement with the release assembly, wherein when the release assembly transitions to the locked configuration the release assembly sensor switch is engaged;
a button pivotably disposed within a cavity of the second arm of the coupling assembly, the button configured for engagement by a surgical port secured between first and second arms of the coupling assembly; or
a presence sensor switch configured for selective engagement with the button, wherein when the button is engaged by the surgical port the button pivots into engagement with the presence sensor switch.

19. The mount assembly of claim 16, wherein the first arm of the coupling assembly is pivotably coupled to a portion of the second arm, and the second arm is fixedly supported by the housing.

20. The mount assembly of claim 16, wherein the first and second arms are pivotably coupled to the housing.

\* \* \* \* \*